United States Patent
Hsiao et al.

(10) Patent No.: US 9,969,970 B2
(45) Date of Patent: May 15, 2018

(54) DNA-CELL CONJUGATES

(71) Applicant: The Regents of the University of California, Oakland, CA (US)

(72) Inventors: Shih-Chia Hsiao, Oakland, CA (US); Matthew B. Francis, Berkeley, CA (US); Carolyn Bertozzi, Berkeley, CA (US); Richard Mathies, Walnut Creek, CA (US); Ravi Chandra, Newton, MA (US); Erik Douglas, Oakland, CA (US); Amy Twite, Berkeley, CA (US); Nicholas Toriello, San Carlos, CA (US); Hiroaki Onoe, Tokyo (JP)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days. days.

(21) Appl. No.: 15/057,604

(22) Filed: Mar. 1, 2016

(65) Prior Publication Data
US 2016/0319238 A1 Nov. 3, 2016

Related U.S. Application Data

(62) Division of application No. 13/263,129, filed as application No. PCT/US2010/030397 on Apr. 8, 2010, now Pat. No. 9,327,036.

(60) Provisional application No. 61/167,748, filed on Apr. 8, 2009, provisional application No. 61/243,123, filed on Sep. 16, 2009.

(51) Int. Cl.
| | |
|---|---|
| C12N 5/07 | (2010.01) |
| C07H 21/00 | (2006.01) |
| C12N 5/0789 | (2010.01) |
| C12N 5/04 | (2006.01) |
| C12N 5/00 | (2006.01) |
| A61K 47/69 | (2017.01) |

(52) U.S. Cl.
CPC ........ *C12N 5/0006* (2013.01); *A61K 47/6901* (2017.08)

(58) Field of Classification Search
None
See application file for complete search history.

(56) References Cited

U.S. PATENT DOCUMENTS

| | | |
|---|---|---|
| 2006/0263336 A1 | 11/2006 | Caplan |
| 2009/0017455 A1 | 1/2009 | Kwong et al. |
| 2009/0186356 A1* | 7/2009 | Wendel ............ C12N 15/111 435/6.13 |

FOREIGN PATENT DOCUMENTS

| | | |
|---|---|---|
| WO | WO-01/79538 A2 | 10/2001 |
| WO | WO-01/79538 A3 | 10/2001 |

OTHER PUBLICATIONS

International Search Report and Written Opinion from PCT/US2010/030397, dated Sep. 14, 2010 (10 pages).
Borisenko et al., "DNA modification of live cell surface"; *Nucleic Acids Res.*; 37(4):e1-e11 (ePub Jan. 21, 2009).
Douglas, Erik S.; "Microfluidic devices for single cell manipulation and analysis," Ph.D. Dissertation, University of California, Berkeley with University of California, San Francisco, 2008.
Douglas et al., "DNA-barcode directed capture and electrochemical metabolic analysis of single mammalian cells on a microelectrode array"; *Lab Chip*; 9(14):2010-2015 (Jul. 21, 2009; ePub Apr. 15, 2009).
Hsiao et al., "Direct Cell Surface Modification with DNA for the Capture of Primary Cells and the Investigation of Myotube Formation on Defined Patterns"; *Langmuir*;.25(12): 6985-6991 (Jun. 16, 2009).
Lin et al., "Recognition Imaging with a DNA Aptamer"; *Biophys J.*; 90(11): 4236-4238 (Jun. 1, 2006).
Teramura et al., "Behavior of synthetic polymers immobilized on a cell membrane"; *Biomaterials*; 29(10):1345-55 (Apr. 2008).
Toriello et al., "Integrated microfluidic bioprocessor for single-cell gene expression analysis"; *PNAS USA*. 105(51):20173-20178 (Dec. 23, 2008).
Hsiao, et al., "DNA-Coated AFM Cantilevers for the Investigation of Cell Adhesion and the Patterning of Live Cells," *Angew Chem Int Ed.*, vol. 47, pp. 8473-8477 (2008).
Tong, et al., "Viral Capsid DNA Aptamer Conjugates as Multivalent Cell-Targeting Vehicles," *J Am Chem Soc.*, vol. 131, pp. 11174-11178 (2009).
Duckworth, et al., "A Universal Method for the Preparation of Covalent Protein—DNA Conjugates for Use in Creating Protein Nanostructures," *Angew. Chem. Int. Ed.*, vol. 46, pp. 8819-8822 (2007).
Jongsma, et al., "Self-assembling protein arrays on DNA chips by auto-labeling fusion proteins with a single DNA address," *Proteomics*, vol. 6, pp. 2650-2655 (2006).
Murakami, et al., "Highly sensitive detection of DNA using enzyme-linked DNA-probe. 1. Colorimetric and fluorometric detection," *Nuc Acids Res.*, vol. 17, No. 14, pp. 5587-5595 (1989).
Tominaga, et al., "An enzymatic method for site-specific labeling of recombinant proteins with oligonucleotides," *Chem. Commun.*, pp. 401-403 (2007).

(Continued)

*Primary Examiner* — James D Schultz
(74) *Attorney, Agent, or Firm* — Mintz, Levin, Cohn, Ferris, Glovsky and Popeo, P.C.

(57) ABSTRACT

The present invention provides conjugates of DNA and cells by linking the DNA to a native functional group on the cell surface. The cells can be without cell walls or can have cell walls. The modified cells can be linked to a substrate surface and used in assay or bioreactors.

34 Claims, 34 Drawing Sheets

(56) References Cited

OTHER PUBLICATIONS

Chandra, et al., "Programmable Cell Adhesion Encoded by DNA Hybridization," *Angew. Chem. Int. Ed.*, vol. 45, pp. 897-901 (2006).
Douglas, et al., "Self-assembled cellular microarrays patterned using DNA barcodes," *Lab Chip*, vol. 7, pp. 1442-1448 (2007).

\* cited by examiner

A

Figure 1
B
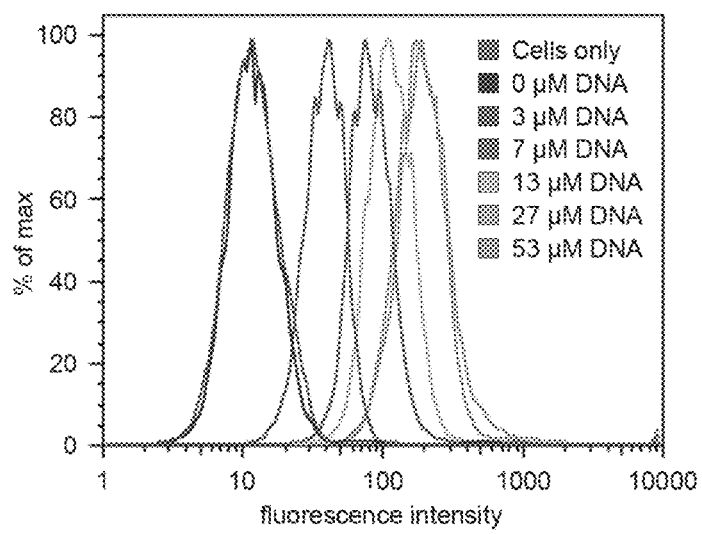
C
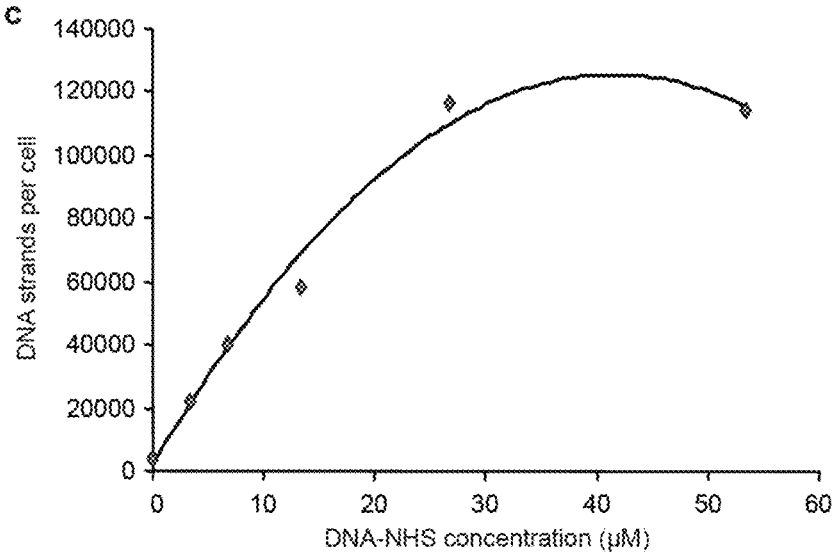

D

Figure 28B
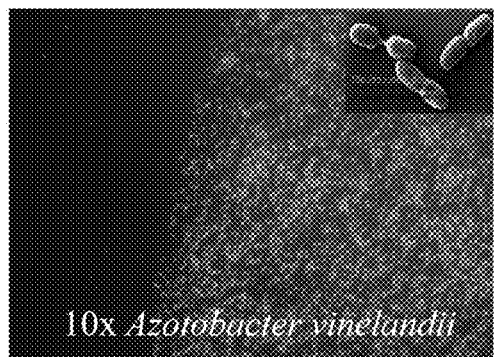
A. vinelandii
•Gram negative diazotroph
•Contains 3 aerotolerant nitrogenases
•Breaks down biomass into small organic acids for photosynthesis
•Fixes N₂ for Figure 29
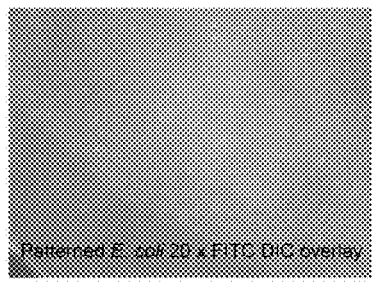
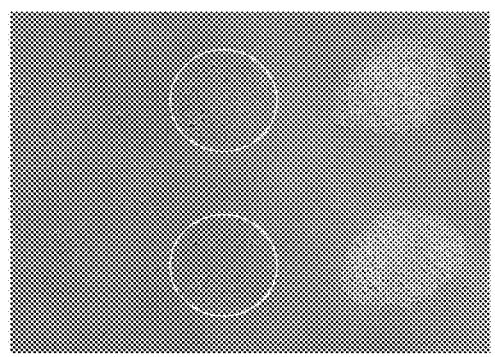
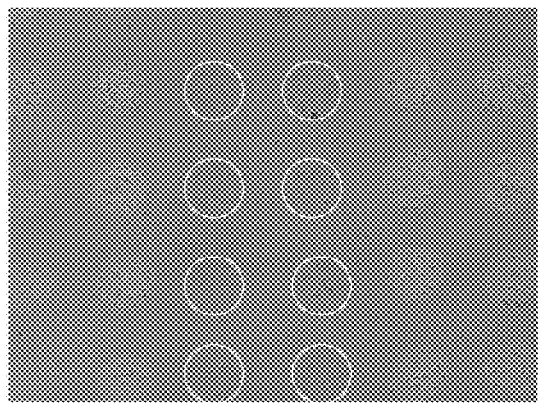
E.coli (not fluor.labeled) and Synechocystis (labeled with FITC) microarray pattern 20x (top) and 10x (bottom)

- Takes advantage of lack of mixing at microscale dimensions for more efficient e- transport for MFC application Figure 31A
| Cell Name | Cell Type | Image |
|---|---|---|
| Jurkat | Human Leukemia | 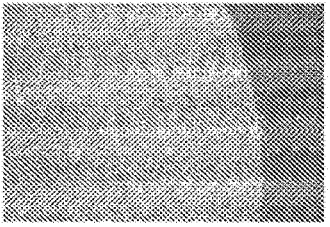 |
| U266 | Human Lymphoma |  |
| Red Blood Cell | Human Erythrocyte | 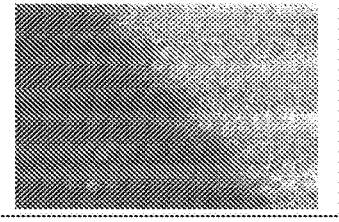 |
| Hela | Human Cervical Cancer | 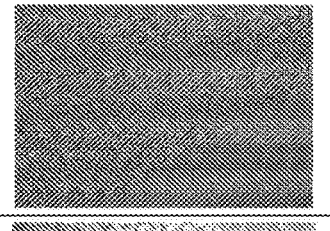 |
| CHO | Chinese Hamster Ovary cells | 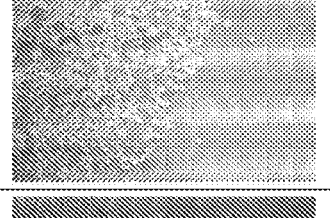 |
| HEK293T | Human Embryonic Kidney cells | 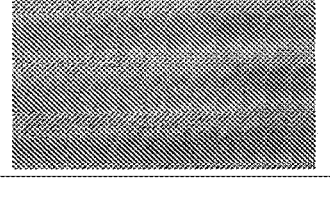 |

Figure 31B

| Cell Name | Cell Type | Image |
|---|---|---|
| MCF7 | Human Breast Cancer | |
| MDA-MB-231 | Human Breast Cancer | |
| Myoblast | Mouse Myoblasts | |
| Myotube | Mouse Myotubes | |

Figure 32A
| Cell | Cell Type | Image |
|---|---|---|
| Chlamydomonas reinhardtii | Algae | 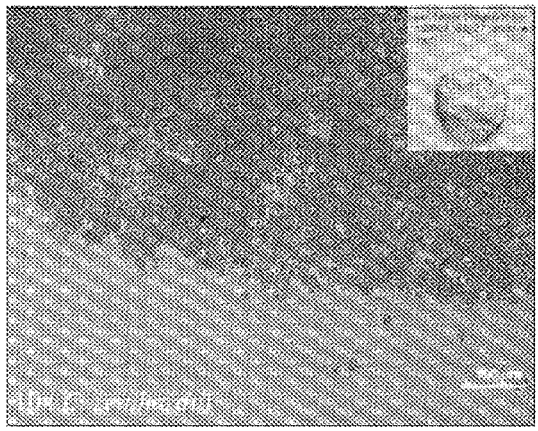 |
| Synechocystic PCC6803 | Gram (-) cyanobacteria | 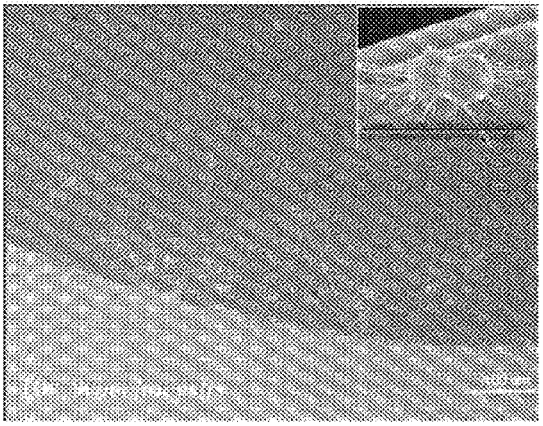 |

Figure 32B
| Cell | Cell Type | Image |
|---|---|---|
| Rhodospirillum rubrum | Gram (-) purple bacteria | 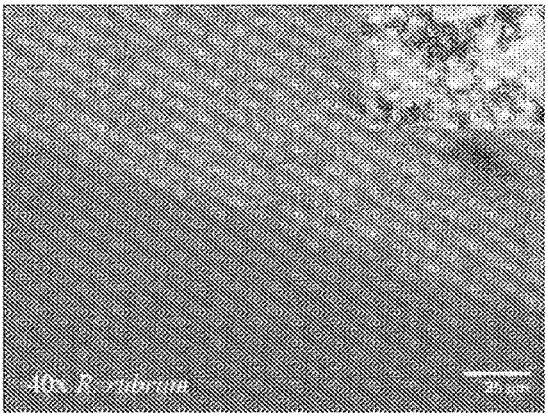 |
| Azotobacter vinlandii | Gram (-) diazotroph | 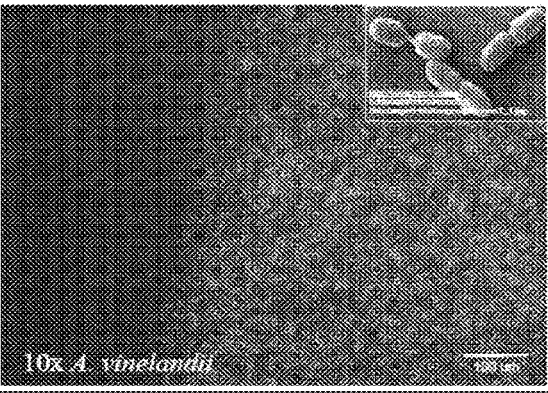 |
| Escherichia coli | Gram (-) enteric bacteria | 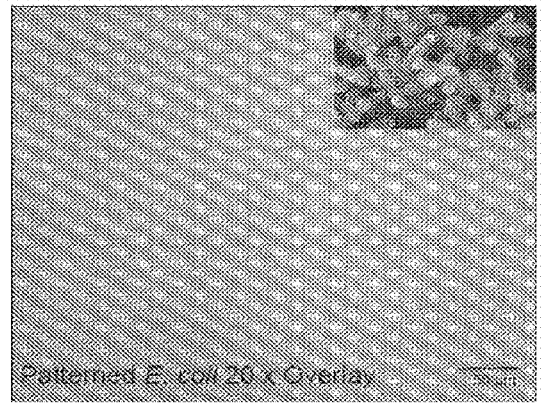 |

Figure 32C
| Cell | Cell Type | Image |
|---|---|---|
| Saccharomyces cerevisiae | Fungi | 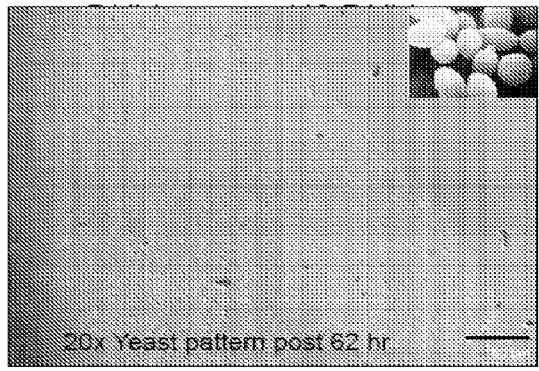 |
| Methanococcus jannaschii | Archaea | 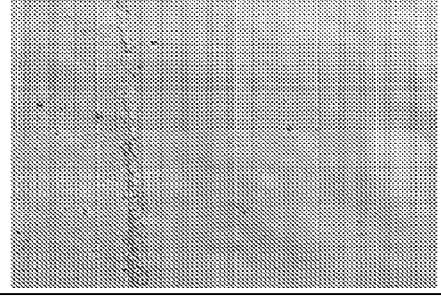 |
| Dictyostelium | Amoeba | 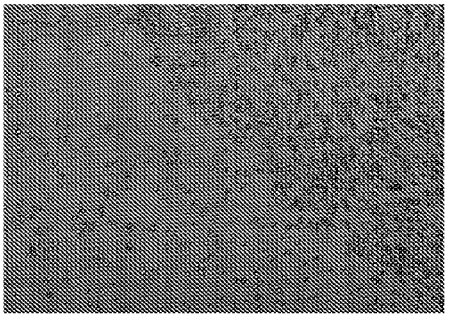 |

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: synthetic complementary oligonucleotide C1

<400> SEQUENCE: 1
gtaacgatcc agctgtcact                                          20

<210> SEQ ID NO 2
<211> LENGTH: 20
<212> TYPE: DNA
<213> ORGANISM: Artificial Sequence
<220> FEATURE:
<223> OTHER INFORMATION: synthetic complementary oligonucleotide M1

<400> SEQUENCE: 2
agtgacagct ggatcgttac                                          20

<210> SEQ ID NO 3
<211> LENGTH: 20
<212> TYPE: DNA
<213> ORGANISM: Artificial Sequence
<220> FEATURE:
<223> OTHER INFORMATION: synthetic complementary oligonucleotide C2

<400> SEQUENCE: 3
tcatacgact cactctaggg                                          20

<210> SEQ ID NO 4
<211> LENGTH: 20
<212> TYPE: DNA
<213> ORGANISM: Artificial Sequence
<220> FEATURE:
<223> OTHER INFORMATION: synthetic complementary oligonucleotide M2

<400> SEQUENCE: 4
ccctagagtg agtcgtatga                                          20

```
<210> SEQ ID NO 5
<211> LENGTH: 20
<212> TYPE: DNA
<213> ORGANISM: Artificial Sequence
<220> FEATURE:
<223> OTHER INFORMATION: synthetic complementary oligonucleotide C3

<400> SEQUENCE: 5
actgactgac tgactgactg                                                      20

<210> SEQ ID NO 6
<211> LENGTH: 20
<212> TYPE: DNA
<213> ORGANISM: Artificial Sequence
<220> FEATURE:
<223> OTHER INFORMATION: synthetic complementary oligonucleotide M3

<400> SEQUENCE: 6
cagtcagtca gtcagtcagt                                                      20

<210> SEQ ID NO 7
<211> LENGTH: 21
<212> TYPE: DNA
<213> ORGANISM: Artificial Sequence
<220> FEATURE:
<223> OTHER INFORMATION: synthetic DNA oligonucleotide strand A

<400> SEQUENCE: 7
tcatacgact cactctaggg a                                                    21

<210> SEQ ID NO 8
<211> LENGTH: 41
<212> TYPE: DNA
<213> ORGANISM: Artificial Sequence
<220> FEATURE:
<223> OTHER INFORMATION: synthetic DNA oligonucleotide strand B (sgc8c)

<400> SEQUENCE: 8
atctaactgc tgcgccgccg ggaaaatact gtacggttag a                              41

<210> SEQ ID NO 9
<211> LENGTH: 41
<212> TYPE: DNA
<213> ORGANISM: Artificial Sequence
<220> FEATURE:
<223> OTHER INFORMATION: synthetic DNA oligonucleotide strand C
      randomized sequence

<400> SEQUENCE: 9
ccctagagtg agtcgtatga ccctagagtg agtcgtatga a                              41

<210> SEQ ID NO 10
<211> LENGTH: 41
<212> TYPE: DNA
<213> ORGANISM: Artificial Sequence
<220> FEATURE:
<223> OTHER INFORMATION: synthetic cell-specific aptamer modified with
      a phenylene diamine group
<220> FEATURE:
<221> NAME/KEY: modified_base
<222> LOCATION: (1)...(1)
<223> OTHER INFORMATION: a modified by phenylene diamine group

<400> SEQUENCE: 10
atctaactgc tgcgccgccg ggaaaatact gtacggttag a                              41
```

<210> SEQ ID NO 11
<211> LENGTH: 19
<212> TYPE: DNA
<213> ORGANISM: Artificial Sequence
<220> FEATURE:
<223> OTHER INFORMATION: synthetic expected sequence from GAPDH siRNA
      binding

<400> SEQUENCE: 11
aaagttgtca tggatgacc                                                  19

<210> SEQ ID NO 12
<211> LENGTH: 20
<212> TYPE: DNA
<213> ORGANISM: Artificial Sequence
<220> FEATURE:
<223> OTHER INFORMATION: synthetic phosphine-modified ssDNA
<220> FEATURE:
<221> NAME/KEY: modified_base
<222> LOCATION: (1)...(1)
<223> OTHER INFORMATION: g modified by phosphine

<400> SEQUENCE: 12
gtaacgatcc agctgtcact                                                 20

<210> SEQ ID NO 13
<211> LENGTH: 21
<212> TYPE: DNA
<213> ORGANISM: Artificial Sequence
<220> FEATURE:
<223> OTHER INFORMATION: synthetic double-stranded GAPDH siRNA sense
      strand
<220> FEATURE:
<223> OTHER INFORMATION: Description of Combined DNA/RNA
      Molecule:synthetic double-stranded GAPDH siRNA sense strand

<400> SEQUENCE: 13
ggucauccau gacaacuuut t                                               21

<210> SEQ ID NO 14
<211> LENGTH: 20
<212> TYPE: DNA
<213> ORGANISM: Artificial Sequence
<220> FEATURE:
<223> OTHER INFORMATION: synthetic RT-PCR GAPDH forward primer

<400> SEQUENCE: 14
agggctgctt ttaactctgg                                                 20

<210> SEQ ID NO 15
<211> LENGTH: 20
<212> TYPE: DNA
<213> ORGANISM: Artificial Sequence
<220> FEATURE:
<223> OTHER INFORMATION: synthetic RT-PCR GAPDH reverse primer
<220> FEATURE:
<221> NAME/KEY: modified_base
<222> LOCATION: (1)...(1)
<223> OTHER INFORMATION: t modified by FAM

<400> SEQUENCE: 15
ttgattttgg agggatctcg                                                 20

<210> SEQ ID NO 16
<211> LENGTH: 21
<212> TYPE: DNA
<213> ORGANISM: Artificial Sequence
<220> FEATURE:
<223> OTHER INFORMATION: synthetic RT-PCR 18S RNA forward primer

<400> SEQUENCE: 16
cggctaccac atccaaggaa g                                          21

<210> SEQ ID NO 17
<211> LENGTH: 20
<212> TYPE: DNA
<213> ORGANISM: Artificial Sequence
<220> FEATURE:
<223> OTHER INFORMATION: synthetic RT-PCR 18S rRNA reverse primer
<220> FEATURE:
<221> NAME/KEY: modified_base
<222> LOCATION: (1)...(1)
<223> OTHER INFORMATION: c modified by FAM

<400> SEQUENCE: 17
cgctcccaag atccaactac                                            20

<210> SEQ ID NO 18
<211> LENGTH: 20
<212> TYPE: DNA
<213> ORGANISM: Artificial Sequence
<220> FEATURE:
<223> OTHER INFORMATION: synthetic 5'-acrydite-modified GAPDH capture
      probe
<220> FEATURE:
<221> NAME/KEY: modified_base
<222> LOCATION: (1)...(1)
<223> OTHER INFORMATION: a modified by acrydite (Acry)

<400> SEQUENCE: 18
atcccatcac catcttccag                                            20

<210> SEQ ID NO 19
<211> LENGTH: 20
<212> TYPE: DNA
<213> ORGANISM: Artificial Sequence
<220> FEATURE:
<223> OTHER INFORMATION: synthetic 5'-acrydite-modified 18S rRNA
      capture probe
<220> FEATURE:
<221> NAME/KEY: modified_base
<222> LOCATION: (1)...(1)
<223> OTHER INFORMATION: g modified by acrydite (Acry)

<400> SEQUENCE: 19
gcagccgcgg taattccagc                                            20

<210> SEQ ID NO 20
<211> LENGTH: 18
<212> TYPE: DNA
<213> ORGANISM: Artificial Sequence
<220> FEATURE:
<223> OTHER INFORMATION: synthetic deprotected thiol-DNA for reaction
      chamber functionalized with ssDNA
<220> FEATURE:
<221> NAME/KEY: modified_base
<222> LOCATION: (1)...(1)
<223> OTHER INFORMATION: a 5' modified by thiol

<400> SEQUENCE: 20
agtgacagct ggatcgtt                                              18

<210> SEQ ID NO 21
<211> LENGTH: 20
<212> TYPE: DNA
<213> ORGANISM: Artificial Sequence
<220> FEATURE:
<223> OTHER INFORMATION: synthetic complementary sequence Z2

```
<400> SEQUENCE: 21
cacacacaca cacacacaca                                                   20

<210> SEQ ID NO 22
<211> LENGTH: 20
<212> TYPE: DNA
<213> ORGANISM: Artificial Sequence
<220> FEATURE:
<223> OTHER INFORMATION: synthetic complementary sequence zc2

<400> SEQUENCE: 22
tgtgtgtgtg tgtgtgtgtg                                                   20

<210> SEQ ID NO 23
<211> LENGTH: 20
<212> TYPE: DNA
<213> ORGANISM: Artificial Sequence
<220> FEATURE:
<223> OTHER INFORMATION: synthetic complementary oligonucleotide A

<400> SEQUENCE: 23
tcatacgact cactctaggg                                                   20

<210> SEQ ID NO 24
<211> LENGTH: 20
<212> TYPE: DNA
<213> ORGANISM: Artificial Sequence
<220> FEATURE:
<223> OTHER INFORMATION: synthetic complementary oligonucleotide A'

<400> SEQUENCE: 24
ccctagagtg agtcgtatga                                                   20

<210> SEQ ID NO 25
<211> LENGTH: 41
<212> TYPE: DNA
<213> ORGANISM: Artificial Sequence
<220> FEATURE:
<223> OTHER INFORMATION: synthetic forward primer for mutating Cys at
      position 87 of tRNA-synthetase

<400> SEQUENCE: 25
agccgcatgg cgttcgtact tatgtatgga actaaccatt c                           41

<210> SEQ ID NO 26
<211> LENGTH: 41
<212> TYPE: DNA
<213> ORGANISM: Artificial Sequence
<220> FEATURE:
<223> OTHER INFORMATION: synthetic reverse primer for mutating Cys at
      position 87 of tRNA-synthetase

<400> SEQUENCE: 26
gaatggttag ttccatacat aagtacgaac gccatgcggc t                           41
```

DNA-CELL CONJUGATES

CROSS-REFERENCES TO RELATED APPLICATIONS

This application is a divisional of U.S. patent application Ser. No. 13/263,129, filed Feb. 24, 2012, which is the U.S. National Stage of International Application No. PCT/US2010/030397, filed Apr. 8, 2010, which claims priority to U.S. Application No. 61/167,748 filed Apr. 8, 2009, and 61/243,123 filed Sep. 16, 2009, all of which are incorporated herein in their entirety for all purposes.

STATEMENT AS TO RIGHTS TO INVENTIONS MADE UNDER FEDERALLY SPONSORED RESEARCH OR DEVELOPMENT

This invention was made with Government support under Contract No. DE-AC02-05CH11231 awarded by the U.S. Department of Energy and supported by the Nanoscale Science, Engineering, and Technology (NSET) Program of the Department of Energy, and the Office of Science, Office of Basic Energy Sciences, under Grant Nos. HG003329 and R01 GM072700 awarded by the National Institutes of Health, and under a National Institutes of Health Molecular Biophysics Training Grant No. T32GM08295. The Government has certain rights in this invention

REFERENCE TO A "SEQUENCE LISTING," A TABLE, OR A COMPUTER PROGRAM LISTING APPENDIX SUBMITTED ON A COMPACT DISK

This application includes a Sequence Listing as a text file named SEQTXT_077429-008111US-1003079 modified Feb. 26, 2016 and containing 6,732 bytes. The material contained in this text file is incorporated by reference in its entirety for all purposes.

BACKGROUND OF THE INVENTION

Typically, peptides have been used in cell-based arrays to capture cells for study. Surfaces are printed with "RGD" peptides designed to bind integrins on a cell surface, but this system does not work with cells that don't have integrins such as non-adherent cells (e.g. leukocytes, lymphocytes) and does not allow controlled defined patterning with different cell types together in the same platform. The RGD system has the large disadvantage of initiating cell differentiation, thus changing the cell before it is analyzed, because integrins are the receptors that are involved in controlling differentiation and also activities that follow after integrin binding that relate to differentiation. (See Du, X. P. et al., Cell 1991, 65, 409-416; Xiong, J. P. et al., Science 2002, 296, 151-155.)

Indirect noncovalent attachment is demonstrated with a protein-protein attachment system in which DNA is indirectly attached to cells by a noncovalent linkage through an antibody-ligand interaction. (Bailey R C et al. J Am Chem Soc. 2007 February 21; 129(7):1959-67) An antibody specific for a target ligand on a cell is conjugated to DNA. The noncovalent linkage between the antibody and the ligand is based on hydrogen bonding, typical of protein-protein interactions. Single-stranded DNA (ssDNA) oligomers on antibodies specific for cell-surface ligands are attached to cells having those ligands, and the cells are in turn anchored to surfaces having ssDNA complementary oligomers that bind the partner strand on the cell to capture the cell.

Indirect covalent attachment of synthetic single-stranded DNA (ssDNA) strands to the surfaces of living cells was first shown using metabolic oligosaccharide engineering by Chandra, R. A. et al. Angew. Chem.-Int. Edit. 2006, 45, 896-901. The indirect covalency was through specific chemical handles (azides) that were introduced in cell surface sialic acids obtained after treating the cells with peracetylated N-azidoacetylmannosamine (Ac4ManNAz) (taking 3 days) prior to the introduction of the DNA. Phosphine-ssDNA conjugates were then covalently attached to the azide handle to form an amide bond (a Staudinger ligation reaction, E. Saxon, et al. Science 2000, 287) between the azido-sugar and the DNA. Azides installed within cell surface glycoconjugates by metabolism of a synthetic azidosugar can be reacted with a biotinylated triarylphosphine to produce many stable cell-surface adducts. However, the covalent metabolic approach takes multiple days to prepare the cells for DNA attachment, and altering the cell surface sugars has metabolic effects on the cell that changes it before one gets a chance to analyze it. It is further limited to certain mammalian cells that possess sialic acid on their surface, and thus cannot be used for bacteria, plant cells, fungi, or many other animal cells.

Noncovalent attachment via antibodies and ligands at the cell surfaces will also activate the cells and thus perturb the cell before analysis can start, also tending to be weaker and "reversible" compared with a covalent attachment. In addition the antibody mechanism requires prevalence of ligand on the cell, and engineering an antibody specific for the ligand to affix sufficient DNA on the cell surface.

Noncovalent attachments via ligand interactions with an antibody at the cell-surface have been made where the antibody carries a strand of protein binding DNA. (Bailey R C et al. J Am Chem Soc. 2007 February 21; 129(7):1959-67). Both methods have the immediate disadvantage of activating the cell they seek to capture for study, thus transforming the thing of interest into something different before it can be analyzed. Overcoming the drawbacks in these early systems of DNA attachment on cell surfaces could transform this just described nacent field and offer valuable tools and manipulations previously not possible.

BRIEF SUMMARY OF THE INVENTION

In one embodiment, the present invention provides a composition having a cell, wherein the cell has a surface including a native functional group, and wherein the cell has no cell wall. The composition also includes a nucleic acid moiety, wherein the nucleic acid moiety is covalently linked to the native functional group.

In another embodiment, the present invention provides a method of preparing a conjugate of a cell and a nucleic acid moiety by contacting the cell with an activated nucleic acid moiety, wherein the cell has a surface including a native functional group, and wherein the cell has no cell wall, such that the nucleic acid moiety is covalently linked to the native functional group.

In another embodiment, the present invention provides a composition having a cell, wherein the cell has a cell wall, and a nucleic acid moiety, wherein the nucleic acid moiety is covalently linked to the cell.

In another embodiments, the present invention provides a method of preparing a conjugate of a cell and a nucleic acid moiety, by contacting the cell with an activated nucleic acid moiety, wherein the cell includes a cell wall, such that the nucleic acid moiety is linked to the cell.

In another embodiment, the present invention provides a device including a cell having a cell surface of a native functional group covalently linked to a first nucleic acid moiety, and a substrate surface having a second nucleic acid moiety complementary to the first nucleic acid moiety, such that the cell is bound to the substrate surface via formation of a nucleic acid duplex of the first and second nucleic acid moieties.

Figure 23:
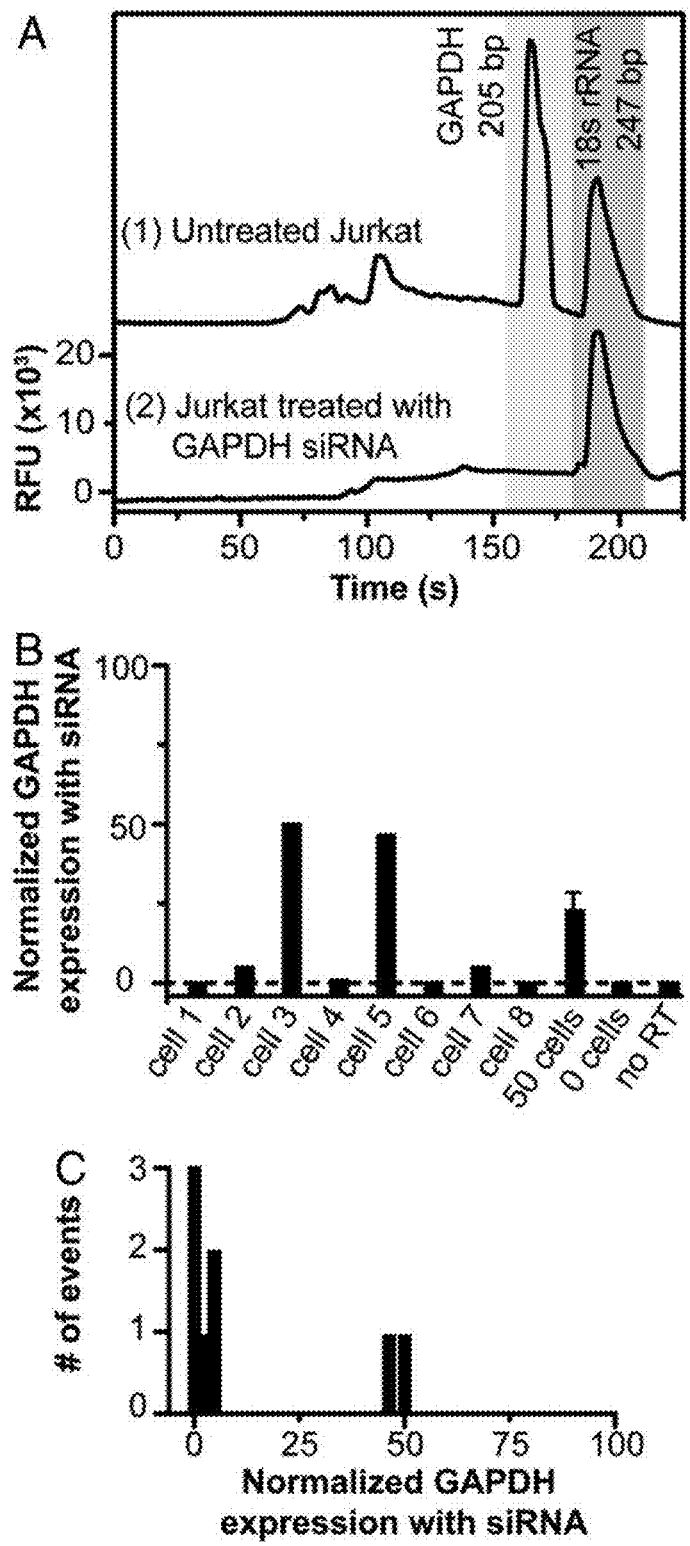

Fluorescently labeled amplicons are detected by confocal fluorescence to determine their amount and identity FIG. 23. Gene expression and silencing at the single-cell level. (A) Representative gene expression electropherograms from individual Jurkat cells. A single wild-type cell with primers targeting GAPDH (200 bp) and 18S rRNA (247 bp) generates 2 strong peaks migrating at 160 s and 185 s, respectively. A single cell electroporated with siRNA directed at GAPDH mRNA shows only a single peak for 18S rRNA. (B) Gene expression of GAPDH for Jurkat cells treated with GAPDH siRNA relative to normal untreated cells. GAPDH expression has been normalized to a control 18S rRNA for comparison. Experiments from 8 individual cells show GAPDH mRNA levels at 0, 5, 50, 1, 48, 0, 5, and 0% of normally untreated Jurkat cells. However, a representative bulk measurement from 50 cells shows GAPDH expression at 21±4%. When no cell is captured on the pad there is no amplification. Similarly, a PCR control with no reverse transcriptase shows no amplification. (C) Histogram of the number of events for siRNA treated cells shows that there are 2 distinct populations of cells whose expression levels are very distinct from the population average FIG. 24. Dual-surface modification of capsides for targeted delivery is shown. For interior surface modification, an N87C mutation of the MS2 coat protein allows for site specific alkylation. Up to 180 cargo molecules can be installed in these locations. For exterior surface modification, the aptamer (SEQ ID NO:10) is first modified with a phenylene diamine group. A T19paF mutation on the capsid allows for the attachment of the modified DNA to the exterior surface of MS2 by $NaIO_4$ mediated oxidative coupling reaction.

Figure 25:
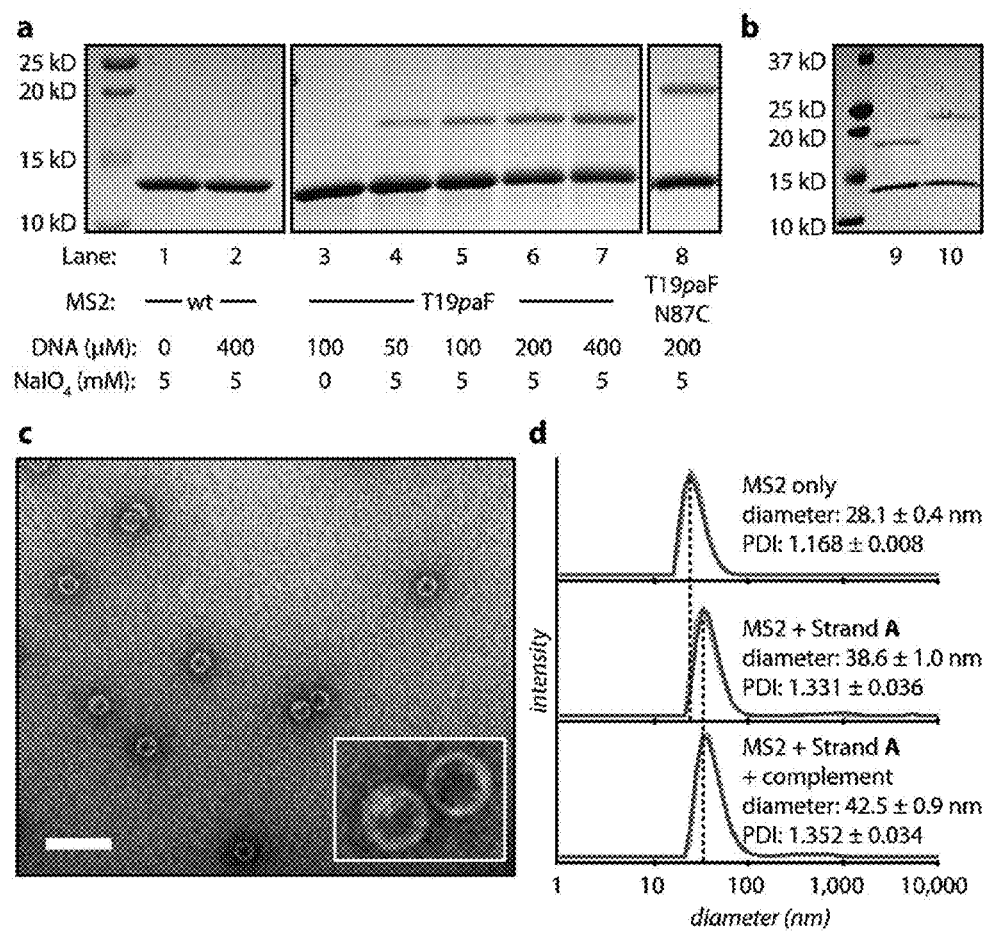

FIG. 25. Analysis of DNA attachment to the exterior surface of MS2. (a) MS2-DNA conjugates were analyzed by SDS-PAGE followed by Coomassie staining. Lanes 1-7 were reacted with strand A. Lane 8 shows the reaction with strand B. (b) a gel-shift assay confirmed DNA competency for base-pairing after conjugation to MS2. Lane 10 includes the complementary sequence to strand A with an additional 20 adenine bases for increased electrophoretic shift, while lane 9 has not additional DNA added. Transmission electron micrograph images (c) and dynamic light scattering analysis (d) showed intact capsides after DNA conjugation. In addition, DLS showed a significant increase in diameter upon conjugation of strand A, as well as an additional increase in diameter upon addition of the 20-base complementary sequence to strand A (without the additional 20-base overhang). The scale in the TEM image represents 100 nm.

Figure 26:
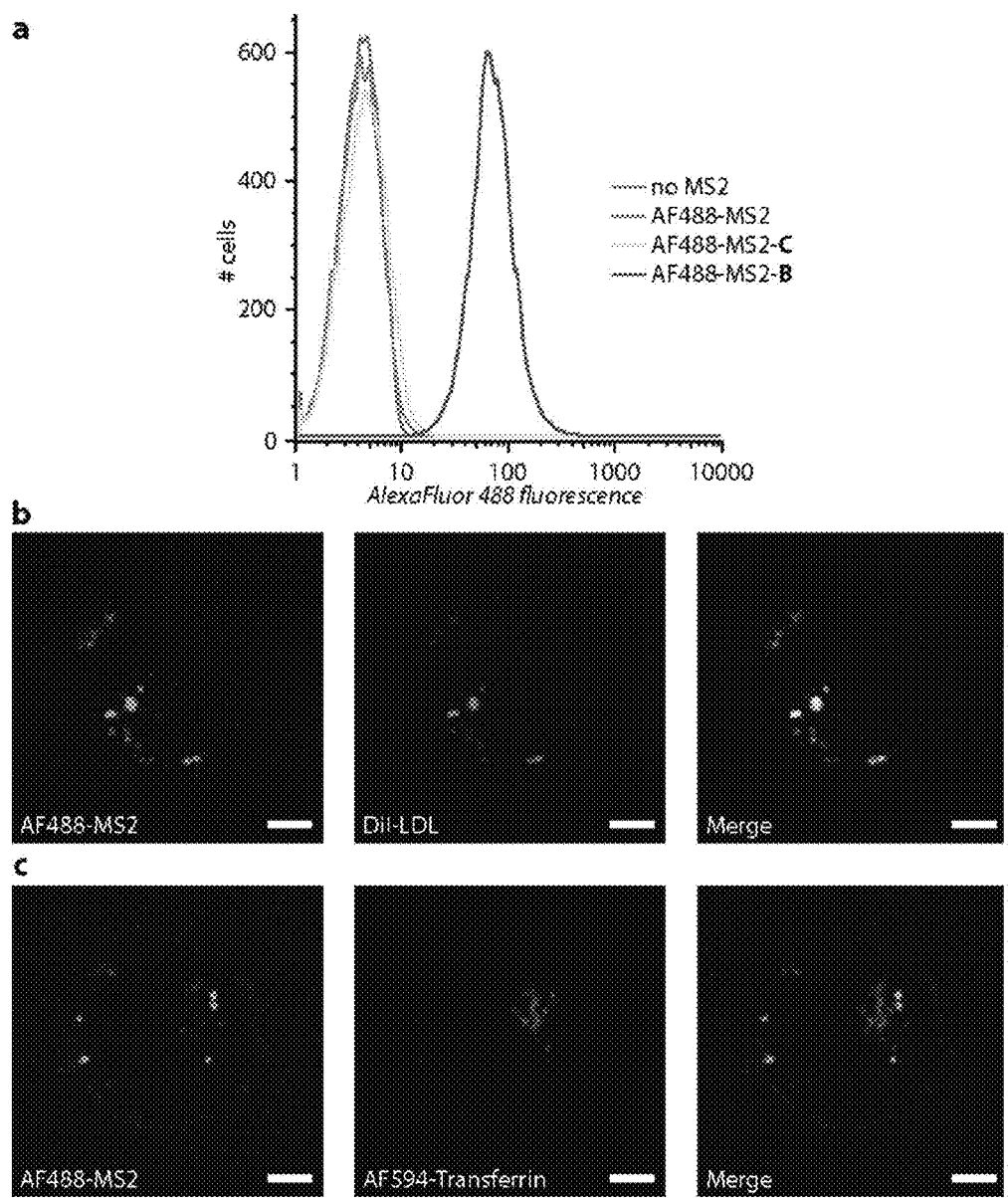

FIG. 26. Cellular targeting and uptake with aptamer-labeled capsids (a) cell targeting was confirmed using flow cytometry. Only MS2 capsids modified with strand B bound to Jurkat cells (blue). Capsids that were unmodified on the exterior and capsids modified with strand C (green and yellow respectively) show a colocalization of B-labeled capsides with LDL-labeled endosomes (b), but not with transferrin-labelled endosomes (c). Scale bars represent 3 µm.

Figure 27:
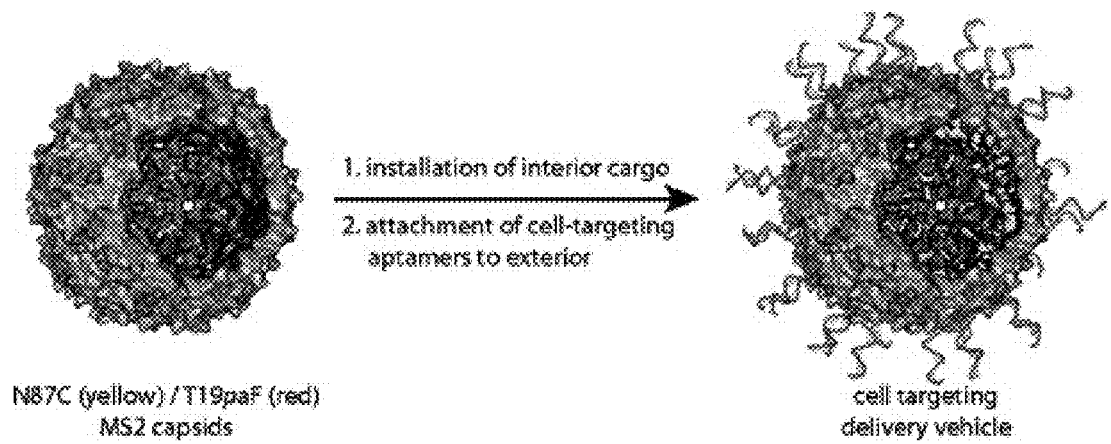

FIG. 27 shows installation of interior cargo attachment of cell-targeting aptamers to viral exterior. The schematic depicts the basic process involving the virus: the virus is coated with an oligonucleotide aptamer at a carbohydrate, the virus contains cargo (up to 180 molecules); by virtue of the aptamer specificity for a cell surface protein on the surface of a live target cell, the aptamer binds the receptor protein and internalizes or otherwise delivers its contents to that cell.

Figure 28A:
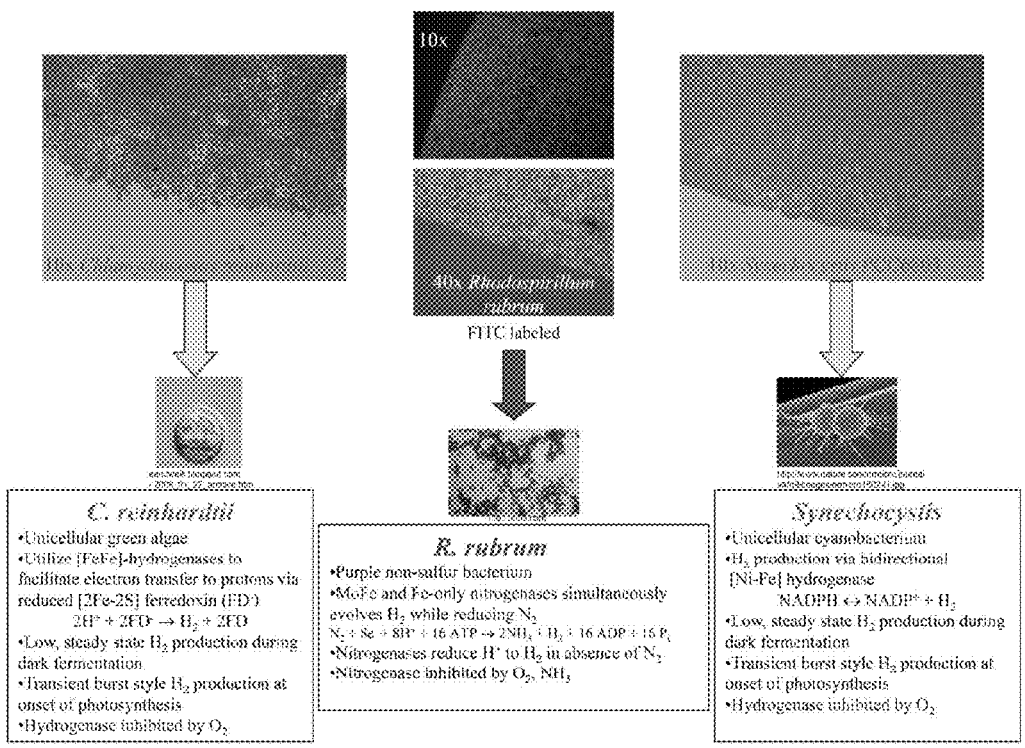

FIG. 28 shows images of cells which have been patterned using the present methods and a short explanation of the organism's role in a synergistic solar powered H2 fuel cell (on a chip). FIG. 28A shows *Synechocystis* PCC6803 (cyanobacteria), *C. reinhardtii* (algae), *R. rubrum*, and FIG. 28B shows *A. vinelandii*. The cells are patterned on large spots of ssDNA, which is why only a partial curvature to the pattern is shown in the images.

FIG. 29 shows images of *E. coli* patterns (A) shows patterned *E. coli* 20× labeled with FITC DIC overlay; (B) and (C) show images of patterned *E. coli* (not fluorescently labeled) and *Synechocystis* (labeled with FITC)) microarray pattern 20× (top) and 10× (bottom). There is background fluorescence but the cells are denotable by their texture.

Figure 30:
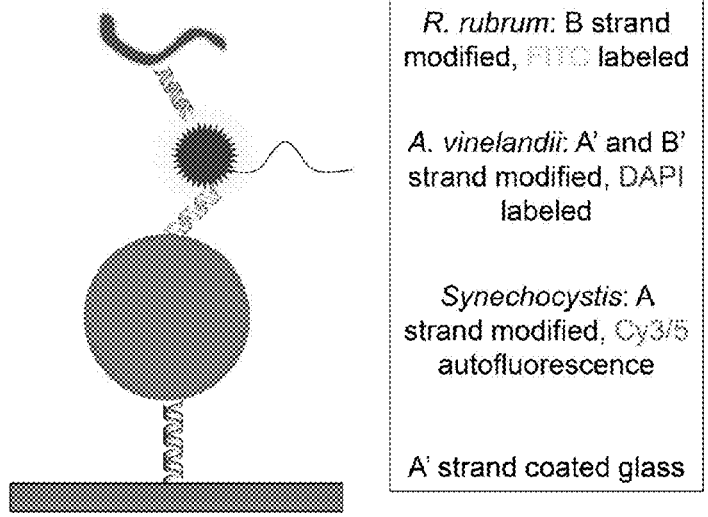

FIG. 30 shows a schematic of *Synechocystis* PCC6803 (cyanobacteria), *A. vinelandii*, and *R. rubrum* patterned layers on a glass substrate for use in a fuel cell device.

FIGS. 31A and 31B show the DNA-cell conjugates of mammalian cells prepared by the present invention by reaction with a lysine native functional group on the cell surface, and immobilized on a glass microscope slide modified with the complementary DNA strand, demonstrating formation of the DNA cell conjugate.

FIGS. 32A, 32B and 32C show the DNA-cell conjugates of non-mammalian cells prepared by the present invention immobilized on a glass microscope slide modified with the complementary DNA strand, demonstrating formation of the DNA-cell conjugate.

Figure 33:
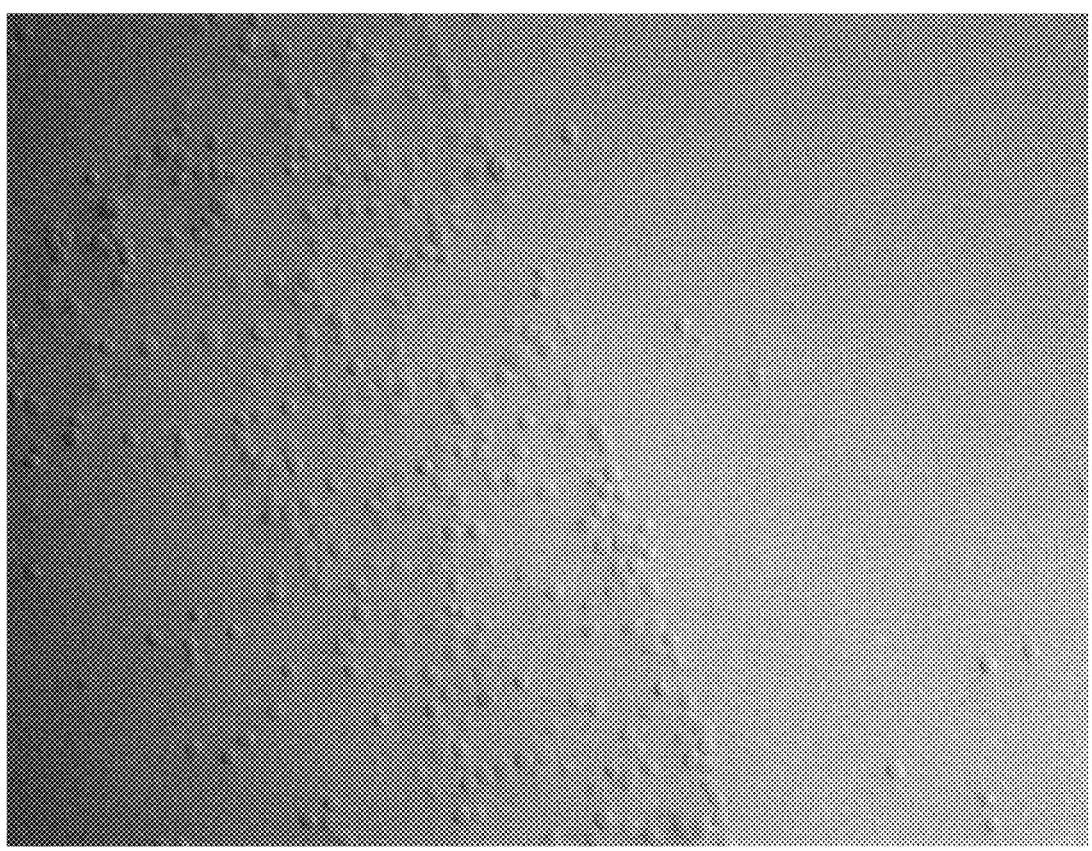

FIG. 33 shows the DNA-cell conjugates of mammalian cells prepared by the present invention by reaction with an aspartic acid or glutamic acid native functional group on the cell surface, and immobilized on a glass microscope slide modified with the complementary DNA strand, demonstrating formation of the DNA-cell conjugate.

DETAILED DESCRIPTION OF THE INVENTION

I. General

The present invention provides the first example of a cell-DNA conjugate prepared by covalently linking the DNA to the cell via a native functional group on the cell surface, without the need for metabolic engineering. For mammalian cells and other cells without cell walls, the DNA is covalently linked directly to the amino acids on the surface of the cell, such as the lysine amines. For plant cells and other cells with cell walls, the sugars on the surface of the cell are first modified, such as by oxidation to form an aldehyde or ketone, and then modified with the DNA.

Previous methods of forming DNA-cell conjugates required the use of metabolic engineering, i.e., feeding a cell with an appropriately modified sugar, such as an azide functionalized sugar, that was metabolised by the cell and expressed on the cell surface. The DNA was then conjugated to the azide modified sugar. This method has several drawbacks limiting both the utility and scope of application. For example, the metabolic engineering requires several days to afford a cell with a sufficient amount of azide functionalized sugar on the cell surface. The type of cells that can be modified is also limited, excluding primary cells which have important diagnostic utility. Finally, the metabolic engineering necessarily modifies the structure and properties of the cell.

The present invention overcomes the difficulties inherent to the azide metabolic engineering process by using the native functional groups already present on the cell surface.

Using an activated DNA sequence, such as DNA modified with an NHS-ester, the DNA can be covalently linked to the amine of a lysine group on the cell surface of a cell without a cell wall. This process takes several hours at most. The simplicity of the process allows modification of primary cells, as well as stem cells. For cells with cell walls, the native sugars on the cell surface are first modified, such as by oxidation to form aldehydes and ketones that are then reacted with an activated DNA sequence, such as with an aminooxy group. The DNA-cell conjugates and methods of the present invention represent a substantial leap forward in cell detection and assay methods.

The ability to pattern cells on surfaces provides a new platform for various studies and applications, e.g., the study of cell biology, the control of stem cell differentiation, and the engineering of new tissues. Typically, cell-based arrays are formed by printing surfaces of interest with "RGD" peptides that are designed to bind to integrins on the cell surface. While this approach has been widely adopted for the immobilization of many cell types, it cannot be used to capture non-adherent cells (such as leukocytes) or to bind multiple cell types to unique array features. It also can cause undesired changes in cell differentiation or behavior because it engages the very surface receptors that are involved in controlling these processes.

To circumvent these limitations, the capture of live cells through the hybridization of synthetic DNA strands covalently linked to their plasma membranes to surfaces printed with complementary sequences has been previously reported by some of the inventors in Chandra, R. A.; Douglas, E. S.; Mathies, R. A.; Bertozzi, C. R.; Francis, M. B. *Angew. Chem.-Int. Edit.* 2006, 45, 896-901, hereby incorporated by reference. In addition to allowing multiple cell types to be patterned on a single substrate, the method offered the important advantages of substrate reuse and tunability. Most importantly, this approach has been used to capture non-adherent cells in addition to adherent ones, and it has been shown that the cells experience minimal changes in behavior as a result of immobilization through this receptor-independent process. In previous reports, the utility of this method has also been shown for the formation of complex cell patterns.

The DNA strands used in previous studies were installed into cell surface glycans through a two-step process. First, the cells were fed with an azide-containing mannose derivative for 1-3 days. This sugar was subsequently metabolized and incorporated into sialic acid-containing cell surface glycans. The DNA was then targeted to the azide functionality using a Staudinger ligation. While effective, this protocol is most appropriate for cultured mammalian cell lines, as it requires multiple days of exposure to install a sufficient number of azide groups.

Figure 1:
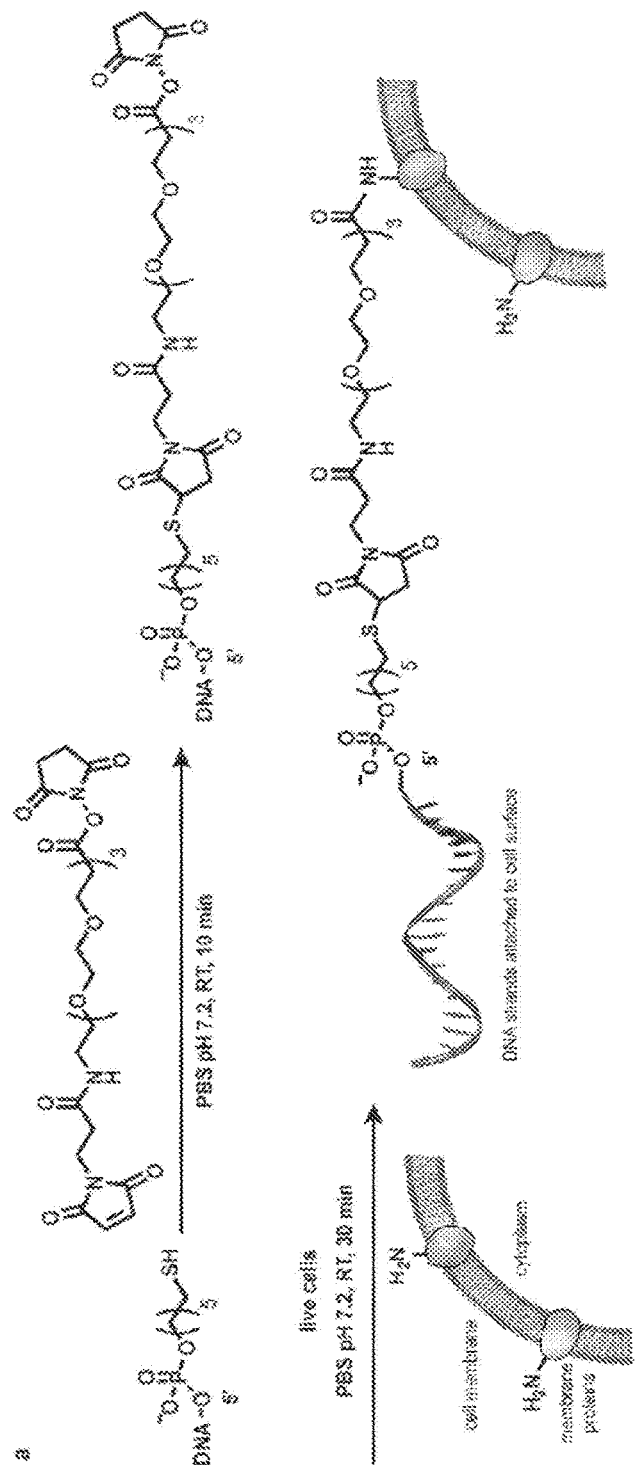
FIG. 1. Covalent attachment of ssDNA to cell surfaces. (a) Thiolated single-stranded DNA was first reacted with NHS-PEG-Maleimide in PBS at room temperature to form the NHS-DNA conjugate. This solution was then incubated with suspensions of live cells in PBS at room temperature for 30 mins. After attachment of the DNA strands, the cells were returned to culture media. (b,c) Jurkat cells were exposed to NHS-DNA solutions of varying concentrations as described in (a). The fluorescent strand complement was then added, and the level of cell modification was quantified using flow cytometry. Up to 120,000 DNA strands could be installed on each cell. (d) A schematic of a method for patterning cells onto a surface.
Figure 1:
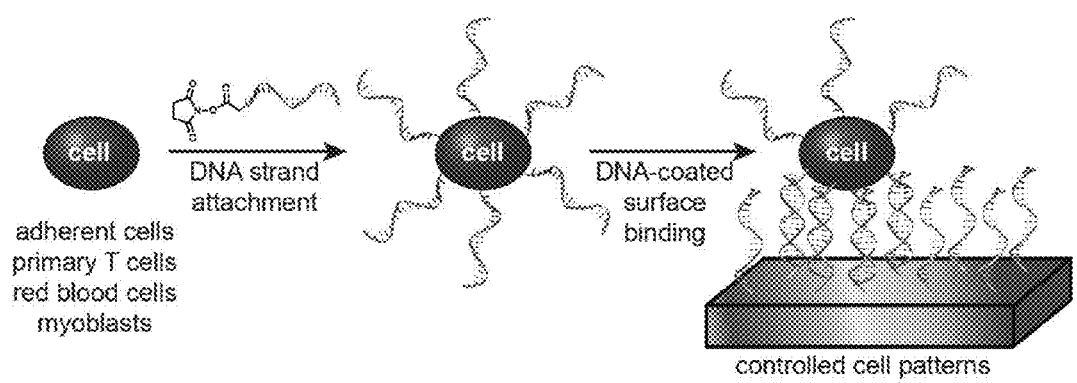
Figure 2:
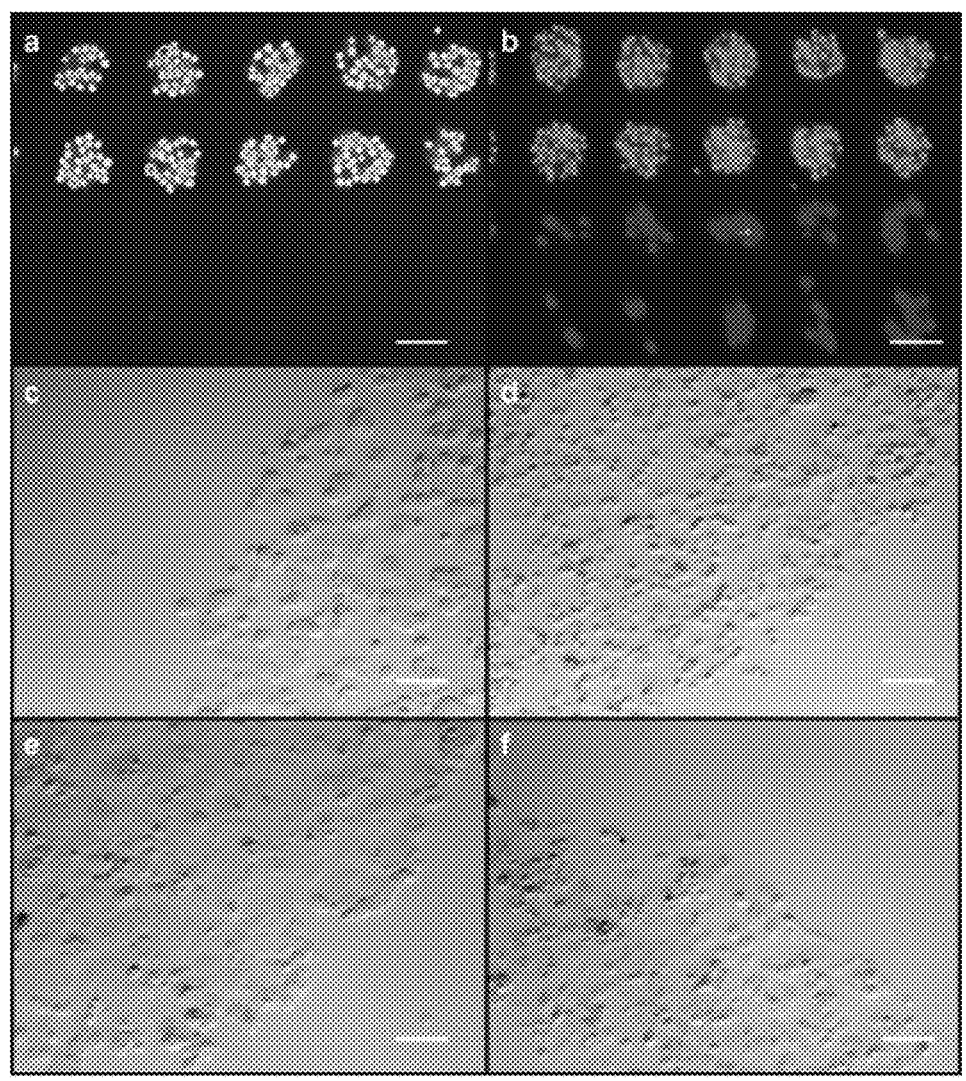
FIG. 2. Immobilization of cells in a DNA sequence-specific manner. (a) Cells bearing DNA sequence C2 bound to complementary (sequence M2) spots on a DNA microarray (spot size=60 μm). Neighboring spots with non-complementary sequence M1 remained unoccupied. (b) The same microarray substrate was exposed to a mixed suspension of Jurkat and MDA cells bearing sequences C2 and C1, respectively. Jurkat cells were stained with Cell-Tracker Green, and MDA cells were stained with Cell-tracker Blue. (c) MCF-7 and (d) MDA cells also bound to DNA coated surfaces in a rapid, stable, and sequence-specific manner. Clear delineation between the DNA-coated and uncoated regions was observed. Phase contrast images are shown after 2 h of incubation. (e) MCF-7 and (f) MDA cells had spread and proliferated after 36 h, but were still confined to the DNA-printed area.

To expand the generality of the DNA-based adhesion method, the present invention provides an improved method for the direct installation of nucleic acids onto virtually any cell surface. Referring now to FIG. 1, in one embodiment, an activated or functionalized single-stranded nucleic acid is first reacted with chemical linker in a buffer solution to form a nucleic-acid-linker conjugate. The cell or cell surface is exposed to the buffer solution for a specified period of time to allow the reaction to proceed to attach the nucleic acid via the chemical linker to a cell surface. After attachment of the nucleic acid to the cells, the cells are returned to culture media. Varying concentrations of the nucleic acid can be used as described and quantified in FIG. 1a. In one example, an oligonucleotide is reacted with a chemical linker in a neutral buffer solution to conjugate the oligonucleotide to the chemical linker, then the cells are incubated with the buffer solution containing the oligonucleotide-linker conjugate for 30 minutes to allow modification and attachment of the oligonucleotide-linker conjugate to the cell's surface.

The cell modification typically proceeds through the formation of a covalent bond between the linker and an amino acid on the cell surface. In some embodiments, the cell surface may be the cell membrane of live cells from any origin, including animal, plant, algae, or bacterial cells. In some embodiments, the covalent bond is an amide bond or an ester bond. In some embodiments, the oligonucleotide is single-stranded. In other embodiments, the amino acid is selected from lysine, cysteine, tyrosine, serine, aspartate, glutamate and tryptophan.

In cells such as plant cell with cell walls, the linkage can be a hydrazone, an oxime, or an amine, among others, wherein said attachment occurs through periodate oxidation followed by hydrazone, oxime or amine formation. In one embodiment, a carbohydrate on the cell undergoes oxidation to generate an aldehyde function group, then the aldehyde is reacted with the oligonucleotide-linker conjugate for direct cell modification of the plant cell surface.

This procedure can be carried out in some embodiments in less than 1 hour, and leads to equivalent levels of cell surface functionalization with any oligonucleotide sequence of interest. The present method can be applied to various embodiments including, the capture of single cells for RT-PCR analysis, the attachment of living cells to a solid substrate for force measurement or cell patterning techniques. In the examples, we demonstrate the use of this new labeling method for the capture of red blood cells, primary T-cells, and myoblasts, which are all types of cells that are difficult to pattern using other methods. This new technique greatly expands the scope of the DNA-based adhesion strategy and is sufficiently straightforward to be used in labs that do not specialize in organic synthesis.

Thus, in one embodiment, the invention is a composition including a cell membrane with an oligonucleotide directly covalently attached. The cell membrane can be a whole intact cell, whereby the composition comprising a whole cell with an oligonucleotide directly covalently attached. Multiple oligonucleotides can be attached to a single cell. The cell can be a live cell. The cell can be any cell, such as a eukaryotic cell, including an animal cell or a non-animal cell. That the cell or cell membrane is modified "directly" means that the cell membrane (cell surface, outside of the cell) is not modified or changed before the attachment of the oligonucleotide. Specifically, because the attachment is to a constituent on the cell surface, directly means that the constituent to which the oligonucleotide attaches is not modified before the covalent attachment with the oligonucleotide. Previous methods all modify a moiety on the cell surface first, before attaching the oligonucleotide.

By covalent attachment it is meant that a new covalent bond is formed between the two molecules that connect to each other. The bonds are typically an amide or an ester bond, but can be any bond that serves the purpose of attachment between the oligonucleotide and a moiety on the cell surface (such as a protein, amino acid, or carbohydrate, or other cell surface entity).

One embodiment facilitates the direct modification of cell surfaces with NHS-DNA conjugates in a rapid and efficient process, allowing virtually any mammalian cell to be patterned on surfaces bearing complementary DNA in under 1 hour. The specific technique described here demonstrates an ability to use several types of cells that are generally incompatible with previous integrin-targeting techniques, including red blood cells, primary T-cells, and myoblasts. The immobilization procedure did not activate primary T-cells, in contrast to previously reported antibody- and lectin-based methods. In these studies, myoblast cells were patterned with high efficiency and remained undifferentiated after surface attachment. Upon changing to differentiation media, myotubes formed in the center of the patterned areas with an excellent degree of edge alignment. The availability of this new protocol greatly expands the applicability of the DNA-based attachment strategy for the generation of artificial tissues and the incorporation of living cells into device settings.

II. Definitions

"Cell" refers to the basic functional unit of life, and includes both prokaryotic and eukaryotic cells. Cells are characterized by an interior having the nucleus or nucleoid, and a cell membrane (cell surface). Cells can also have a cell wall. Cells without a cell wall include eukaryotic cells, mammalian cells, and stem cells. Cells with a cell wall include prokaryotic cells and plant cells. Other cells are useful in the present invention.

"Native functional group" refers to the functional groups that are native to the surface of a cell, such as amino acids and sugars, and that react with the nucleic acid moiety to form the conjugates of the present invention. Exemplary amino acids include lysine, cysteine, tyrosine, threonine, serine, aspartic acid, glutamic acid and tryptophan. Other amino acids are useful, such as those described below. Sugars are also native to cell surfaces, and include mannose, galactose and sialic acid, as well as those described below. The native functional groups can react with the nucleic acid moieties in an unmodified form, or can be modified to make them more reactive.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

"Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

"Unnatural amino acids" are not encoded by the genetic code and can, but do not necessarily have the same basic structure as a naturally occurring amino acid. Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethyl asparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid, thioproline, aminophenylalanine, hydroxytyrosine, and aminotyrosine.

"Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid (i.e., hydrophobic, hydrophilic, positively charged, neutral, negatively charged). Exemplified hydrophobic amino acids include valine, leucine, isoleucine, methionine, phenylalanine, and tryptophan. Exemplified aromatic amino acids include phenylalanine, tyrosine and tryptophan. Exemplified aliphatic amino acids include serine and threonine. Exemplified basic aminoacids include lysine, arginine and histidine. Exemplified amino acids with carboxylate side-chains include aspartate and glutamate. Exemplified amino acids with carboxamide side chains include asparagines and glutamine. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Sugar" refers to a saccharide, such as a monosaccharide, a disaccharide, an oligosaccharide or a polysaccharide. Monosaccharides include, but are not limited to, glucose, ribose, fructose, sialic acid, mannose and galactose. Disaccharides include, but are not limited to, sucrose and lactose. Polysaccharides include, but are not limited to, cellulose, hemicellulose and lignocellulose or starch. Other saccharides are useful in the present invention.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Nucleic acid moiety" refers to a group containing a plurality of nucleotides or nucleic acids. Exemplary nucleic acid moieties include, but are not limited to, an oligonucleotide, deoxy-ribonucleic acid (DNA), ribonucleic acid (RNA), peptide nucleic acid (PNA), Morpholino and locked nucleic acid (LNA), glycol nucleic acid (GNA), threose nucleic acid (TNA), single-stranded DNA (ssDNA), 2'-fluorodeoxy ribonucleic acid, aptamer, and others.

"Activated nucleic acid moiety" refers to a nucleic acid moiety have a group having increased reactivity with one or more native functional groups. For example, when the native functional group is an amine on lysine, the activated group can be an activated ester such as an N-hydroxysuccinimide ester (NHS-ester). The activated ester can be linked directly to the nucleic acid portion of the activated nucleic acid moiety, or linked via a linker. When the native functional group is cysteine, the activated group can be a maleimide. Other activated esters and activated groups are useful for the activated nucleic acid moiety. Tyrosines can be modified using diazonium salts, imines, and allyl-palladium species. Tryptophans can be modified using metallocarbenoids and imines. N-terminal amino acids can be modified through transamination, and N-terminal serines and threonines can be oxidized to yield aldehydes using sodium periodate.

"Modified native functional group" refers to a native functional group modified to bind the nucleic acid moiety to the cell surface. The native functional group can be modified in a variety of methods, except by metabolic engineering. For example, when the native functional is a sugar, the sugar can be oxidized using a suitable modifying agent or oxidizing agent such as sodium periodate. When the native functional group is a sugar, and the modifying agent is an oxidizing agent such as sodium periodate, the modified native functional group can be an aldehyde or ketone.

"Substrate surface" refers any material which can be derivatized to include a nucleic acid moiety. Examples of materials for the substrate surface include, but are not limited to, glass (including controlled-pore glass), polymers (e.g., polystyrene, polyurethane, polystyrene-divinylbenzene copolymer), silicone rubber, quartz, latex, a derivatizable transition metal, magnetic materials, silicon dioxide, silicon nitride, gallium arsenide, and derivatives thereof. Except for the reactive sites on the surface, the materials are generally resistant to the variety of chemical reaction conditions to which they may be subjected.

III. Cell-DNA Conjugates

The present invention provides cell-DNA conjugates and methods of making the conjugates.

A. Conjugates of Cells without Cell Walls

The present invention provides conjugates of nucleic acid moieties and cells without cell walls. The conjugates are formed by covalently linking the nucleic acid moiety to the cell surface via a native functional group on the cell surface. The cells used in the conjugates of the present invention can be any cell, and do not require metabolic engineering to introduce the functional group for conjugating the nucleic acid moiety.

In some embodiments, the present invention provides a conjugate of a cell and a nucleic acid moiety, wherein the cell has a surface including a native functional group, the cell has no cell wall, and the nucleic acid moiety is covalently linked to the native functional group.

Cells useful in the present invention include any type of cell. In some embodiments, the cells are cells without a cell wall. Cells (and cell membranes for the same use) that can be used for nucleic acid moiety attachment can be any eukaryotic cell which includes all animal cells, plants cells, algae cells, bacterial cells and fungal cells. The following is a non-exhaustive list of cells that may be used in the compositions, devices and methods of this invention. The list is intended to include many cells and cell types, but not intended to be limiting of the cells that can be used in the invention. Rather these cells and cell types are exemplary, and illustrative. Both live cells, killed cells, and cell lines may be used in the invention. Live cells are likely to provide the most analytical and useful information, and because live cells can be used in the invention without activating through cell surface modification, they can be studied for their native or near native properties in artificial systems and devices using the tools provided by and inherent to the invention.

The following is a nonlimiting list of cells. Human cell types from blood and immune systems include: lymphoid: B cell, T cell (Cytotoxic T cell, Natural Killer T cell, Regulatory T cell, T helper cell), Natural killer cell myeloid: granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell. The endocrine system includes thyroid (Thyroid epithelial cell, Parafollicular cell), parathyroid (Parathyroid chief cell, Oxyphil cell), adrenal (Chromaffin cell), pineal (Pinealocyte) cells. Cells of the Nervous system are glial cells (Astrocyte, Microglia) Magnocellular neurosecretory cell, Stellate cell, Boettcher cell, and pituitary (Gonadotrope, Corticotrope, Thyrotrope, Somatotrope, Lactotroph). Cells of the Respiratory system include Pneumocyte (Type I pneumocyte, Type II pneumocyte), Clara cell, Goblet cell, Dust cell. Cells of the Circulatory system include Myocardiocyte, Pericyte. Cells of the Digestive system, Include stomach (Gastric chief cell, Parietal cell), Goblet cell, Paneth cell, G cells, D cells, ECL cells, I cells, K cells, S cells. Enteroendocrine cells, Enterochromaffin cell, APUD cell, liver (Hepatocyte, Kupffer cell), Cartilage/bone/muscle. The integumentary system bone: Osteoblast, Osteocyte, Osteoclast, teeth (Cementoblast, Ameloblast) cartilage: Chondroblast, Chondrocyte skin/hair: Trichocyte, Keratinocyte, Melanocyte (Nevus cell), muscle: Myocyte, other: Adipocyte, Fibroblast, Tendon cell. Urinary system includes Podocyte, Juxtaglomerular cell, Intraglomerular mesangial cell/Extraglomerular mesangial cell, Kidney proximal tubule brush border cell, Macula densa cell. The Reproductive system Includes male (Spermatozoon, Sertoli cell, Leydig cell), female (Ovum). Keratinizing epithelial cells include Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, secreting melanocyte-stimulating hormone, Magnocellular neurosecretory cells, secreting oxytocin, secreting vasopressin, Gut and respiratory tract cells, secreting serotonin. secreting endorphin, secreting somatostatin, secreting gastrin, secreting secretin, secreting cholecystokinin, secreting insulin, secreting glucagon, secreting bombesin, Thyroid gland cells, thyroid epithelial cell, parafollicular cell, Parathyroid gland cells, Parathyroid chief cell, Oxyphil cell, Adrenal gland cells, chromaffin cells, secreting steroid hormones (mineralcorticoids and gluco corticoids), Leydig cell of testes secreting testosterone, Theca interna cell of ovarian follicle secreting estrogen, Corpus luteum cell of ruptured ovarian follicle secreting progesterone, Granulosa lutein cells, Theca lutein cells, Juxtaglomerular cell (renin secretion), Macula densa cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells. Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Nervous system, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, or Interstitial kidney cells.

The cells can be healthy cells, or diseased cells. For example the cells can be from a cancer condition such as epithelial cancer or carcinoma, including but not limited to, a, carcinoma of the prostate, carcinoma of the breast, carcinoma of the colon, pancreatic carcinoma, lung carcinoma, skin carcinoma (melanoma), esophageal carcinoma, etc.) or the putative cell of origin (hepatocellular carcinoma, renal cell carcinoma, and small cell lung carcinoma, etc.). Other cancer cells include myoepithelial cancers, sarcomas, gliomas, lymphomas, leukemias, carcinoids, and any other type of cancer. Cells in other states or conditions of tissue may be used including but not limited to, autoimmune conditions, immune system related conditions (e.g. allergies, likely immune response to challenge), cells representative of conditions that contribute to or exhibit resistance to standard treatments, susceptibility or predisposition to a condition (e.g. susceptibility to diabetes, thyroid conditions, stroke, cardiovascular conditions, or liver quality, function, and degeneration, etc.).

In some embodiments, the cell is a primary cell. In other embodiments, the cell is a mammalian cell. In some other embodiments, the cell is a stem cell.

The cell surface can include any suitable native functional group, such as amino acids and sugars. In some embodiments, the native functional group can be an amino acid such as lysine, cysteine, tyrosine, threonine, serine, aspartic acid, glutamic acid or tryptophan. In other embodiments, the native functional group is lysine. In some other embodiments, the native functional group can be an N-terminal serine or threonine.

The nucleic acid moiety can be any suitable nucleic acid moiety having a nucleic acid or nucleotide. Exemplary nucleic acid moieties include, but are not limited to, an oligonucleotide, deoxy-ribonucleic acid (DNA), ribonucleic acid (RNA), peptide nucleic acid (PNA), Morpholino and locked nucleic acid (LNA), glycol nucleic acid (GNA), threose nucleic acid (TNA), single-stranded DNA (ssDNA), aptamer, and others. Other nucleic acid moieties include fluorinated nucleic acids.

In another embodiment, the nucleic acid moieties of the invention are nucleic acids and also polymers of nucleotides. The term "nucleic acid" or "oligonucleotide" can be used interchangeably and are meant to include biopolymers of DNA or RNA nucleotides, including nucleic acids that are single-stranded, double stranded, triple stranded, branched or unbranched, or formed of a ladder of partially hybridizing short oligonucleotides, nucleic acids having secondary structure, and/or naturally occurring or non-naturally occurring nucleotides.

In one embodiment, a single-stranded oligonucleotide provides the opportunity to attach the cell by hybridization to its complementary strand on another cell, a substrate surface, or a device.

The length of the single-stranded oligonucleotide used to attach on the cell surface can range from about 4 nucleotides to about 200 nucleotides. Generally, a length of between about 12 nucleotides and 40 nucleotides is optimal for hybridization. Strands of about 20 to about 25 nucleotides are often used for hybridization purposes.

The number of nucleic acid moieties that are attached to the cell surface can be upwards of about 100,000 per cell. In some embodiments, the number of nucleic acid moieties can be one nucleic acid moiety to about 10,000, or about 30,000, or about 50,000. The number of nucleic acid moieties needed may vary based upon factors such as the application and/or cell type. In FIG. 1b, up to 120,000 DNA strands were shown to be installed on each cell.

In one embodiment, the nucleic acid moiety is an aptamer. Aptamers are oligonucleic acid molecules that can adopt a three-dimensional structure and bind a specific target molecule. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications. DNA or RNA aptamers are short strands of nucleic acid moieties. Aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Aptamer selection includes a nucleic acid-based genetic regulatory element called a riboswitch that possesses similar molecular recognition properties to the artificially made aptamers. This type of aptamer is a new mode of genetic regulation.

A concept of smart aptamers, and smart ligands discovers aptamers with pre-defined equilibrium (Kd), rate (koff, kon) constants and thermodynamic (ΔH, ΔS) parameters of aptamer-target interaction. Kinetic capillary electrophoresis selects the aptamers. Non-modified aptamers are cleared rapidly from the bloodstream, with a half-life of minutes to hours, mainly due to nuclease degradation and clearance from the body by the kidneys, a result of the aptamer's inherently low molecular weight. Unmodified aptamer applications currently focus on treating transient conditions such as blood clotting, or treating organs such as the eye where local delivery is possible. This rapid clearance can be an advantage in applications such as in vivo diagnostic imaging. An example is a tenascin-binding aptamer under development for cancer imaging. Several modifications, such as 2'-fluorine-substituted pyrimidines, polyethylene glycol (PEG) linkage, etc. (both of which are used in Macugen, an FDA-approved aptamer) are available to scientists with which to increase the half-life of aptamers easily to the day or even week time scale.

In addition to the development of aptamer-based therapeutics, many researchers have been developing diagnostic techniques for whole cell protein profiling called proteomics, and medical diagnostics for the distinction of disease versus healthy states. As a resource for all in vitro selection the Aptamer Database catalogs all published experiments. This is found online at aptamer.icmb.utexas.edu/. AptaBiD or Aptamer-Facilitated Biomarker Discovery is a technology for biomarker discovery. AptaBiD is based on multi-round generation of aptamer or a pool of aptamers for differential molecular targets on the cells which facilitates exponential detection of biomarkers. It involves three major stages: (i) differential multi-round selection of aptamers for biomarker of target cells; (ii) aptamer-based isolation of biomarkers from target cells; and (iii) mass spectrometry identification of biomarkers. The important feature of the AptaBiD technology is that it produces synthetic affinity probes (aptamers) simultaneously with biomarker discovery. In AptaBiD, aptamers are developed for cell surface biomarkers in their native state and conformation. In addition to facilitating biomarker identification, such aptamers can be directly used for cell isolation, cell visualization, and tracking cells in vivo. They can also be used to modulate activities of cell receptors and deliver different agents (e.g., siRNA and drugs) into the cells.

The affinities and selectivities of aptamers can rival those of antibodies. In the present invention, the aptamers can be readily site-specifically modified during chemical or enzymatic synthesis to incorporate particular reporters, linkers, or other moieties. Also, aptamer secondary structures can be engineered to undergo analyte-dependent conformational changes, which, in concert with the ability to specifically place chemical agents, allowing various possible signal transduction schemas, irrespective of whether the detection modality is optical, electrochemical, or mass based.

In another embodiment, the nucleic acid moiety is an oligonucleic acid sequence that can be used as an identifying sequence, a barcode sequence, a probe, a capture sequence for hybridization, a recognition sequence, a gene expression control sequence, a gene sequence, enhancers, and/or sequences incorporating or derived from naturally-occurring enzymes, proteins, or other sequences.

In one embodiment, the nucleic acid moiety sequences attached to the cell are the same. In another embodiment, the nucleic acid moiety sequences attached to the cell can be different. This would permit the attachment of nucleic acid moieties for multiples uses. For example, a capture nucleic acid moiety for the capture of the cell at a particular placement, and hybridization or activated sequences to accomplish a specific activity or utility.

In some embodiments, the nucleic acid moiety can be an oligonucleotide, DNA, RNA, PNA or an aptamer. In other embodiments, the nucleic acid moiety can be single-stranded DNA (ssDNA). In some other embodiments, the nucleic acid moiety can be from about 10 to about 100 nucleic acids. In still other embodiments, the nucleic acid moiety can be an aptamer.

The nucleic acid moiety of the present invention can also include a linker. In another embodiment, a chemical linker for the cell attachment system is used to link the oligonucleotide to the cell surface. Referring now to FIG. 1A, the linker facilitates binding to a cell moiety on the cell surface such as an amino acid, carbohydrate, or other cell surface moiety. In one embodiment, the linker is a moiety that can bind directly to the amino acid on the cell without first modifying the amino acid (or carbohydrate or other moiety on the cell surface). The chemical linker is placed at one end of the oligonucleotide to be attached. In one embodiment, formation of a bond with an amino acid on the cell surface protein by the chemical linker alters its character and a covalent bond is formed between the amino acid and the nucleic acid oligonucleotide via the chemical linker. In some embodiments, the bond formed is an amide or ester bond. Thus, in the process of attaching to the amino acid, the chemical linker will typically change its character to form the amide, ester, or other bond, and the cell surface moiety will also conform to become part of the covalent bond.

In one specific embodiment, an N-hydrosuccinimide (NHS) ester is one such possible chemical linker, formed by the reaction of a carboxylate with NHS in the presence of carbodiimide. NHS or sulfo-NHS ester-containing reagents react with nucleophiles with release of the NHS or sulfo-NHS leaving group to form an acylated product. The reaction of such esters with a sulfhydryl or hydroxyl group forms ester linkages or sulfohydryl ester linkages. Both of these bonds can potentially hydrolyze in aqueous environments or exchange with neighboring amines to form amide bonds and an NHS leaving group.

In another embodiment, the chemical linker is a heterobifunctional crosslinker. In one embodiment, the heterobifunctional crosslinker is a NHS-PEO$_n$-Maleimide. NHS-PEO$_n$-Maleimide reagents are heterobifunctional crosslinkers with N-hydroxysuccinimide (NHS) ester and maleimide groups that allow covalent conjugation of amine- and sulfhydryl-containing molecules.

In another embodiment, crosslinkers having polyethylene glycol (PEG), also referred to as polyethyleneoxide (PEO), spacers are convenient alternatives to reagents with purely hydrocarbon spacer arms. PEG spacers improve water solubility of reagent and conjugate, reduce the potential for aggregation of the conjugate, and increases flexibility of the crosslink, resulting in reduced immunogenic response to the spacer itself. By contrast to typical PEG reagents that contain heterogeneous mixtures of different PEG chain lengths, these PEO reagents are homogeneous compounds of defined molecular weight and spacer arm length, providing greater precision in optimization and characterization of crosslinking applications. For example, succinimidyl-[(N-maleimidopropionamido)-hexaethyleneglycol] ester was used in the examples to make a stock solution by dissolving 5 mg of NHS-PEO$_6$-maleimide (Pierce Biotechnology, Inc. Rockford, Ill. 61105).

In another embodiment, the presence of sialic acid and EDC or 1-ethyl-3-(3-dimethylaminopropyl) carbodiimide hydrochloride (a carbomiide used for conjugating biological substances containing carboxylates and amines), an NHS-maleimide can conjugate with a sulfohydryl-oligonucleotide and reacted with an amino acid to form an ester bond at the cell surface.

The amino acids possible for forming the amide, ester, or other bond with the linker on the oligonucleotide include lysine, cysteine, aspartamate, glutamate, tyrosine, tryptophan and serine. Generally, lysine, cysteine, aspartamate, glutamate, and tyrosine form amide bonds with an NHS-oligonucleotide, and serine will form an ester bond with an NHS-oligonucleotide. Other linkers may form different bonds. For example reagents including maleimide, disulfide and the process of acylation can be used to form a direct covalent bond with a cysteine on a cell surface protein. Amide coupling can be used at an aspartamate and glutamate to form an amide bond. Diazonium coupling, acylation, and alkylation can be used at a tyrosine on the cell surface to form an amide bond linkage. It is possible that any of the amino acids (20 amino acids or any unnatural amino acids) can be used to form the direct covalent bond that is the attachment of the oligonucleotide with the cell surface. The 20 amino acids are isoleucine, leucine, lysine, methionine, phenylalanine, threonine, tryptophan, and valine (essential amino acids), and alanine, asparagine, aspartate, cysteine, glutamate, glutamine, glycine, proline, serine, and tyrosine, the nonessential amino acids, and also arginine and histidine.

In general, any affinity molecule useful in the prior art, in combination with a known ligand to provide specific recognition of a detectable substance will find utility in the attachment of nucleic acid groups of the invention. Examples of such biological molecules which can then be attached to these functional groups include linker molecules having a known binding partner, or affinity molecule, include but are not limited to, polysaccharides, lectins, selectins, nucleic acids (both monomeric and oligomeric), proteins, enzymes, lipids, antibodies, and small molecules such as sugars, peptides, aptamers, drugs, and ligands.

In another embodiment, the attachment is covalent. A bifunctional crosslinker useful for the invention would comprise two different reactive groups capable of coupling to two different functional targets such as peptides, proteins, macromolecules, semiconductor nanocrystals, or substrate. The two reactive groups can be the same or different and include but are not limited to such reactive groups as thiol, carboxylate, carbonyl, amine, hydroxyl, aldehyde, ketone, active hydrogen, ester, sulfhydryl or photoreactive moieties. For examples, in one embodiment, a cross-linker can have one amine-reactive group and a thiol-reactive group on the functional ends. Further examples of heterobifunctional cross-linkers that may be used as linking agents in the invention include but are not limited to:

amine reactive+sulfhydryl-reactive crosslinkers.
carbonyl-reactive+sulfhydryl-reactive crosslinkers.
amine-reactive+photoreactive crosslinkers
sulfhydryl-reactive+photoreactive crosslinkers
carbonyl-reactive+photoreactive crosslinkers.
carboxylate-reactive+photoreactive crosslinkers
arginine-reactive+photoreactive crosslinkers Below is a list of categories in which crosslinkers generally fit. The list is exemplary and should not be considered exhaustive of the types of crosslinkers that may be useful for the invention. For each category, i.e. which functional group these chemical target, there are some subcategories, because one reactive group is capable of reacting with several functional groups.

Most crosslinkers with reactive groups can be broadly classified in the following categories:

1. Amine-reactive: the cross-linker couple to a amine (NH2) containing molecule.
2. Thiol-reactive: the cross-linker couple to a sulfhydryl (SH) containing molecule
3. Carboxylate-reactive: the cross-linker couple to a carboxylic acid (COOH) containing molecule.
4. Hydroxyl-reactive: the cross-linker couple to a hydroxyl (—OH) containing molecule.
5. Aldehyde- and ketone-reactive: the cross-linker couple to an aldehyde (—CHO) or ketone ($R_2CO$) containing molecule.
6. Active hydrogen-reactive.
7. Photo-reactive.

More specifically, chemical entering in these categories include, but are not limited to those containing:

1. Isothiocyanates, isocyanates, Acyl Azides, NHS esters, Sulfonyl chlorides, aldehydes and glyoxals, epoxides and oxiranes, carbonates, arylating agents, imidoesters, carbodiimides, anhydrides, alkynes.
2. Haloacetyl and alkyl halide derivates, maleimides, aziridines, acryloyl derivatives, arylating agents, thiol-disulfides exchange reagents
3. Diazoalkanes and diazoacetyl compounds, such as carbonyldiimidazoles and carbodiimides
4. Epoxides and oxiranes, carbonyldiimidazole, oxidation with periodate, N,N'-disuccinimidyl carbonate or N-hydroxylsuccimidyl chloroformate, enzymatic oxidation, alkyl halogens, isocyanates
5. Hydrazine derivatives for schiff base formation or reduction amination
6. Diazonium derivatives for mannich condensation and iodination reactions
7. Aryl azides and halogenated aryl azides, benzophenones, diazo compounds, diazirine derivatives For each of these subcategories there are many examples of chemicals. All these chemicals and the above list of subcategories are described in the prior art, but many can be found in, "*Bioconjugate Techniques*" by Greg T Hermanson, Academic Press, San Diego, 1996, which is hereby incorporated by reference.

The choice of buffer solution wherein the conjugation and attachment to the cells is carried out, depends on the choice of chemical linker or crosslinker and maintaining growth conditions for cells (i.e., to prevent cell lysis). In a preferred embodiment, the buffer solution range is from pH 6-8 and should not contain the same functional groups used in the chemical linker to react with the single-stranded nucleic acid. A pH of 7.2 is the median pH, but the pH does not have be neutral, but is dependent on compatibility with the chemical reaction and the cellular conditions.

In one embodiment, the buffer solution is a phosphate buffer solution of neutral pH such that an N-hydrosuccinimide (NHS) ester (e.g., NHS-PEO-maleimide) may be used as the chemical linker. The reaction is generally carried out under conditions that allow the conjugation of the chemical linker and the nucleic acid and the subsequent attachment to the cell or cell surface. In some embodiments where an NHS ester crosslinker and phosphate buffer solution is used, the reactions are carried out at neutral pH (e.g., pH 7.2) and at room temperature for a specified period of time (e.g., 1, 3, 5, 10, 15, 20, 30, 45, 60 or more minutes).

In some embodiments, the conjugate includes a mammalian cell having lysine on the cell surface, and a single-stranded DNA covalently linked to the lysine via an amide.

The conjugates of the present invention can be prepared by any suitable means known in the art. In general, the method involves linking DNA to the native functional group of a cell where the cell is unmodified, but isolating the cell from other biological material that might interfere with the conjugation step. Any bioconjugation technique can be used, such as those described above in Hermanson.

In some embodiments, the present invention includes a method of preparing a conjugate of a cell and a nucleic acid moiety, by contacting the cell with an activated nucleic acid moiety, wherein the cell has a surface including a native functional group and wherein the cell has no cell wall, such that the nucleic acid moiety is covalently linked to the native functional group.

The activated nucleic acid moiety includes a linker, as described above. In some embodiments, the activated nucleic acid moiety includes an activated ester. In other embodiments, the method of making the conjugates includes contacting a mammalian cell with an activated nucleic acid moiety, wherein the native functional group includes lysine and the activated nucleic acid moiety includes an NHS-ester, such that the nucleic acid moiety is covalently linked to the native functional group by amide bond formation.

B. Conjugates of Cells with Cell Walls

The present invention also provides conjugates of nucleic acid moieties and cells with cell walls, as well as methods of making. In some embodiments, the present invention provides a conjugate of a cell having a cell wall, and a nucleic acid moiety wherein the nucleic acid moiety is covalently linked to the cell. In other embodiments, the nucleic acid moiety is covalently linked to the cell surface.

The native functional group can be any suitable native functional group, such as an amino acid or sugar. Sugars useful for linking to the nucleic acid moiety include, but are not limited to, glucose, ribose, fructose, sialic acid, mannose, galactose, sucrose, lactose, and others. Other sugars include, but are not limited to monosaccharides, disaccharides and polysaccharides.

In another embodiment, attachment of oligonucleotides to cell surfaces can be accomplished with plant cells, bacterial cells, fungi, yeast, algae, and archaea. The attachment in this case requiring first a modification of a carbohydrate molecule on the cell surface, and then attachment of an oligonucleotide-linker to the modified moiety. The major difference between animal cells and plant cells is that the plant cells have cell walls, thus requiring modification before attachment of the oligonucleotide. In one embodiment, attachment of oligonucleotides can be achieved through periodate oxidation followed by hydrazone formation. In one embodiment, a carbohydrate on the plant cell can be modified instead of modifying a protein as in other embodiments using mammalian or animal cells. In the present example, the carbohydrate sugar is oxidized to generate a functional aldehyde (or a ketone). An aldehyde or ketone is then reacted with synthetic hydrizido-DNA to form a covalent bond called a hydrazone.

More generally, the composition comprises an oligonucleotide conjugated to a chemical linker, the linker covalently attached to an outside surface of the cell. The bond or linkage is generally a hydrazone, an oxime, or an amine. The method to form the bond between the oligonucleotide and the cell surface carbohydrate includes modifying the non-animal cell surface carbohydrate to form an aldehyde or a ketone. The process of this formation can include periodate oxidation. The aldehyde or ketone is then contacted with an oligonucleotide having a functional group that reacts to form a covalent bond. The covalent bond can be a hydrazone, an oxime, or an amine linkage between the linker on the oligonucleotide and the carbohydrate on the surface of the cell. Generally, the linkage with these bonds is at a carbohydrate on the cell surface. The reaction can be performed with a non-animal cell or an animal cell, preferably with non-animal cells such as plants, yeast, bacteria and algae and other unicellular organisms. In some embodiments, the cell is a plant cell.

In other embodiments, the native functional group includes a modified native functional group. As described above, the native functional group can be a sugar having a 1,2-diol group that is oxidized to form aldehydes or ketones. In some other embodiments, the modified native functional group includes an oxidized sugar. In still other embodiments, the modified native functional group includes a sialic acid, mannose, glucose, galactose, N-acetylglucosamine or N-acetylmannosamine.

The present invention also provides a method of making the conjugates of a nucleic acid moiety and a cell with a cell wall. As described above, the method can include a two-step process of first modifying the native functional group of the cell having a cell wall, followed by conjugation of the nucleic acid moiety to the modified native functional group.

In some embodiments, the present invention provides a method for preparing a conjugate of a cell and a nucleic acid moiety, including contacting the cell with an activated nucleic acid moiety wherein the cell has a cell wall, such that the nucleic acid moiety is linked to the cell. The activated nucleic acid moiety can include any suitable activated group to enable conjugation of the nucleic acid moiety to the cell, as described above. In some embodiments, the activated nucleic acid moiety includes an aminooxy, a hydrazide, a hydrazine, a semicarbazide, a thiosemicarbazide or an amine. Alternatively, the activated nucleic acid moiety can include cysteine to form thiazolidines or serine to form oxazolidines. Other methods of conjugating the nucleic acid moiety and cell are described in Hermanson (see above).

The method of preparing the conjugate with a cell having cell walls also includes the step of modifying the native functional group. In some embodiments, the method of preparing the conjugate of a nucleic acid moiety and a cell with cell walls, includes contacting the native functional group with a modifying agent to prepare a modified native functional group, such that the nucleic acid moiety is covalently linked to the modified native functional group.

The modifying agent can be any suitable agent to prepare the modified native functional group. For example, the modifying agent includes, but is not limited to, an oxidizing agent. In some embodiments, the modifying agent includes an oxidizing agent. Suitable oxidizing agents include, but are not limited to, sodium periodate. In other embodiments, the oxidizing agent includes sodium periodate. In some other embodiments, the modified native functional group includes an oxidized sugar. In still other embodiments, the modified native functional group includes an oxidized sialic acid. In yet other embodiments, the modified native functional group includes an aldehyde group.

IV. Devices

The present invention also provides substrate surfaces and devices that include the conjugates of the present invention. In some embodiments, the present invention provides a device including a cell having a cell surface including a native functional group covalently linked to a first nucleic acid moiety. The device also includes a substrate surface including a second nucleic acid moiety complementary to the first nucleic acid moiety, such that the cell is bound to the substrate surface via formation of a nucleic acid duplex of the first and second nucleic acid moieties.

In some embodiments, the cell is an animal cell.

The substrate surface can be of any suitable material. Examples of suitable materials include, but are not limited to, glass (including controlled-pore glass), polymers (e.g., polystyrene, polyurethane, polystyrene-divinylbenzene copolymer), silicone rubber, quartz, latex, a derivatizable transition metal, magnetic materials, silicon dioxide, silicon nitride, gallium arsenide, and derivatives thereof. The substrate surface can also have any suitable surface geometry, including, but not limited to, planar, curved and spherical.

In some embodiments, the substrate surface is planar. In other embodiments, the substrate surface is spherical.

In some embodiments, the device also includes channels for fluid. In other embodiments, the channels are microchannels. In some other embodiments, the channels are nanochannels.

In some embodiments, the device includes a sensor. In other embodiments, the sensor includes a nanosensor. In some other embodiments, the sensor includes an electrode. In still other embodiments, the sensor includes a piezoelectric sensor. In yet other embodiments, the device is adapted for atomic force microscopy.

In some embodiments, the device is adapted for biochemical or electrochemical analysis of the cell. In other embodiments, the biochemical analysis includes genomic analysis. In some other embodiments, the device also includes a component selected from a microfabricated heater, a temperature sensor, polymerase chain reaction (PCR) chambers or capillary electrophoretic separation channels. In still other embodiments, the device is capable of generating a transcriptional profile of the cell.

In some embodiments, the device also includes a bioreactor.

In another embodiment, the present invention provides a platform for use to observe and screen for processes that can be studied through cell capture by oligonucleotide attachment such as wound healing, tissue regeneration, infection, reactivity or responsiveness to test drugs, drug screening generally, and gene expression in response to stimuli. The present invention also provides methods and synthetic systems that permit various human states and conditions (e.g., diseased and normal) to be studied or detected through cell capture by oligonucleotide attachment. For example, oligonucleotide attachment to cells may also be applied in the practice of diagnosis of a disease by detection of a cell surface marker of the disease by detecting the hybridization of the cell surface marker to a capture oligonucleotide.

Cells having oligonucleotide strands attached on their surface can be hybridized or annealed to each other in three dimensions, such as fluid or gel. Many applications of this technology are possible. A three-dimensional scaffold or mesh can be used to pattern many more cells than can be displayed on a planar surface. Thus, in one embodiment, a mesh, porous bulk material, or scaffold can be modified to display oligonucleotides attached to the surface such that cells modified using the present methods can be displayed or captured on the surface. Such surfaces can be used to study genetics, aging, and drug response or for metabolic engineering and production and collection of cellular byproducts.

For example the cells can be used to study tissue regeneration, such as myocardial tissue regeneration, wherein a critical number of cells form a beating unit upon accumulation of the sufficient number of cells. Any tissue can potentially be "grown" using a seeded cell attachment matrix to generate a network of interacting cells. The dynamics and products of such cell aggregates and simulated tissues can be studied and controlled. For example, stem cell differentiation and storage can be facilitated using the cell attachment system. For example, adult stem cells and induced pluripotent stem cells can be kept from differentiation or guided to a differentiated state as a desired cell type. Artificial tissues can be generated for replacing lost, damaged, or diseased tissue in animals including humans. Neural and spinal tissue regeneration can be effected in the proper environment in vitro or in vivo. In order to guide or study the cells in such a system, a sensor may be positioned within the cells or on a surface in contact with the cells.

The cell attachment system can be used for delivery purpose, using the cell with attached oligonucleotides to deliver other cell surface molecules such as aptamers, gene regulating molecules, gene expression control molecules, genes for control of gene expression. The cell attachment system can also be used to deliver to another cell the contents of the cell having the oligonucleotides attached. For example, small molecules, peptides, peptidomimetics, vectors having DNA for gene expression, interfering RNA molecules such as small inhibitor RNA or short hairpin RNA, and other deliverable molecules. An aptamer on the surface of the cell can bind an internalizing receptor and the cell is internalized with its contents. Generally, a cell having on its surface an oligonucleotide that is an aptamer adapted to bind a protein will provide the delivery mechanism to or into another living cell. The aptamer itself may comprise a nucleic acid adapted to act within the cell such as an oligonucleotide for expression in the cell, an interfering RNA, (such as an siRNA, an shRNA, or a microRNA) or a molecular beacon such as a nucleic acid having a label adapted to bind a specific sequence in the cell and provide optical detection of that sequence or gene represented by that sequence. The nucleic acids can enhance gene expression, control gene expression, block gene expression, or modify gene expression, among other genomic modifying activities.

In another embodiment, the invention provides methods for sequence specific patterning or capture of cells on a substrate and screening methods. For example, a cell or cell sample can be incubated with PBS phosphate buffer pH 7.2 and the linker for several minutes to several hours as described in the examples to attach the single-stranded oligonucleotide to the cell surface, thus resulting in a cell modified on its surface with an oligonucleotide. A substrate surface can be prepared having a sequence (e.g., a ssDNA capture sequence) attached to the substrate surface. In one embodiment, the single-stranded oligonucleotide attached to the cell is complementary to the ssDNA capture sequence attached to the substrate such that when the cell is allowed to contact the substrate, the two sequences hybridize, thus immobilizing the cell to the substrate.

Thus, in another embodiment, the present invention further provides devices featuring cells immobilized on a surface using the present methods of cell modification. In one embodiment, the devices of this invention can be sensors patterned in microarrays or microarray-like patterns. In another embodiment, the cell or cell membrane with oligonucleotides attached can be used in a device for analyzing the cell or other purposes. In some embodiments, the device will have complementary oligonucleotides on its surface for hybridizing to an oligonucleotide attached to a cell using the present methods. The device can be any useful shape, for example planar or spherical. It can have channels for fluid (i.e., micro channels or nanochannels). The device can include a sensor, such as a nanosensor, an electrode, or a piezo electrode. The device can be adapted for atomic force microscopy, biochemical analysis of the cell, or genomic analysis. The device can have additional components such as a heater, a temperature sensor, and components such as PCR chambers and capillary electrophoretic separation channels for generating a transcriptional profile of the cell, among other possible processes. The device can further comprise a bioreactor. The device can comprise a component selected from a microfabricated heater, a temperature sensor, polymerase chain reaction (PCR) chambers and capillary electrophoretic separation channels.

In one embodiment, for detection of the hybridization event the oligonucleotide attached to the cell or the complementary oligonucleotide or capture oligonucleotide on the device is labeled depending on the device. For example, if the label is added with the amplification mix, the cDNA is on the template strand while the probes are on the sense strand (unless they are negative controls). The label is typically fluorescent, although occasionally radiolabels and the like are used. The labeling can be direct or indirect. Indirect labeling requires a coupling stage which can occur before or after hybridization. If labeling occurs before hybridization, hybridization (e.g., in two-channel arrays) nucleotides labeled with dyes such as aminoallyl-UTP and NHS amino-reactive dyes (like cyanine dyes) can be employed. The aminoallyl group is an amine group typically on a long linker attached to the nucleobase, which reacts with a reactive dye. In some embodiments, the modified nucleotides (typically a 1 aaUTP: 4 TTP mix) are added enzymatically at a lower rate compared to normal nucleotides, typically resulting in 1 every 60 bases as measured with a spectrophotometer. The aaDNA is then purified with a column for example, using solution containing Tris phosphate buffer containing amine groups.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays. In spotted microarrays, the probes are oligonucleotides, cDNA or small fragments of PCR products that correspond to mRNAs. The probes are synthesized prior to deposition on the array surface and are then "spotted" onto glass. A common approach utilizes an array of fine pins or needles controlled by a robotic arm that is dipped into wells containing DNA probes and then depositing each probe at designated locations on the array surface. The resulting "grid" of probes represents the nucleic acid profiles of the prepared probes and is ready to receive complementary cDNA or cRNA "targets" derived from experimental or clinical samples.

In one embodiment, the oligonucleotide probes in these oligonucleotide microarrays are short sequences designed to match parts of the sequence of known or predicted open reading frames. In such an array, the oligonucleotide arrayed on the substrate can be produced by printing short oligonucleotide sequences designed to represent a single gene or family of gene splice-variants by synthesizing this sequence directly onto the array surface instead of depositing intact sequences. Sequences may be longer (60-mer probes such as the Agilent design) or shorter (25-mer probes produced by Affymetrix) depending on the desired purpose; longer probes are more specific to individual target genes, shorter probes may be spotted in higher density across the array and are cheaper to manufacture. One technique used to produce oligonucleotide arrays include photolithographic synthesis (Agilent and Affymetrix) on a silica substrate where light and light-sensitive masking agents are used to "build" a sequence one nucleotide at a time across the entire array. Each applicable probe is selectively "unmasked" prior to bathing the array in a solution of a single nucleotide, then a masking reaction takes place and the next set of probes are unmasked in preparation for a different nucleotide exposure. After many repetitions, the sequences of every probe become fully constructed. More recently, Maskless Array Synthesis from NimbleGen Systems has combined flexibility with large numbers of probes.

Two-color microarrays or two-channel microarrays are typically hybridized with cDNA prepared from two samples to be compared (e.g. diseased tissue versus healthy tissue or diseased cells versus healthy cells) and that are labeled with two different fluorophores. Fluorescent dyes commonly used for cDNA labelling include Cy3, which has a fluorescence emission wavelength of 570 nm (corresponding to the green part of the light spectrum), and Cy5 with a fluorescence emission wavelength of 670 nm (corresponding to the red part of the light spectrum). The two Cy-labelled cDNA samples are mixed and hybridized to a single microarray that is then scanned in a microarray scanner to visualize fluorescence of the two fluorophores after excitation with a laser beam of a defined wavelength. Relative intensities of each fluorophore may then be used in ratio-based analysis to identify up-regulated and down-regulated genes.

The present cell modifications can be made to cells and used in microfluidics applications, methods and devices. The present methods of cell surface modification enable the capture and immobilization of a single cell onto a surface, which thereby permits the cell to be acted on in various ways. For example, in a specific embodiment, an integrated microfluidic device can be made such as that described in Example 4 and described in Toriello, et al, Integrated microfluidic bioprocessor for single-cell gene expression analysis, Proc. Natl. Acad. Sci. U.S.A., 105, 20173-20178, 2008 December 23; 105(51):20173-8. Epub 2008 December 15, hereby incorporated by reference. This integrated microdevice was developed for the analysis of gene expression in single cells. Reverse-transcription PCR amplification of a single cell is enabled by the immobilization and capture of a single-cell on the surface of this integrated microdevice.

Thus in one embodiment, the present methods enable microfluidic structures which feature immobilized cells using the present direct cell modifications. Such microfluidic structures may include micropneumatic systems, i.e. microsystems for the handling of off-chip fluids (liquid pumps, gas valves, etc), and microfluidic structures for the on-chip handling of nano- and picoliter volumes for use in various molecular biology procedures, such as for enzymatic analysis (e.g., glucose and lactate assays), DNA analysis (e.g., polymerase chain reaction and high-throughput sequencing), and proteomics.

Such microfluidic devices are intended to integrate assay operations such as detection, as well as sample pre-treatment and sample preparation on one chip. An emerging application area for biochips is clinical pathology, especially the immediate point-of-care diagnosis of diseases. In addition, microfluidics-based devices, capable of continuous sampling and real-time testing of air/water samples for biochemical toxins and other dangerous pathogens, can serve as a biosensor (e.g., a "bio-smoke alarm") for early warning.

In another embodiment, microfluidics for use with cells having oligonucleotides attached by the present method include continuous-flow technologies based on the manipulation of continuous liquid flow through microfabricated channels. Actuation of liquid flow is implemented either by external pressure sources, external mechanical pumps, integrated mechanical micropumps, or by electrokinetic mechanisms. Continuous-flow microfluidic operation is the mainstream approach because it is easy to implement and less sensitive to protein fouling problems. Continuous-flow devices are adequate for many well-defined and simple biochemical applications, and for certain tasks such as chemical separation, but they are less suitable for tasks requiring a high degree of flexibility or complicated fluid manipulations. Process monitoring capabilities in continuous-flow systems can be achieved with highly sensitive microfluidic flow sensors based on MEMS technology which offer resolutions down to the nanoliter range.

Other embodiments include but are not limited to, Digital (droplet-based) microfluidic alternatives to the above closed-channel continuous-flow systems including novel open structures, where discrete, independently controllable droplets are manipulated on a substrate.

In addition to microarrays, another embodiment comprises biochips designed for two-dimensional electrophoresis, transcriptome analysis, PCR amplification, etc. Other applications include various electrophoresis and liquid chromatography applications for proteins and DNA, cell separation, in particular blood cell separation, protein analysis, cell manipulation and analysis including cell viability analysis and microorganism capturing.

In another embodiment, the present direct cell modification methods enable a device for single cell imaging, manipulation and patterning. For example, cells can be analyzed or patterned using an atomic force microscope (AFM) or scanning force microscope (SFM). Thus, in one embodiment, a device such as an AFM cantilever as described in Hsiao S C et al., DNA-coated AFM cantilevers for the investigation of cell adhesion and the patterning of live cells, Angew Chem Int Ed Engl. 2008; 47(44):8473-7, 16 Sep. 2008 Epub, hereby incorporated by reference, and also described in Example 8. The advantages the technology embodied in the invention bring to an AFM device is an ability to precisely place cells using AFM cantilevers for analysis and manipulation. Both AFM and SFM are very high-resolution type of scanning probe microscopes, with demonstrated resolution of fractions of a nanometer, more than 1000 times better than the optical diffraction limit.

The ability to subject a whole live cell to an AFM using the oligonucleotide attachment system of the invention provides the opportunity to specifically analyze multiple cell types, simultaneously, and indeed to analyze a single cell with greater fidelity because it is securely held and controlled from its oligonucleotide anchors. For example, another major application of AFM (besides imaging) is force spectroscopy, the measurement of force-distance curves. For this method, the AFM tip is extended towards and retracted from the surface as the static deflection of the cantilever is monitored as a function of piezoelectric displacement. These measurements have been used to measure nanoscale contacts, atomic bonding, Van der Waals forces, and Casimir forces, dissolution forces in liquids and single molecule stretching and rupture forces. Forces of the order of a few pico-Newtons can now be routinely measured with a vertical distance resolution of better than 0.1 nanometer.

Micro and nanotechnology are being applied to chemical analysis, environmental monitoring, medical diagnostics and cellomics and microreactors for pharmaceutics. Research in lab on a chip (LOC) systems is expected to extend towards downscaling of fluid handling structures as well, by using nanotechnology. Sub-micrometer and nano-sized channels, DNA labyrinths, single cell detection an analysis and nano-sensors might become feasible that allow new ways of interaction with biological species and large molecules. The present invention contributes to making these systems possible for whole cells. LOC systems can accomplish real-time PCR, facilitate biochemical assays, immunoassay, detect bacteria, viruses and cancers based on antigen-antibody reactions, dielectrophoresis detecting cancer cells and bacteria, blood sample preparation, can crack cells to extract DNA, cellular analysis, on channel screening.

Lab-on-a-chip technology may soon become an important part of efforts to improve global health, particularly through the development of point-of-care testing devices. In countries with few healthcare resources, infectious diseases that would be treatable in a developed nation are often deadly. In some cases, poor healthcare clinics have the drugs to treat a certain illness but lack the diagnostic tools to identify patients who should receive the drugs. Many researchers believe that LOC technology may be the key to powerful new diagnostic instruments. The goal of these researchers is to create microfluidic chips that will allow healthcare providers in poorly equipped clinics to perform diagnostic tests such as immunoassays and nucleic acid assays with no laboratory support. An innovative polymer lab-on-a-chip (LOC) for reverse transcription (RT)-polymerase chain reaction (PCR) has been designed, fabricated, and characterized for point-of-care testing (POCT) clinical diagnostics. In addition, a portable analyzer that consists of a non-contact infrared (IR) based temperature control system for RT-PCR process and an optical detection system for on-chip detection, has also been developed and used to monitor the RT-PCR LOC.

In another embodiment, a fully integrated genomic analysis microsystem including microfabricated heaters, temperature sensors, and PCR chambers directly connected to capillary electrophoretic separation channels has been constructed. In Example 6, an integrated microfluidic bioprocessor for single-cell gene expression analysis is described and also described in Toriello et al., "Integrated microfluidic bioprocessor for single-cell gene expression analysis", PNAS, Dec. 23, 2008 vol. 105 no. 51 20173-20178, online on 9/16/08, and hereby incorporated by reference. The device is an important step toward a microfabricated genomic microprocessor for use in forensics and point-of-care molecular medical diagnostics. Whether the cells are displayed on a device, or connected to one another, analysis of gene expression can be determined by measuring mRNA levels with multiple techniques including microarrays, expressed cDNA sequence tag (EST) sequencing, serial analysis of gene expression (SAGE) tag sequencing, massively parallel signature sequencing (MPSS), or various applications of multiplexed in-situ hybridization. All of these techniques are extremely noise-prone and/or subject to bias in the biological measurement, and a major research area in computational biology involves developing statistical tools to separate signal from noise in high-throughput gene expression studies. Such studies are often used to determine the genes implicated in a disorder: one might compare microarray data from cancerous epithelial cells to data from non-cancerous cells to determine the transcripts that are up-regulated and down-regulated in a particular population of cancer cells.

Analysis of regulation can likewise occur in these oligonucleotide linked cells: regulation is the complex orchestration of events starting with an extracellular signal such as a hormone and leading to an increase or decrease in the activity of one or more proteins. Bioinformatics techniques have been applied to explore various steps in this process. For example, promoter analysis involves the identification and study of sequence motifs in the DNA surrounding the coding region of a gene. These motifs influence the extent to which that region is transcribed into mRNA. Expression data can be used to infer gene regulation: one might compare microarray data from a wide variety of states of an organism to form hypotheses about the genes involved in each state. In a single-cell organism, one might compare stages of the cell cycle, along with various stress conditions (heat shock, starvation, etc.). One can then apply clustering algorithms to that expression data to determine which genes are co-expressed. For example, the upstream regions (promoters) of co-expressed genes can be searched for over-represented regulatory elements.

In another embodiment, the presently modified cells with an oligonucleotide attached is used in or integrated into a sensor device that measures a physical quantity and converts it into a signal which can be read by an observer or by an instrument. For example, analysis of protein expression can also be accomplished with these compositions and systems. Protein microarrays and high throughput (HT) mass spectrometry (MS) can provide a snapshot of the proteins present in a cell. Bioinformatics is very much involved in making sense of protein microarray and HT MS data; the former approach faces similar problems as with microarrays targeted at mRNA, the latter involves the problem of matching large amounts of mass data against predicted masses from protein sequence databases, and the complicated statistical analysis of samples where multiple, but incomplete peptides from each protein are detected.

Analysis of mutations in cancer, or any other disease or conditions can be accomplished by these systems using the oligonucleotide captured cells. In cancer, the genomes of affected cells are rearranged in complex or even unpredictable ways. Massive sequencing efforts are used to identify previously unknown point mutations in a variety of genes in cancer. Bioinformaticians continue to produce specialized automated systems to manage the sheer volume of sequence data produced, and they create new algorithms and software to compare the sequencing results to the growing collection of human genome sequences and germline polymorphisms. New physical detection technology are employed, such as oligonucleotide microarrays to identify chromosomal gains and losses (called comparative genomic hybridization), and single nucleotide polymorphism arrays to detect known point mutations. These detection methods simultaneously measure several hundred thousand sites throughout the genome, and when used in high-throughput to measure thousands of samples, generate terabytes of data per experiment. Again the massive amounts and new types of data generate new opportunities for bioinformaticians. The data is often found to contain considerable variability, or noise, and thus Hidden Markov model and change-point analysis methods are being developed to infer real copy number changes. In the structural branch of bioinformatics, homology is used to determine which parts of a protein are important in structure formation and interaction with other proteins. In a technique called homology modeling, this information is used to predict the structure of a protein once the structure of a homologous protein is known. This currently remains the only way to predict protein structures reliably.

Comparative genomics can be made with the systems of the invention. The core of comparative genome analysis is the establishment of the correspondence between genes (orthology analysis) or other genomic features in different organisms. It is these intergenomic maps that make it possible to trace the evolutionary processes responsible for the divergence of two genomes. A multitude of evolutionary events acting at various organizational levels shape genome evolution. At the lowest level, point mutations affect individual nucleotides. At a higher level, large chromosomal segments undergo duplication, lateral transfer, inversion, transposition, deletion and insertion. Ultimately, whole genomes are involved in processes of hybridization, polyploidization and endosymbiosis, often leading to rapid speciation. The complexity of genome evolution poses many exciting challenges to developers of mathematical models and algorithms, who have recourse to a spectra of algorithmic, statistical and mathematical techniques, ranging from exact, heuristics, fixed parameter and approximation algorithms for problems based on parsimony models to Markov Chain Monte Carlo algorithms for Bayesian analysis of problems based on probabilistic models.

The cells and systems can be used for making prognoses and diagnoses of patients. Individual genomes can be genotyped and analyzed using the devices enabled by direct cell modification. For example, a genotyping stage can have many different experimental approaches including single nucleotide polymorphism (SNP) chips (typically 0.02% of the genome), or partial or full genome sequencing. Once the genotypes are known, there are many bioinformatics analysis tools that can compare individual genomes and find disease association of the genes and loci.

In another embodiment, the presently modified cells are used in a bioreactor device or system to facilitate bioactivity in a cell or between several molecules, and generally resulting in a finished product or some other desired result such as a bioactivity (e.g. metabolism, energy production, electrical signals, catabolism, apoptosis, growth, differentiation, proliferation, etc.). For example, metabolism of a cell can be studied in these systems. A bioreactor may refer to any device or system that supports a biologically active environment.

Scientific advances in biomaterials, stem cells, growth and differentiation factors, and biomimetic environments have created unique opportunities to fabricate tissues in the laboratory from combinations of engineered extracellular matrices ("scaffolds"), cells, and biologically active molecules. In another embodiment, the present cell modification methods enable cells to be attached or placed on other surfaces meant to grow cells or tissues in the context of cell culture. For example, cells having single stranded oligonucleotides attached by a covalent bond to their surface can be hybridized to a complementary strand on a neighboring cell or on a surface, therefore providing the means for linking cells together and/or to a surface for generation and study of cells, tissues, and organs. Powerful developments in the multidisciplinary field of tissue engineering have yielded a novel set of tissue replacement parts and implementation strategies which the present methods will find use. In one embodiment, cells modified with an oligonucleotide attached can be implanted or 'seeded' into an artificial structure capable of supporting three-dimensional tissue formation. Bulk materials, stents, scaffolds, which are often critical, both ex vivo as well as in vivo, to recapitulating the in vivo milieu and allowing cells to influence their own microenvironments can be modified to allow cell attachment using the present methods.

In one embodiment, a photosynthetic single-celled organism is modified using the present methods and an oligonucleotide is attached. Proposed organisms include but are not limited to, Photosynthetic: *C. reinhardtii* (algae), *Synechocystis* PCC 6803 (cyanobacteria), *R. rubrum* (gram negative anaerobe); Heterotrophs: *C. pasteurianum* (nitrogen fixer), *Azotobacter* sp. (proposed to have the highest respiration rate of any organism). (see Melis et al, cited elsewhere herein).

In one embodiment, algae is modified and an oligonucleotide is attached. Algae may be especially suitable because it can grow rapidly and can have a high percentage of lipids, or oils. They can double their mass several times a day and produce at least 15 times more oil per acre than alternatives such as rapeseed, palms, soybeans, or jatropha. Due to its lack of need for clean water, algae farming is also more cost effective than many other crops, and produces much less strain on fresh water resources. It can also be grown without displacing food crops. The oligonucleotide attachment system allows control of the placement of a plant, bacterial, or algae cell on a surface, for example, a surface angled to maximize exposure to sunlight.

In another embodiment, the presently modified cells with an oligonucleotide attached can be used to in a fuel cell or other electrochemical conversion device. It produces electricity from fuel (on the anode side) and an oxidant (on the cathode side), which react in the presence of an electrolyte. The reactants flow into the cell, and the reaction products flow out of it, while the electrolyte remains within it. Fuel cells can operate virtually continuously as long as the necessary flows are maintained. Fuel cells are different from electrochemical cell batteries in that they consume reactant from an external source, which must be replenished—a thermodynamically open system. By contrast batteries store electrical energy chemically and hence represent a thermodynamically closed system. Many combinations of fuel and oxidant are possible. A hydrogen cell uses hydrogen as fuel and oxygen (usually from air) as oxidant. Other fuels include hydrocarbons and alcohols. Other oxidants include chlorine and chlorine dioxide.

Living solar cells can be created using the green algae *Chlamydomonas reinhardtii* for microbial electricity generation as described in Rosenbaum, Appl. Microbiol. Biotechnol. (2005) 68: 753-756. Two chambered microbial fuel cells are described in Wang et al, Electrochimica Acta 54 (2009) 1109-1114. Self-sustained phototrophic microbial fuel cells (MFCs) are described in He et al, Environ. Sci. Technol. 2009, 43, 1648-1654 in which production of electricity from self-sustained sediment phototrophic MFC was achieved using a mixed microbial community of photosynthetic microorganisms and heterotrophic bacteria. Electricity was constantly generated from these MFCs with no input of organic compounds or nutrients. Kjeang et al (Journal of Power Sources 158 (2006) 1-12) describe strategic enzyme patterning for microbial fuel cells to optimize a combined fuel and oxidant channels in a non-compartmentalized fuel cell assembly with separated enzymes patterned in the device in relation to individual turnover rates. Ringeisen et al. J. of Power Sources 165(2007) 591-597 describes a miniature MFC constructed using *Shewanella* (DSP10) *oneidensis* that remains active in anaerobic and aerobic environments. Previous studies showed that electrons from this bacteria have been used to reduce metals in the presence of oxygen. The bacteria was used in the devices as the actived electrochemical species in the anode chamber. The paper points out that sensors for underwater surveillance systems require as an ideal power source a small (stealthy, not dominating in size compared to the device it powers) that can function in an aerobic environment (ie. in a water column close to the water surface), providing continuous power (with no recharging or lifetime issues) and not requiring high levels of solar radiation (therefore functioning subsurface and at night time, etc.). The bacteria selected for the study by this group provides the opportunity for RF communication for a sensor network because it does not have to be in an anaerobic environment for the anode, and therefore can function in light environments at the water surface. It is also reported that microbial fuel cells in current designs can be made more robust if powered by solar energy, and the power possible in such systems depends on the nature of the nitrogen source and the availability of light. In carefully designed systems a combination of nitrogen (e.g. from sediments, wastewater, or agricultural wastes) processing systems can be powered using solar energy to power the nitrogen processing cells of the system (see Cho et al, J. Applied Microbiology 104 (2008) 640) with the result yielding more electricity and increased longevity of the system.

Thus, devices using the oligonucleotide attachment systems of the invention can be made such as, for example, fuel cell devices using the oligonucleotide modified non-animal cells of the invention and other principles consistent with the invention. For example, hydrogen producing fuel cells can be made using modified plant cells. Typically the plant cells can be patterned so that hydrogen producers and oxygen scavengers are combined in an optimal arrangement for energy production. The devices can be planar or spherical, or provide any surface optimal for the capture and processing of solar energy and can comprise a sensor. Devices can also be made to study or use for energy purposes plant, bacterial or algae cells. The device can further be used to store energy. The device can comprise a sensor, or can be a bioreactor. Algae based systems can be a foundation for sustainable and commercially viable integrated biological hydrogen production processes using photosynthetic $H_2$ production by green algae, the visible region of the solar spectrum coupled to $H_2$ production by anoxygenic photosynthetic bacteria utilizing the near infrared region of sunlight. Biomass accumulation in the course of photosynthesis by the two organisms is subsequently utilized in dark anaerobic fermentations for further $H_2$ production. Small organic acids accumulate as a by product of the dark anaerobic fermentation, and these can serve as a substrate to support further hydrogen production by green algae and photosynthetic bacteria. The foundation of such integrated $H_2$ production is the oxygenic photosynthesis of unicellular green algae (e.g. *Chlamydomonas reinhardtii*), a process that uses the energy of sunlight to convert water, carbon dioxide and other inorganic nutrients into the basic building blocks of life. (See A. Melis, and M. R. Melnicki, International J. of Hydrogen Energy 31 (2006) 1563-1573).

Other photosynthetic, photovoltaic non-animal cell based systems to which the tools of this invention can be applied include Dickson et al. International J. Hydrogen Energy, 34 (2009) 204-215 which describes use of *Synechocystis* sp. PCC 6803 to form a silica sol-gel. Such technology may be directly applicable to powering small electronic devices. Sui et al. J. of Microelectromechanical systems vol. 17, no. 65, December 2008 describes a microfabricated polydimethylsiloxane (PDMS) microbial fuel cell (MFC) with embedded micropillar electrodes. This MFC is characterized by a flexible and biocompatible structure suitable for body implantation as a potential power source for implanted bioMEMS devices. Song et al, describes a microfluidic polymer electrolyte membrane (PEM) fuel cell using polydimethylsiloxane (PDMS) for a bioMEMS device, which can be used for powering portable electronic devices and other miniaturized MEMS devices. The work described by Song et al, patterns a submicron-thick Nafion membrane on a glass substrate using a reversibly bonded PDMS microchannel to generate an ionselective membrane between the fuel cell electrodes, instead of sandwiching a thin Nafion sheet. Due to the flexibility of the PDMS material, the Nafion membrane can be sealed between the PDMS chip and glass substrate by oxygen plasma bonding. Surface patterning can be seamlessly integrated into a standard microfabrication process flow and form a PEM microfluidic fuel cell without cumbersome clamping of the layers together and inherent risks of leakage due to ineffective clamping. At the very least, this device construction makes possible building of massively parallel arrays of microfluidic fuel cells. Patterning of cells can be facilitated using the cell attachment methods of the present invention.

In another embodiment, the cell surfaces that are modified using the present modification technique are cell membrane-like surfaces such as the coat proteins of viruses, phage and other self-assembled biomolecular surfaces or structures. Example 9 demonstrates that viral or phage capsids modified with the present cell modification methods to conjugate a DNA aptamer to the surface, enables the creation of multivalent cell targeting vehicles. Thus the present direct cell modification methods can be used in the modification of many monomeric or biomolecular surfaces for any number of applications requiring the direct attachment of a nucleic acid or oligonucleotide.

V. Kits

The present invention also provides kits having an activated nucleic acid moiety suitable for forming a nucleic acid-cell conjugate of the present invention, and a substrate surface having a complementary nucleic acid moiety. In some embodiments, the present invention provides an activated nucleic acid moiety suitable for covalent linkage to a native functional group of a cell surface, and a substrate surface including a nucleic acid moiety complementary to the activated nucleic acid moiety. The activated nucleic acid moiety can be a powder or be in a solution. The kit can also include buffer solutions known to one of skill in the art, and other solutions for forming the nucleic acid-cell conjugate and then binding the nucleic acid-cell conjugate to the substrate surface via the nucleic acid moiety on the substrate surface.

The components of the kits are described in more detail above. The substrate surface can include any suitable material including, but not limited to, glass microscope slides, cover slips, tissue culture plates, or well plates. The substrate surface can be preprinted with nucleic acid moieties in specific locations. The kits can include other components, such as fixing solutions for the cells, solutions of detection agents, solutions of cell staining agents, buffer solutions, etc. Other solutions can include the nucleic acid moieties themselves, and solutions and reactants for attaching the nucleic acid moieties to the cells.

VI. Examples

Example 1. Conjugation of DNA to a Cell without a Cell Wall Via a Lysine Native Functional Group All cell culture reagents were obtained from Gibco/Invitrogen Corp (Carlsbad, Calif.) unless otherwise noted. Cell culture was conducted using standard techniques. Jurkat cells were grown in T-25 culture flasks (Corning, USA) in RPMI Medium 1640 supplemented with 10% (v/v) fetal bovine serum (FBS, HyClone) and 1% penicillin/streptomycin (P/S, Sigma). MCF-7 cells were grown in DMEM supplemented with 1% non-essential amino acids and 10% fetal bovine serum, plus 1% penicillin/streptomycin. MDA-MB-231 cells were grown under the same conditions as the MCF-7 cells, but without non-essential amino acids.

Fluorescence micrographs were acquired using an Axiovert 200M inverted microscope (ZEISS) with fluorescence filter sets for DAPI/Hoechst, fluoroscein/fluo-3, and rhodamine. Ultraviolet absorption of the different oligonucleotides was determined at 260 nm on a UVIKON 933 double beam UV/vis spectrophotometer (Kontron Instruments, United Kingdom).

Synthesis of NHS-DNA Conjugates.

For cell adhesion studies, three complementary oligonucleotide pairs were designed such that they were identical in overall composition and differed only in sequence. Each sequence pair was also calculated to possess comparable melting temperatures (55° C.) and minimal secondary structures.

The sequence identities were as follows:

```
C1:
                                          (SEQ ID NO: 1)
5'-GTA ACG ATC CAG CTG TCA CT-3'

M1:
                                          (SEQ ID NO: 2)
5'-AGT GAC AGC TGG ATC GTT AC-3'

C2:
                                          (SEQ ID NO: 3)
5'-TCA TAC GAC TCA CTC TAG GG-3'

M2:
                                          (SEQ ID NO: 4)
5'-CCC TAG AGT GAG TCG TAT GA-3'

C3:
                                          (SEQ ID NO: 5)
5'-ACT GAC TGA CTG ACT GAC TG-3'

M3:
                                          (SEQ ID NO: 6)
5'-CAG TCA GTC AGT CAG TCA GT-3'
```

The oligonucleotides were obtained from Integrated DNA Technologies (Coralville, Iowa) with thiol groups installed at the 5'-end. Samples (2 mg in 80 μL) were combined with 320 μL of 10 mM tris(2-carboxyethyl)phosphine (TCEP) and 400 μL of 1×TE buffer (10 mM Tris with 1 mM EDTA, brought to pH 7.5 with HCl) and stored frozen at −20° C. until use. NHS-PEO$_6$-Maleimide (succinimidyl-[(N-maleimidopropionamido)-hexaethyleneglycol] ester) was purchased from Pierce. A stock solution was prepared by dissolving 5 mg of NHS-PEO$_6$-maleimide in 1 mL of DMSO (Sigma). Aliquots of this solution (20 μL each) were stored at −20° C. until use.

DNA modification was achieved by passing a thawed solution of 5'-thiol ssDNA (30 μL, 0.39 mM) through a NAP-5 size-exclusion column (GE Healthcare). The eluent was then exposed to 20 μL of the NHS-PEO$_6$-Maleimide solution at room temperature for 10 minutes. The reaction was then purified by passing it through a second NAP-5 column that was pre-equilibrated with PBS solution (pH 7.2). The concentration of DNA in the column eluent was verified using UV-vis spectroscopy. The resulting solution was then applied to samples of live cells.

To confirm the nature of the modification chemistry, models of the oligonucleotide conjugates were prepared and characterized. To do this, 0.5 mL of DMF was saturated with 6-amino-N-(4-aminophenethyl) hexanamide and added to 1 mL of the reaction solution obtained after NAP-5 purification. After 30 min of incubation at room temperature, the oligonucleotide conjugates were analyzed using MALDI-TOF MS. Observed masses were within 0.090% of expected values.

Modification of live cells and quantification of attached DNA molecules was accomplished as follows: Immediately prior to modification, a sample of 5×106 Jurkat cells was washed with PBS buffer three times to remove any proteins from the culture medium. The cells were then exposed to solutions of NHS-DNA (C3 strand, 3 μM to 54 μM final concentrations) for 30 minutes at room temperature. After isolation via centrifugation, the cells were returned to the culture medium, or labeled with fluorescent DNA complements as described below.

In order to quantify the number of surface DNA molecules, portions of the modified cells were incubated with 10 μL solutions of FITC-labeled complementary DNA strands at 0° C. for 30 minutes. The cells were then washed with PBS solution and resuspended in PBS containing 1% FBS prior to analysis. The cells were then analyzed by flow cytometry. Fluorescence measurements were calibrated using fluorescent beads of known fluorophore density. Fluorescence measurements were compared to those corresponding to control cells lacking DNA modification and cells reacted with mismatch DNA sequences.

FIGS. 31A and 31B show the DNA-cell conjugates prepared by the method above binding to substrate surface modified with a complementary DNA strands, demonstrating formation of the DNA-cell conjugate.

Example 2. Conjugation of DNA to a Cell without a Cell Wall Via an Aspartic Acid or Glutamic Acid Native Functional Group DNA has been conjugated to cells using EDC coupling chemistry by the following procedure:
1. Take 5 million cells and wash them with 10 mL PBS two times.
2. Dissolve 0.366 g EDC in 19.06 mL PBS.
3. Add 0.452 g NHS to the EDC solution.
4. Make sure pH is around 7. (Normally they are)
5. Take 1 mL of this EDC/NHS solution, added with 200 uL 80 uM amine-ssDNA (in 1×SSC).
6. Incubate at rt for 30 min to 1 hr.
7. Wash with 10 mL of 1% FBS/PBS three times.
8. Resuspend to 50 to 100 uL 1% FBS/PBS, and ready to be applied to the slides.

Example 3. Conjugation of DNA to Oxidized Sugar Native Functional Group

Oxidation of Surface Exposed Diols (Lipopolysaccharide, Lipoteichoic Acid, Etc.) on Cells with Cell Walls.

Rinse cells ($10^5$-$10^7$) in 1 mL Dulbecco's phosphate buffered saline (DPBS) using centrifugation. Suspend cells in 2 mL 0.5-5 mM NaIO$_4$ in DPBS and place at 37° C. with orbital shaking for 20 min. Lower concentrations of periodate are needed for eukaryotes such as algae and yeast. Neutralize periodate with 1 mL 0.1 M glucose in DPBS. Centrifuge cells down and wash 2×1 mL DPBS, 1×1 mL pH 6 MOPS buffer (see below).

Attachment of Hydrazide-Modified ssDNA to Oxidized Surface Exposed Diols.

Suspend cells in 800 μL pH 6 MOPS Buffer (0.5 M NaCl, 0.1 M 3-(N-morpholino)propanesulfonic acid, 18.2 MΩ H$_2$O, adjust pH to 6.0)+10 mM aniline+~35 μM hydrazide ssDNA (purchased from Integrated DNA Technologies). Allow cells to react at room temperature for 1-18 hr, depending on concentration of surface diols, with gentle shaking. Spin cells down and rinse with DPBS FIGS. 32A, 32B and 32C show the DNA-cell conjugates prepared by the method above binding to substrate surface modified with a complementary DNA strands, demonstrating formation of the DNA-cell conjugate.

Example 4. Devices

General protocol for the attachment of DNA strands to cells and for their immobilization onto DNA-printed surfaces was as follows: Immediately prior to modification, a sample of 5×106 Jurkat cells was washed with PBS buffer three times to remove any proteins from the culture medium. After the final rinse, additional PBS was added to bring the volume to 5 mL (1×106 cell/mL). The cell suspension was then reacted with 1 mL of NHS-DNA (11.7 μM) solution synthesized and purified from 30 μL of 5'-thiol ssDNA (C2 sequence). The mixture was allowed to react at room temperature for 30 minutes, and was then washed three times with PBS containing 1% FBS. The cells were then resuspended in 0.5 mL of PBS containing 1% FBS.

To print the glass surfaces, a 20 μM solution of 5' amine functionalized ssDNA in 3× saline sodium citrate buffer (SSC: 45 mM sodium citrate, 450 mM NaCl, pH 7.0) was used for sample preparation. DNA solutions were deposited onto aldehyde-functionalized glass slides (SCHOTT Nexterion, Louisville, Ky.) by manual pipetting or by using a robotic microarray printing system at the UC Berkeley Functional Genomic Laboratory. Spotted DNA was immobilized and the slides were passivated according to the manufacturer's protocol. After printing, the slides were dried under a stream of $N_2$ and stored in the dark under a dry atmosphere. Patterned slides were typically used within one month.

Micropatterning of the glass slides was achieved using photolithography in conjunction with an aluminum lift-off technique, and will be described in full detail elsewhere. For studies with one cell type, all cells were labeled with the C2 sequence. Slides were patterned with complementary DNA sequence, M2 unless otherwise noted. Solutions of DNA-modified cells were introduced onto each surface and incubated for 3-5 minutes without agitation. The devices were then washed twice with PBS containing 1% FBS. Replicate data sets were collected by selecting three device regions at random before washing. Each location was photographed, washed, and then visualized again.

Evaluation of cell viability was made as follows: Jurkat cells coated with the C2 strand were seeded in a 1 mL Petri dish with normal growth media, and M2 strand DNA was added into the solution to a concentration of 2 μM. Unmodified Jurkat cells were cultured under identical conditions as a control. Cells were counted in each of the four samples using a hemocytometer at 24, 48, and 72 hours. Cell viability was monitored by adding Trypan Blue.

The extent of apoptosis of surface bound cells was determined by annexin V/propidium iodide staining (BD Biosciences). After immobilization on the slides by DNA, the cells were incubated in normal media at 37° C. for 24 hours. A sample of unbound Jurkat cells (lacking surface DNA strands) was incubated under the same conditions as a control. A solution consisting of 900 μL of 1× binding buffer, 30 μL of the annexin V-FITC stock solution, and 30 μL of the PI stock solution was prepared. After 24 hours, 100 μL of this solution was applied to the slides for 15 min at room temperature. The cells were imaged by fluorescence microscopy and the number of non-viable cells counted after one hour.

Immobilization of adherent cell lines on patterned surfaces was accomplished as follows: Two breast cancer cell lines, MCF-7 and MDA-MB-231, were obtained from ATCC. The cells were detached from culture plates with 1 mM EDTA without any trypsin, and the cell solutions were washed with PBS three times. A 5 mL portion of the cell solution (1×10$^6$ cell/mL) was reacted with 1 mL of NHS-DNA solution synthesized from 30 μL of 5'-thiol ssDNA (C2 sequence) as described above. The mixture was allowed to react at room temperature for 30 minutes, and was then washed three times with PBS containing 1% FBS. The cells were then resuspended in 0.5 mL of PBS containing 1% FBS. The cell solution was introduced onto glass slides patterned with complementary DNA sequence M2, and the samples were incubated for 5 minutes. The slides were then washed two times with PBS containing 1% FBS. After immobilization onto slides via DNA hybridization, the cells were incubated in their normal media and observed for 36 hours. Replicate data sets were collected by photographing three different surface regions at 12 hour intervals.

Confirmation of the sequence-specificity of cell immobilization was made as follows: DNA-modified Jurkat cells and MDA cells were prepared by incubating each cell population with NHS-DNA (sequence C2 or C1, respectively) in PBS for 30 minutes as described above. To facilitate visual differentiation of the cells, the cytosol of each population was labeled with either CellTracker Blue™ or CellTracker Green™ live cell stains. After rinsing, equal amounts of each population were mixed, introduced onto microspotted DNA microarrays bearing either sequence M2 or M1 (constructed as above), and incubated for 5 minutes. The microarray was then washed twice with PBS containing 1% FBS and observed under a fluorescence microscope.

Immobilization of human red blood cells was accomplished as follows: Fresh samples of red blood cells were obtained from a blood sample of a healthy human and stored in 1% citric acid solution at room temperature. Cells were used within 1 hour. The cell solution was washed three times with PBS and was then incubated in the NHS-ssDNA solution for 30 minutes to allow modification of cell surfaces. The cell suspension was then washed three times with 1% FBS/PBS solution before being applied to glass slides bearing the complementary ssDNA strands. After cell attachment, the glass slides were washed with 1% FBS/PBS to remove any unbound cells and viewed under an optical microscope. Cells were incubated in 1% FBS/PBS after immobilization, and their viability was examined after 3 hours using trypan blue staining.

Patterning of primary CD4+ T cells and IL-2 Production Assay was conducted as follows: Primary CD4+ T cells (obtained in collaboration with Jay T. Groves' lab, UC Berkeley) were harvested from mice and grown under reported conditions before use. The primary T cells were then modified using the NHS-DNA protocol and exposed to different DNA patterns printed by spotting or by using photolithography, as described above. The glass slides with DNA-immobilized cells were washed with 1% FBS/PBS to remove any unbound cells and viewed under a microscope.

The IL-2 production of primary T cells immobilized with DNA duplexes was examined using ELISA. A population of 2×10$^5$ primary T cells was modified with DNA strands and immobilized on a series of slides (1 cm$^2$) bearing the complementary sequence. These samples were then divided into three portions. The first sample was incubated in normal T cell growth media without any additional reagents. The second sample was treated with PHA (1 μg/mL) and PMA (50 ng/mL). The third sample was treated with ConA (1 μg/mL), PMA (50 ng/mL) and CSA (μg/mL). Analogous samples of free T cells with no surface DNA were prepared as controls. All the cell samples were incubated at 37° C. for 20 h and then centrifuged. Portions of the culture media (1 mL) were withdrawn from each population of cells and tested for IL-2 production using a Mouse Interleukin-2 ELISA test kit (Thermo Scientific).

Patterning of primary myoblasts was accomplished as follows: Primary myoblasts (obtained in collaboration with Randall Lee's lab, UCSF) were harvested from mice and purified according to a published protocol as described in Huang, N. F.; Patel, S.; Thakar, R. G.; Wu, J.; Hsiao, B. S.;

Chu, B.; Lee, R. J.; Li, S. Nano Lett. 2006, 6, 537-542, hereby incorporated by reference. Briefly, normal cell growth was achieved in Ham's F-10 media (Invitrogen) with 10% (v/v) fetal bovine serum (FBS, HyClone), 1 bGF (Invitrogen), and 1% penicillin/streptomycin (P/S, Sigma). Immediately before surface modification the cells were detached with 1 mM EDTA without any trypsin. The resulting cell suspensions were rinsed with PBS three times. A 5 mL portion of the cell solution ($1 \times 10^6$ cell/mL) was reacted with 1 mL of NHS-DNA solution. The mixture was allowed to react at room temperature for 30 minutes, and the cells were then washed three times with PBS containing 1% FBS. Surfaces were patterned with the complementary DNA sequence through spotting or photolithography, and incubated with PBS containing 1% FBS at room temperature for 1 h. The cell solution was introduced onto the slides and incubated for 5 minutes. The devices were then washed three times with PBS containing 1% FBS. After immobilization, the cells were incubated in growth media or fusion media (DMEM (Invitrogen) containing 5% horse serum, and 1% penicillin/streptomycin (P/S, Sigma)) at 37° C. for 14 days. The unbound myoblasts were cultured under identical conditions as a control. Images and movies of all cell samples were recorded every 24 hours.

Example 5. DNA Barcode

A microdevice is developed for DNA-barcode directed capture of single cells on an array of pH-sensitive microelectrodes for metabolic analysis. Cells are modified with membrane-bound single-stranded DNA, and specific single-cell capture is directed by the complementary strand bound in the sensor area of the iridium oxide pH microelectrodes within a microfluidic channel. This bifunctional microelectrode array is demonstrated for the pH monitoring and differentiation of primary T cells and Jurkat T lymphoma cells. Single Jurkat cells exhibited an extracellular acidification rate of 11 milli-pH/min, while primary T cells exhibited only 2 milli-pH/min. This system can be used to capture non-adherent cells specifically and to discriminate between visually similar healthy and cancerous cells in a heterogeneous ensemble based on their altered metabolic properties. The bifunctional microelectrode array demonstrated here shows how devices made using the composition of this invention have the ability to selectively capture cells and measure their electrical and metabolic activity. Using DNA-barcode capture, both adherent and naturally non-adherent cells can be studied on the same device. In addition, the cells so captured are not activated. The array format allows direct discrimination between cells from a mixture, revealing the variation in single cell properties and how that cell contributes to the whole. Controlled single-cell electrochemical measurement points to using a nanoscale cell interface to enable multiplex subcellular analysis of cellular activity.

The controlled capture of single cells in microfluidic devices is essential for the development of integrated microdevices for single cell analysis. With size and volume scales comparable to those of individual cells, microfluidic devices provide a powerful tool for control of the cellular microenvironment. It has been demonstrated that the use of engineered cell surface DNA (cell adhesion barcodes) is capable of cell capture, prior DNA capture of cells could not be used to perform single-cell gene expression analysis in a microfluidic chip, and have that gene analysis representative of an unactivated cell. The devices of this invention have the new capacity to employ DNA barcode cell capture to populate an array of pH-sensitive microelectrodes with unactivated (native) cells. The system enables rapid, selective and reversible capture of non-adherent single cells (previously impossible), as well as adherent cells, on the pH sensor surface. This bifunctional system enables accurate real-time monitoring of single cell metabolism based on the principle that extracellular acidification is proportional to overall energy usage. In these experiments it is demonstrated that this technology can identify cancer cells with high metabolic activity, making the device a potential diagnostic and prognostic tool for cancer treatment. Additionally, because the system can be tailored to be extremely selective and specific about the cells studied and these cells can be placed at precise locations on the device surface, the system is ideal for applications known as patient specific analysis and treatment for any disease, including of course cancer.

Previous work has demonstrated the individual aspects of single cell capture and pH monitoring in microfluidic systems. A variety of methods for arrayed single cell capture have been shown, including physical and energetic traps, and biochemical adhesion. The cells in this prior work were not captured using DNA, but rather physically restrained by barriers in the device environment. While a simple restrictive capture well or microfluidic trap could be used to isolate cells over a sensor, it has been shown that access to fresh media and the ability to clear waste products are important to normal cell function. Highly precise cell placement is also important for monitoring activity if subcellular-scale electrodes are to be used. The oligonucleotide attachment system of the present invention allows for both capture irrespective of physical barriers on the device, and feeding and washing the cells without risk of losing them in the process.

The use of extracellular acidification is a valuable tool in the quantitative analysis of cell activity. A key example is the Cytosensor Microphysiometer, which has been widely used to measure acidification from bulk cell populations ($10^4$-$10^6$ cells per 3 ul sample) as a way to quantify metabolism. This system has been used for a number of applications, including the detection of G-protein coupled (chemokine) receptor activation, neurotrophin activity, ligand gated ion channels, and the binding of ligands to tyrosine kinase receptors. It has also been used to identify ligands for orphan receptors. Other devices have also employed pH electrodes to measure cell activity down to the single cell level. Work described in Ges et al. Biomed. Microdevices, 2008, 10, 347-354 recently demonstrated a device for on-chip measurement of acidification rates from single cardiac myocytes using physical confinement. In the Ges system, single myocytes were isolated in the sensing volume by physically pinching closed the ends of a PDMS channel. While this system represents an important step in single cell monitoring, the cell isolation technique does not allow for controlled capture on the sensor electrodes, which is necessary for simultaneous multi-analyte monitoring from single cells in the same controlled environment. The present invention provides these significant advantages.

The devices described here provide direct integration of the oligonucleotide-based cell capture technique with sensors that are on the same size scale of the individual cells, thus allowing cell analysis never before achievable in a bifunctional electrode system. An array of lithographically patterned iridium oxide pH microelectrodes is enclosed within a microfluidic channel. Single stranded DNA is attached to the iridium oxide surface using a silane linker, giving the sensor the ability to capture cells bearing complementary DNA while retaining its detection sensitivity. Here we use this system to measure the extracellular acidification resulting from the metabolism of non-adherent T cells, and we demonstrate that the pH sensitivity is sufficient to discriminate between healthy primary T cells and cancerous Jurkat T cells that have a higher metabolism. Our results demonstrate the differentiable metabolic activity of individual healthy and transformed cells of the same basic type, which could enable the identification of circulating tumor cells (CTCs) within a heterogeneous sample. The novel combination of DNA-directed cell capture and electrochemical monitoring on a bifunctional electrode offers a new platform for single cell analysis.

Figure 11:
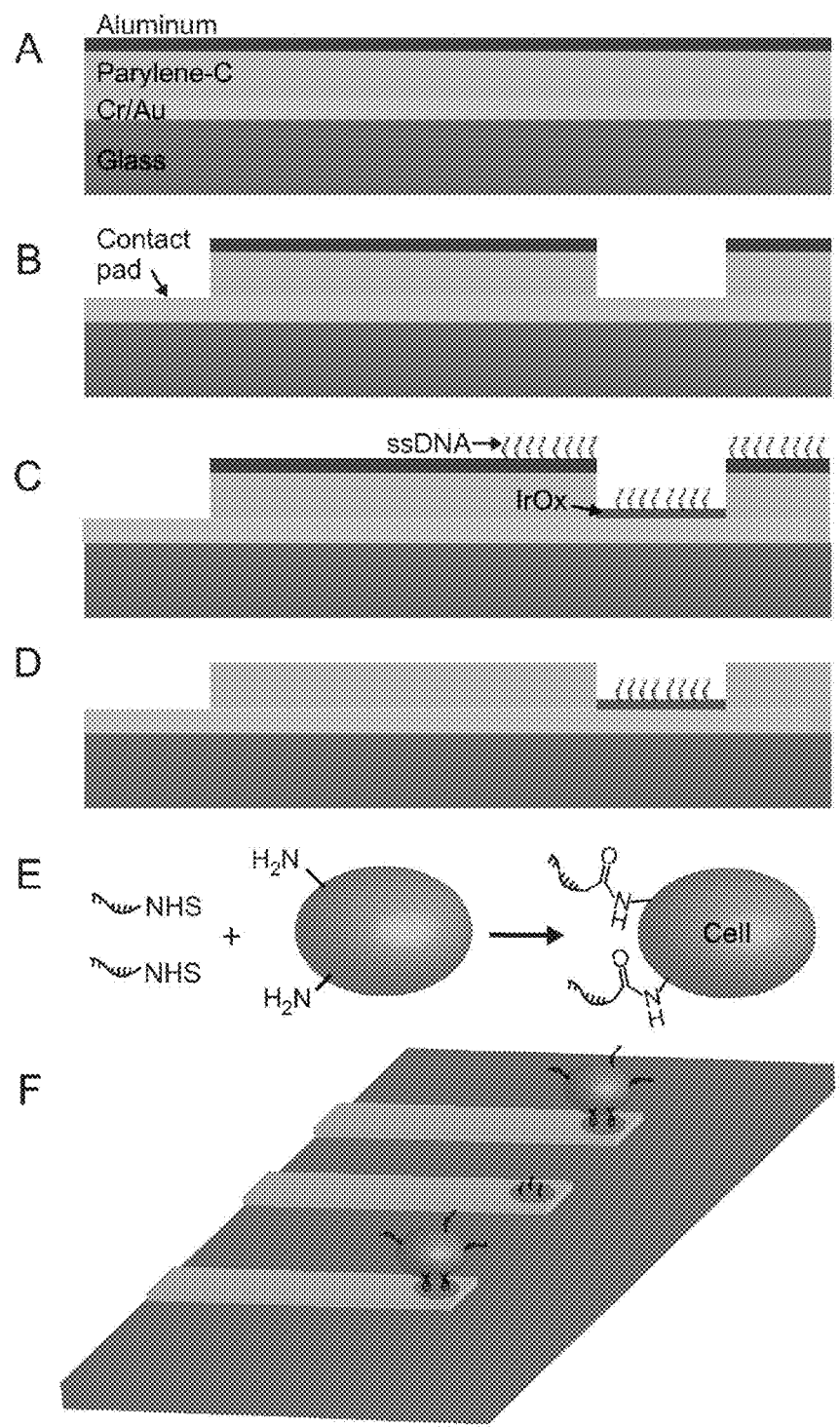
FIG. 11. Fabrication of the bifunctional microelectrode array for single cell monitoring. (A) Gold electrodes are patterned on a glass wafer using photolithography and liftoff. A 7 μm insulating layer of Parylene-c is then deposited onto the electrodes, and covered with a 100 nm layer of evaporated aluminum. (B) Photoresist is patterned on the aluminum layer, which is then etched and used as an etch mask for the Parylene insulation. (C) The sensor layer of iridium oxide is deposited on the electrode surface and then treated with an aldehyde silane for amine-modified capture DNA attachment. (D) Finally, the aluminum layer is dissolved in strong base, leaving only the capture DNA on the sensor surface. Cells bearing the surface-bound complementary strand are introduced and captured directly and specifically on the sensor. (E) Cells are treated with single stranded DNA (5'-CCCTAGAGTGAGTCGTATGA-3'; SEQ ID NO:4) bearing a terminal N-hydroxysuccinimidyl (NHS) ester functional group, which binds to primary amines on the cell surface. This DNA barcode labeling functionalizes the cell for DNA-directed capture in the device. (F) Schematic of the microfluidic device. The electrodes are enclosed by a PDMS channel, forming the microfluidic device.

Electrode sensor fabrication is accomplished as follows: Electrodes (40 nm thick Au with a 20 nm Cr adhesion layer) were patterned on 1.1 mm thick borofloat glass wafers using standard photolithographic liftoff, as previously described (FIG. 11). A 7 μm thick layer of Parylene-c was deposited on the wafer using a Specialty Coating Systems Labcoter 2 Parylene deposition system, and measured with an AlphaStep IQ profilometer. A 100 nm layer of aluminum was evaporated on the device, and then lithographically etched using Air Products aluminum etchant with surfactant for 30 s at 60° C. (FIG. 11A, 11B). The etch mask for the aluminum layer was a photolithographically patterned 1 μm thick film of Shipley 1818 photoresist. The aluminum layer was then used as a mask to etch the underlying Parylene using oxygen plasma (60 sccm $O_2$, 100 W, 60 min).

After removing the Parylene insulation from the sensor area, the sensors were electro-deposited with a layer of iridium oxide following the protocol of Yamanaka et al. Briefly, the iridium deposition solution was prepared as follows. 37.5 g of $IrCl_4$ was added to 75 mL of de-ionized water and stirred for 90 min. Next, 125 mg of oxalic acid was added, and the solution was stirred for 3 h. Finally, the solution pH was adjusted to 11 using $K_2CO_3$. The solution was initially light yellow, turning light blue, and finally dark blue over the course of several weeks. The deposition solution was stable for at least six months after preparation. Iridium oxide deposition was performed using a CHI 660 potentiostat in voltage cycling mode. 240 cycles of +0.7 V (0.25 s) and −0.5 V (0.25 s) were used, in a three electrode configuration using a saturated calomel reference and a platinum counter electrode.

After deposition, the devices were plasma cleaned for 1 min and modified with trimethoxysilylpropanal by vapor deposition at 60° C. for 60 min. Amine-modified ssDNA (80 μM in phosphate buffered saline) was then deposited onto the devices and bound using reductive amination as previously described (FIG. 11C). Following DNA deposition, the protective aluminum layer was dissolved by treatment with 0.1 M NaOH at room temperature with stirring for 20 min, leaving the capture DNA only on the sensor surface (FIG. 11D).

Microfluidic device preparation is accomplished as follows: Poly(dimethylsiloxane) (PDMS) channels were prepared using Dow Corning Sylgard 184 with SU-8 or polystyrene molds. Channels were 5 mm wide, 15 mm long, and 600 μm in height. A fluidic inlet compatible with 20 gage Teflon tubing was punched using an 18 gage blunt-tipped needle, and a 5 mm diameter outlet reservoir was punched on the other end. PDMS channels were cleaned with a UV/ozone system for 10 min, and applied to the device. The channels were filled with DI water for 1 h to allow hydration of the iridium oxide layer, then the pH response of the electrodes was calibrated using standard pH 4, 5, 7 and 10 buffers. The channel was maintained at 37° C. using a heated aluminum stage with a MinCO polyimide heater and Cole-Parmer DigiSense PID temperature controller.

Cell preparation and labeling is accomplished as follows: Jurkat cells were cultured in RPMI-1640 media with 10% fetal bovine serum (FBS) and 1% penicillin-streptomycin solution. Cultured cells were maintained at 37° C. in 5% $CO_2$, and split 1:10 every 2-3 days. Cell acidification experiments were conducted in custom low-buffered media bases on Dulbecco's Modified Eagle's Medium, containing 25 mM D-glucose, 5.3 mM KCl, and 110.34 mM NaCl, plus 1% FBS and penicillin/streptomycin. Finally, the media was pH adjusted to 7.45 using 0.1 M NaOH. Cells were isolated from mice and prepared as previously described (see A. L. DeMond, K. D. Mossman, T. Starr, M. L. Dustin and J. T. Groves, Biophys. J., 2008, 94, 3286-3292).

Cell-surface labeling with ssDNA was achieved using an NHS-DNA conjugate that covalently modifies primary amines on the cell surface (FIG. 11E), as described above. Briefly, cells were incubated in a 120 μM NHS-DNA solution in PBS at room temperature for 30 min, then washed three times to remove any unbound DNA. Barcode-specific cell capture was tested with spotted DNA microarray slides as previously reported (see Douglas et al. Lab Chip, 2007, 7, 1442-1448).

Metabolic monitoring was accomplished as follows: Cells were suspended at a concentration of $10^6$/ml, and the suspension was flowed into the microfluidic device. Cell suspensions were flowed into the channel using 1 mL syringes with Teflon tubing. Where Jurkat and primary T cells were monitored simultaneously they were labeled with Cell-Tracker Green and Red dyes, respectively, as previously described and mixed in an equal ratio. Following a 5 min incubation to allow DNA-based cell capture, the unbound cells were rinsed away (5 ul/min for 3 min) with the low-buffered media. After rinsing, the pH response was monitored electrochemically for 10 min. After this recording, cells were released from the electrodes by heating the device to 55° C. and applying a strong rinse (200 uL/min) with the low-buffered media. Once rinsed and allowed to return to 37° C., the device could be reloaded with cells. This allowed for multiple measurements to be taken with a single cell preparation.

Voltage measurements were recorded between the iridium oxide electrode and a distant FLEXREF Ag/AgCl reference electrode from World Precision Instruments. An identical iridium oxide electrode outside the cell area was used to compensate for any sensor drift. The sensor electrodes were connected to a National Instruments PCI-6031E data acquisition card with 16 bit analog to digital conversion. The digitized signals were monitored using a custom Labview VI, sampling in multiplex at 3 hz. Voltage signals were processed with a 1% Loess filter using Peak Fit software to reduce noise.

Figure 12:
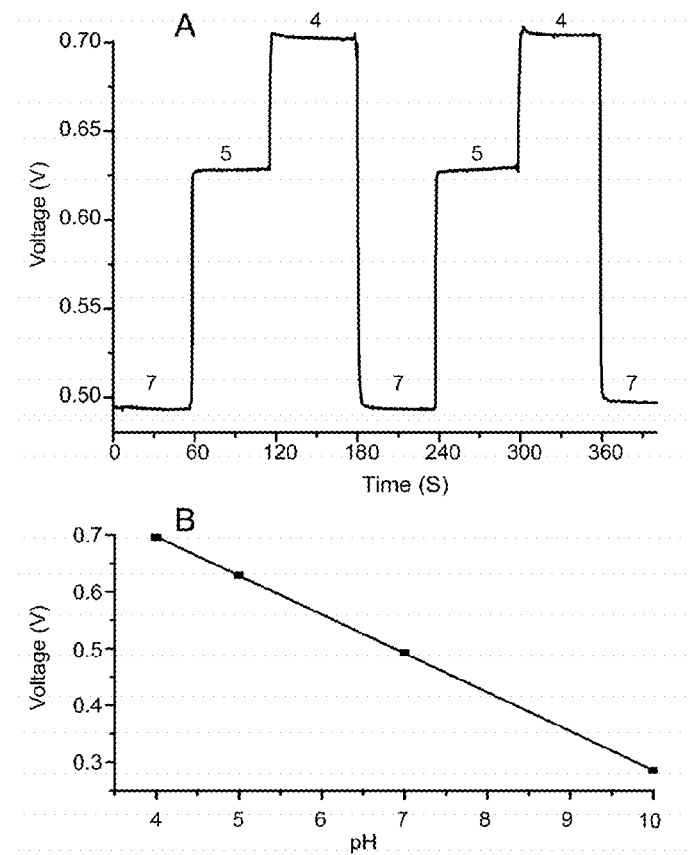
FIG. 12. Calibration data for the bifunctional microelectrode array. (A) Typical calibration recording for one DNA-modified iridium oxide sensor using standard pH 4, 5 and 7 buffers. Voltage is measured relative to an Ag/AgCl reference electrode. (B) Plot of the voltage vs. pH standard measurement with a slope of −68.5 mV/pH unit and $R^2=0.99995$.

Before metabolic analysis, the electrodes were characterized using standard pH buffers (FIG. 12). These DNA-modified electrodes were found to retain their pH sensitivity, with performance comparable to unmodified iridium oxide sensors. The electrode response was stable and fast, responding to a 1 pH unit change in under 500 ms. The pH response of the electrodes was typically −68.5 mV per pH unit, with a linear response over the range pH 4 to 10. The typical range for cell acidification measurements is approximately 6.5 to 7.5, so this sensor is well suited for the measurements. The magnitude of the observed response is in line with the −60 to −80 mV/pH range of other hydrated iridium oxide sensors previously demonstrated. The reaction at the electrode that provides the pH sensitivity has been described by Olthuis et al. The −60 to −80 mV/pH sensitivity range is dependent on the oxidation state of the iridium oxide film as deposited by various electrochemical techniques. The reaction at the electrode that provides the sensitivity was provided by Olthuis.

$$2Ir(OH)_2O^- + H_2O = Ir_2O(OH)_3O^{3-} + 3H^+ + 2e^-$$

Figure 13:
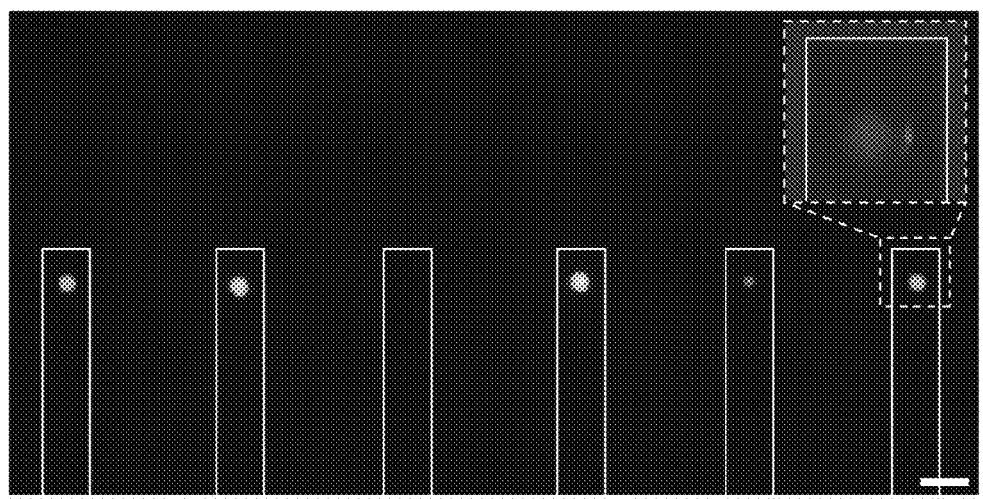
FIG. 13. Cell capture on the bifunctional microelectrode array. Fluorescent micrograph of individual non-adherent Jurkat cells with a surface-bound DNA barcode bound to the complementary strand on the sensor electrode. Electrode areas are outlined in white. Bar=40 μm. Inset: Magnified view of a single Jurkat cell on an electrode, with additional oblique illumination to reveal the electrode area.
Figure 14:
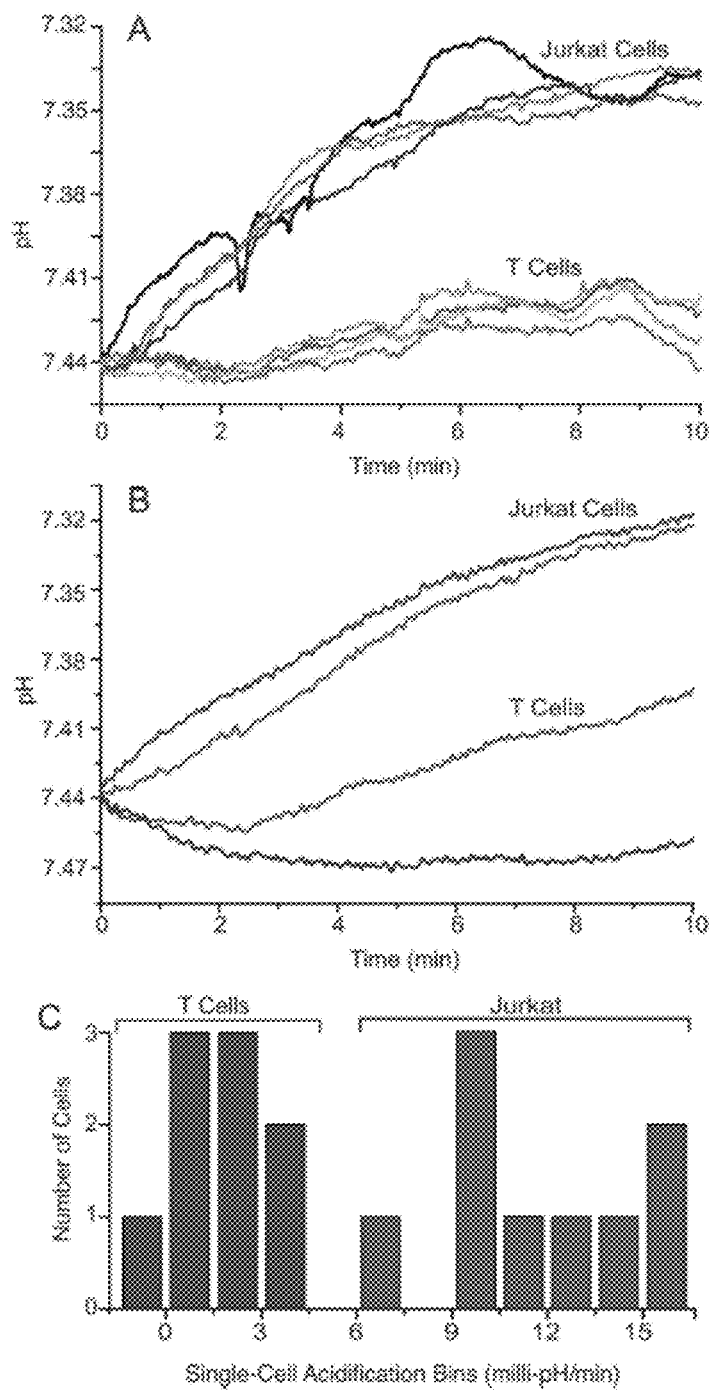
FIG. 14. Single cell acidification measured with the bifunctional microelectrode array. (A) Representative composite data of single Jurkat and primary T cell acidification measured in known homogenous samples. (B) Single Jurkat and primary T cells captured from a mixture and monitored simultaneously over a 10 min span on the array. (C) Histogram of individual cell acidification in known-type samples over 10 min. Jurkat cells are seen to have a significantly higher (P<0.0002) rate of acidification than primary T cells in low-buffered media.

The integration of an affinity capture DNA probe with the pH microelectrodes on the bifunctional microelectrode array chip provides a platform for the direct monitoring of extracellular acidification for cells that are normally non-adherent. The system also provides monitoring of cells that are not activated by the oligonucleotide attachment system, whether adherent or non-adherent cells. As seen in FIG. 13, the size-limiting bifunctional microelectrode enables single cell capture directly on the sensor. The bifunctional microelectrode array was tested by measuring the extracellular acidification of Jurkat and primary T cells. First, Jurkat and primary T cells were captured and monitored separately on the array to establish the sensor functionality and the difference in single-cell acidification between the two cell types. FIG. 14A shows single cell acidification data over a 10 min period. Jurkat cells exhibited an extracellular acidification rate of 11.5±3.3 milli-pH/min, while primary T cells exhibited 1.61±1.5 milli-pH/min (s.d., n=9 each). This difference was also confirmed with bulk cell population acidification measurements (~$10^6$/ml cells in low-buffered media at 37° C.).

To demonstrate the ability to distinguish different cells in a mixed population, single cells from a mixture of Jurkat and primary T cells bearing the same cell adhesion barcode were monitored simultaneously on the array. FIG. 14B shows acidification data from mixed cells on the array over 10 min. The difference in measured acidification rates followed the same trend as the separate samples, and allowed for discrimination between the two visually similar cells (FIG. 14B). Jurkat cells had an acidification rate of 10.1±2.3 milli-pH/min, and healthy T cells had 2.41±2.54 milli-pH/min (s.d., n=5 each).

FIG. 14C presents a bar graph of the acidification rates over several trials using known cell populations on the array. For Jurkat cells the mean acidification rate was 11.5±3.2 milli-pH/min, while primary T cells exhibited a rate of 1.62±1.31 milli-pH/min. The difference is clearly significant with a T-test value of P<0.0002. While the Jurkat cells were slightly larger than the primary T cells (typically 12 µm vs. 10 µm diameter), the size difference is not large enough to account for the difference in acidification.

Figure 15:
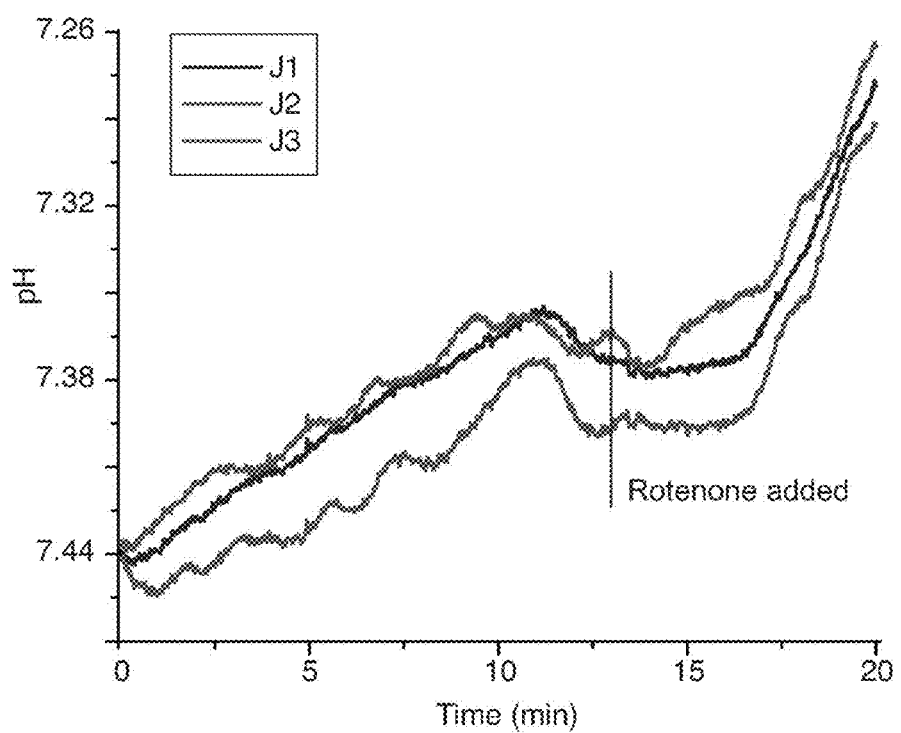
FIG. 15. Single cell stimulation measured by the bifunctional microelectrode array. Jurkat cells exhibit normal baseline acidification during the first 13 minutes, then 125 μL of 10 μM rotenone in low-buffered media is added to the channel outlet reservoir where it diffuses into the channel within seconds. Rotenone inhibits the mitochondrial electron transport chain, causing an increased rate of lactic acid excretion, and therefore a higher rate of acidification.

To demonstrate the ability to measure single cell response to exogenous stimulation, Jurkat cells were treated with rotenone while captured on the bifunctional microelectrode array (FIG. 15). Incubation with rotenone would be expected to interfere with the mitochondrial electron transport chain, causing cells to shift to lactic acid fermentation to complete the glycolytic cycle. The resulting excretion of lactic acid should then increase the rate of acidification in the cellular environment. In the experiment, captured cells were first incubated under normal conditions to establish a baseline rate of acidification (~8.8 milli-pH/min) under aerobic metabolism. After 13 min 10 µM rotenone was added to the channel, which resulted in a three-fold increase in the acidification rate (~27.7 milli-pH/min) within 1 minute. Bulk cell controls, in which Jurkat cells were treated with 1 µM rotenone in low-buffered media (~$10^6$ cells/mL at 37° C.), consistently demonstrated more than twice the acidification over 60 min compared to identical untreated cells. The observation of this metabolic shift provides an important demonstration of this technique's ability to monitor responses to exogenous agents, such as receptor-ligand binding, at the single cell level.

The bifunctional microelectrode array developed here combines the two important functions of selective cell capture and metabolic monitoring of single cells in an array format. In earlier work, Castellarnau et al. used dielectrophoresis to localize high concentration suspensions of bacteria near an ISFET pH sensor and measured the acidification of the cells in the presence of glucose. While this technique was well suited to measurement of the bulk response, it lacks the ability to resolve the unique activity of single cells. The single cardiac cell pH system of Ges et al. provides the ability to monitor large adherent cells, but the volume displacement caused by sealing the channel makes it difficult to direct the cell attachment. DNA-barcode capture provides the advantage of directed capture of both adherent and naturally non-adherent cells, such as T and B cells, and the additional advantage of analyzing cells that are not activated by the oligonucleotide attachment method. This controlled capture provides a platform for spatially-resolved electrical and/or optical probing and measurement of activity on the cell surface.

The acidification data show that single non-adherent cells continue to behave normally after treatment with capture DNA and attachment to the electrode. While any capture technique is likely to have some effect on the cell, cell adhesion barcodes bypass the natural cell-surface receptors that are often used for integrin or antibody-based capture, and should thus avoid the activation of those known signaling pathways. For both the Jurkat and primary T cells the extracellular acidification rates measured are comparable to the single cell acidification rates reported by Ges et al., but the increased sensitivity of our functionalized microelectrode technique allows discrimination between the two cell types.

Our single-cell results show that the difference between the metabolic activity of primary non-transformed cells and immortalized cancerous T cells can be detected at the single-cell level. We have demonstrated the ability to electrochemically distinguish between visually similar single cells from the same basic type using this metabolic difference. This methodology could be used to identify individual circulating tumor cells by their distinctive metabolic activity, going beyond simple antibody-based capture. It could also be used to differentiate between cancerous cells of different metastatic potential. Single-cell monitoring within such a mixture would allow for the detection of differences in drug response based on the cell's state of cancer progression or origin.

The array format with its obvious extension to include more elements allows the direct comparison of the individual activity of many cells under the same conditions with sufficient power to characterize ensemble variation. The construction of a nanofabricated electrode array could produce an electrochemical analysis map of a cell surface with high spatial-resolution. Static cell surface profiling has previously been demonstrated using scanning electrochemical microscopy, but a nanoelectrode array could transform this from a serial to a parallel process and provide temporal resolution as well in live cells.

The system is capable of increasing the number of detected analytes from a single cell and has the capacity for increased complexity of the analysis system in general. The previously mentioned Cytosensor Microphysiometer system for bulk cell monitoring was modified to simultaneously measure glucose, lactate and oxygen levels, in addition to the standard pH measurement capabilities. Micro- or nanofabricated analyte-selective sensors could also be added to the system for additional analytical depth, including multi-analyte sensing on a single cell. A combination of calcium-sensitive fluorophores and electrical control has been used to monitor calcium flux in single neurons during patch-clamp recording by Thayer et al. The PDMS/glass multilayer device is readily modified to enable simultaneous fluorescence and electrical measurements. While fluorescent probes often suffer from photobleaching, the technique embodied here could be used to track single-cell metabolic activity over hours or days, revealing any changes as the cell progresses through its life cycle.

DNA barcode-based cell capture provides the ability to engineer attachment between individual cells which allows for the construction and analysis of discrete multi-type cell systems on an electrode. For example, a single neuron could be linked using DNA to a single muscle cell to allow analysis of the single-cell neuromuscular synaptic formation and operation. Additionally, artificial tissue can be engineered using cell to cell attachment with oligonucleotide hybridization. Sensors can be placed in or near the system to record metabolic, electrical or other changes in the system.

Example 6. Microfluidic Bioprocessor

Single-cell analysis is a powerful approach for understanding changes in gene expression within an isogenic cell population. Traditional gene expression analysis techniques such as microarrays and serial analysis of gene expression are not sensitive enough to analyze changes at the single-cell level and only report on the ensemble average behavior of a large numbers of cells. Recently, a variety of highly sensitive and specialized techniques have been developed for probing gene expression in single cells. Although many of these approaches offer the advantage of real-time monitoring, the protocols required are laborious, often require cellular engineering, and have limited multiplexing capabilities.

Newly developed microfluidic technologies and methods enable single-cell analysis in a format that can be scaled to large numbers of cells. Microfluidic devices present a powerful platform for probing single cells because the intrinsic length (1-100 µm) and volume scales (picoliters-nanoliters) are close to the size and volume of single cells ($\approx$1 pL). The biggest advantage microfluidics offers is the ability to integrate all processing steps into a single device, eliminating sample contamination and product loss, which would preclude sensitive, reproducible, and quantitative single-cell analysis.

The 3 steps that must be integrated into a microdevice to perform single-cell gene expression analysis are cell selection and localization, enzymatic reaction, and quantitative detection of the analyte of interest. Although many microfluidic systems have demonstrated 1 or 2 of these elements, the successful integration of all 3 is extremely challenging. Early microfluidic systems successfully coupled PCR chambers to capillary electrophoresis (CE) separation channels. Recent integrated microsystems have demonstrated a significant increase in detection sensitivity, the handling of crude samples, and massive parallelism. Despite these advances, no integrated microfluidic device has successfully coupled all 3 steps into a single platform to measure changes in gene expression directly from single cells. The fundamental hurdle has been the efficient transfer of analyte between each nanoliter-processing step.

Figure 20:
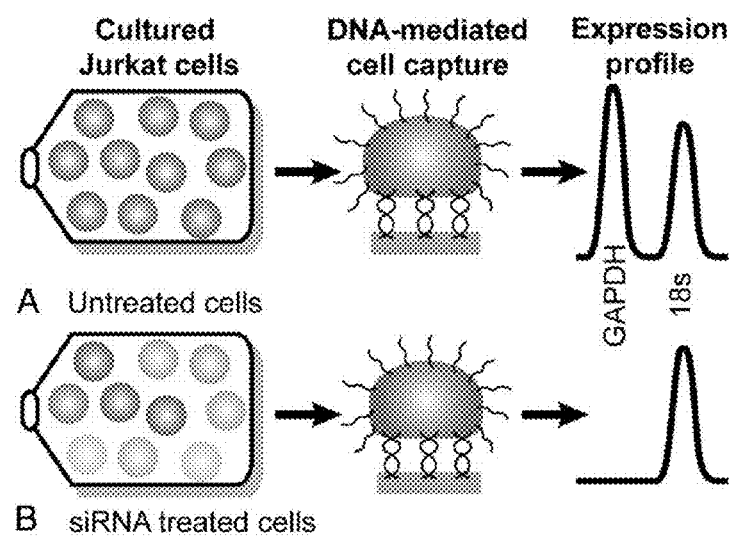
FIG. 20. Overview of single-cell gene silencing assay. Jurkat cells are cultured and surface-labeled, a single cell is captured on a target pad via DNA duplex formation, and an RT-PCR expression profile is generated. (A) Cells under normal growth conditions exhibit homogenous high expression of GAPDH (green cells) compared with a control 18S rRNA. (B) Cells treated with siRNA directed at GAPDH exhibit varying levels of mRNA knockdown.

To address this challenge, we have developed an integrated microfluidic device with all of the necessary elements for single-cell gene expression profiling and used it to perform a study of single-cell gene silencing (FIG. 20). Cells are functionalized with a 20-base oligonucleotide on their surface to enable capture on a gold pad by DNA hybridization. Multiplex gene expression analysis from GAPDH mRNA and control 18S rRNA is performed on 2 cell populations. The first cell population consists of untreated Jurkat T lymphocyte cells grown under normal conditions exhibiting homogenous high expression of both target genes (FIG. 20A). The second cell population is treated with siRNA directed at GAPDH mRNA (FIG. 20B). The degree to which GAPDH mRNA is silenced in individual cells is probed relative to the 18S rRNA control.

Figure 21:
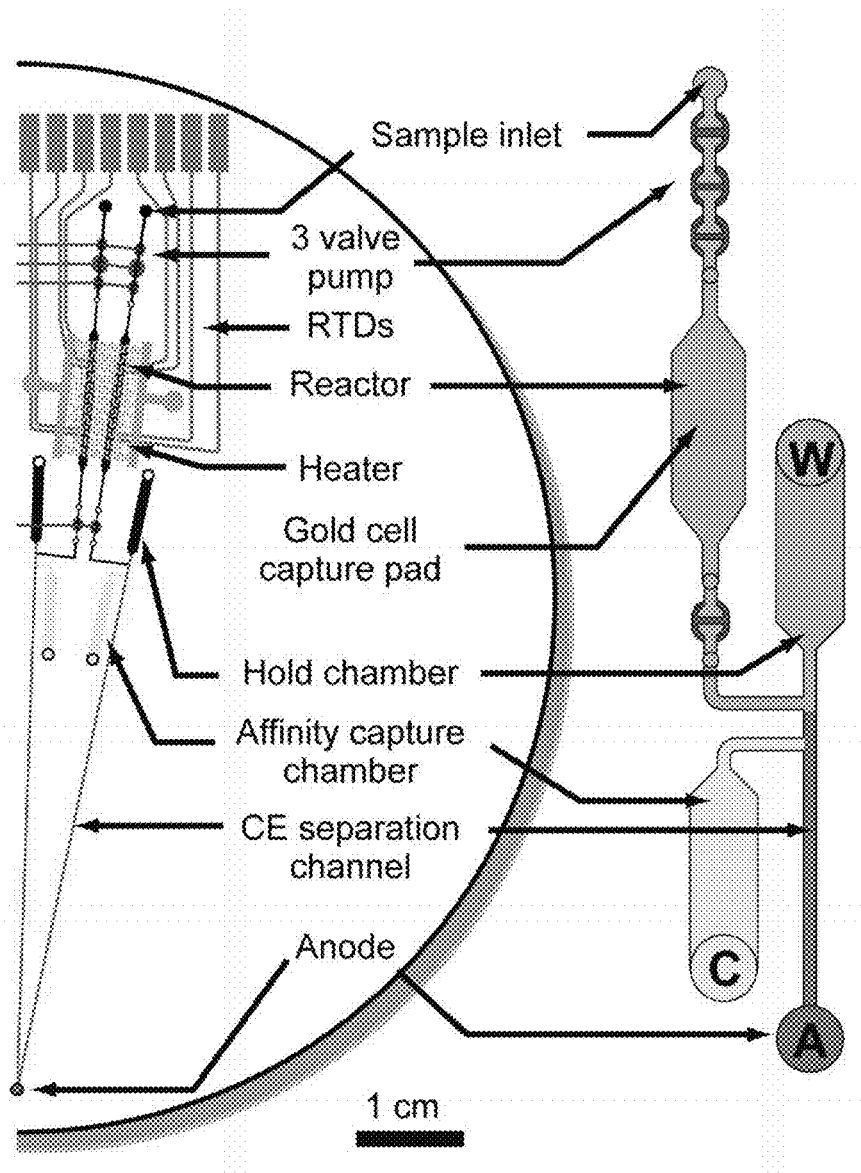
FIG. 21. Microfluidic device layout. Schematic showing half of the device (2 of the 4 complete systems) for single-cell gene expression profiling. The 4-layer glass-PDMS-glass-glass microdevice contains 4 distinct regions. The first region at the top is a 3-valve pump. The reactor region consists of a photolithographically defined gold cell-capture pad in the center of a 200-nL reaction chamber along with RTDs and a microfabricated heater for thermal cycling. The affinity capture region comprises a hold chamber and an affinity capture chamber (yellow). Finally, the thermally released amplicons are analyzed on the CE separation channel (red). Each device contains 4 independently addressable systems enabling the analysis of 4 single cells in parallel. All channels are etched to a depth of 20 μm FIG. 22. Schematic of the biochemical steps performed in the integrated gene expression microdevice. (Upper) The analysis is complete in <75 min. (Lower) (A) Depiction of the operation of the single-cell gene expression microsystem. (B) First, cells functionalized with a 20-base oligonucleotide on their cell membrane are flowed into the reactor. (C) A single cell is captured on a size-limiting 25-×25-μm² gold pad when the ssDNA on its exterior binds to the complementary capture strand immobilized on the gold pad. (D) The immobilized cell is freeze-thaw lysed, and mRNA is reverse-transcribed into a stable cDNA strand (15 min). PCR amplification (30 cycles) is completed in 25 min. (F) Amplified fragments and unreacted RT-PCR mixture are pumped from the reactor into the hold chamber and electrophoretically driven from the waste (W) to the cathode (C) reservoirs. (F) Fragments of interest with complementarity to the affinity capture probe are concentrated and immobilized at the entrance of the capture chamber creating a purified capture plug. (G) Finally, the products are thermally released at 80° C. from the affinity capture gel and electrophoretically separated as they migrate toward the anode (A).

The gene expression microdevice contains 4 independently addressable arrayed analysis systems on a 100-mm-diameter glass wafer (FIG. 21). Each of the identical microsystems contains 4 distinct regions that are integrated to enable maximal transfer efficiency between processing steps. The first region is a 3-valve pump for moving material from the sample inlet through the reactor region. In the reactor region, single cells are captured, lysed, and the mRNA of interest is reverse transcribed and amplified by RT-PCR. The affinity capture region comprises a hold chamber that acts as a reservoir and a capture chamber where amplicons are immobilized, purified, and concentrated in an affinity capture gel matrix. Finally, the system contains a CE separation channel for the size-based separation and quantitation of products.

The complete analysis from single-cell capture to CE separation and detection is performed in <75 min as outlined in FIG. 22A. First, Jurkat cells are functionalized with a 20-base oligonucleotide (FIG. 22B). Jurkat cells are grown with a synthetic peracetylated N-azidoacetylmannosamine ($Ac_4ManNAz$) sugar that is metabolized by the cell and results in the presentation of azido groups on the cells' surface. Phosphine-modified ssDNA is reacted with the azido group via Staudinger ligation, generating a population of cells functionalized with $\approx$270,000 ssDNA molecules per cell.

In another embodiment, ssDNA molecules can be attached to the Jurkat cells using the present methods as described in Example 1 as follows: Immediately prior to modification, a sample of $5\times10^6$ Jurkat cells are washed with PBS buffer three times to remove any proteins from the culture medium. After the final rinse, additional PBS is added to bring the volume to 5 mL ($1\times10^6$ cell/mL). The cell suspension is then reacted with 1 mL of NHS-DNA (11.7 µM) solution synthesized and purified from 30 µL of 5'-thiol ssDNA. The mixture is allowed to react at room temperature for 30 minutes, and is then washed three times with PBS containing 1% FBS. The cells are then resuspended in 0.5 mL of PBS containing 1% FBS Inside the reactor, the complementary 20-base strand of thiol-modified capture DNA is immobilized on a photolithographically defined 25-×25-µm² size-limiting gold pad with a gold-thiol linkage. Cells are flowed into the reactor and immobilized on the gold pad via DNA hybridization. The size of the pad ensures that only 1 cell will bind. In previous reports we have shown that the combination of metabolic engineering and DNA-based attachment leads to significantly less cellular activation than antibody or lectin-based methods. Thus, although any attachment method would be expected to have some effect on cell behavior, the DNA-based method minimizes these effects.

After washing the residual uncaptured cells out of the reactor, the captured cell is prepared for analysis (FIG. 22C). After a rapid 30-s freeze-thaw lysis, the target mRNA is reverse-transcribed into a stable cDNA strand during a 15-min incubation at 42° C. Then, 30 cycles of PCR amplification are completed in the same 200-nL reactor in 25 min. All RT-PCR products are then quantitatively transferred from the reactor to the separation channel for size analysis. Amplified fragments and unreacted RT-PCR mixture are pumped from the reactor into the hold chamber and electrophoretically driven from the waste to the cathode reservoir. Fragments of interest with complementarity to the affinity capture probe are quantitatively concentrated and immobilized at the entrance of the capture chamber, creating a purified capture plug. The affinity capture matrix comprises a linear polyacrylamide (LPA) gel copolymerized with two 20-base oligonucleotide capture probes complementary to the fragments of interest (20 µM). This capture process uses sequence-specific helix invasion to immobilize the dsDNA amplicons. The capture probes are complementary to sequences 23 and 47 bases from the end of the GAPDH and 18S rRNA amplicons, respectively. By placing the probes internal to the priming sites, the capture gel also acts as a purification matrix to remove unreacted high-molarity FAM-labeled primers. Finally, the purified and concentrated products are thermally released at 80° C. from the affinity capture gel, electrophoretically separated, and quantitated by confocal fluorescence detection (data not shown).

The integrated microfluidic gene expression analysis system yields quantitative data on the gene silencing of individual cells. As expected, the untreated Jurkat cells exhibit normal expression of GAPDH mRNA and 18S rRNA (FIG. 23A). The representative electropherogram shows 2 strong peaks migrating at 160 s and 185 s for the 200-bp GAPDH and the 247-bp 18S rRNA targets, respectively (FIG. 23). Moreover, the use of the capture matrix to immobilize the fragments of interest removes all unreacted primers from the separation, enabling us to look at both small and large amplicons without interference. A single Jurkat cell electroporated with siRNA directed at GAPDH mRNA produces only a single peak for 18S rRNA at 185 s. Single-cell experiments from 8 individual cells show expression of the GAPDH mRNA at 0, 5, 50, 1, 48, 0, 5, and 0% of untreated Jurkat cells (FIG. 23B). This analysis indicates that single cells fall into populations with moderate (≈50%) or complete silencing (≈0%). These single-cell measurements differ fundamentally from a bulk measurement performed on 50 Jurkat cells under the same conditions where the expression of GAPDH is reduced to 21±4% (n=4) of its original value. Thus, the ensemble average measured for gene silencing masks the stochastic diversity of individual cellular response. A control assay where no cell is captured on the pad exhibits no products, verifying that there is no carryover contamination in the system. Similarly, a PCR control without reverse transcriptase shows no amplification, ensuring that the amplification template is RNA and not DNA.

To ensure that the variation in silencing behavior is not a simple function of the amount of siRNA introduced during the electroporation process, cells were treated with a fluorescently labeled siRNA. Cells grown under normal conditions showed an average uptake of the Cy3-labeled siRNA of 17±2 relative fluorescence units (rfu) (Table S1) with 4 of 30 cells appearing at a slightly elevated level of 22 rfu. If electroporation variability were the cause of the 2 cellular populations, we would expect 13% of the cells to be characterized as completely silenced and 87% as moderately silenced. The single-cell gene expression analysis performed in the microfluidic device shows the opposite trend (FIG. 23B).

TABLE S1

Tabulated data from single-cell siRNA electroporation experiment

| Cell no. | Minimum | Maximum | Difference, rfu |
|---|---|---|---|
| 1 | 26 | 41 | 15 |
| 2 | 25 | 42 | 17 |
| 3 | 26 | 41 | 15 |
| 4 | 25 | 40 | 15 |
| 5 | 25 | 42 | 17 |
| 6 | 25 | 48 | 23 |
| 7 | 26 | 40 | 14 |
| 8 | 25 | 40 | 15 |
| 9 | 25 | 41 | 16 |
| 10 | 26 | 44 | 18 |
| 11 | 25 | 43 | 18 |
| 12 | 25 | 41 | 16 |
| 13 | 24 | 39 | 15 |
| 14 | 24 | 40 | 16 |
| 15 | 24 | 42 | 18 |
| 16 | 24 | 46 | 22 |
| 17 | 24 | 42 | 18 |
| 18 | 24 | 42 | 18 |
| 19 | 25 | 42 | 17 |
| 20 | 25 | 44 | 19 |
| 21 | 26 | 43 | 17 |
| 22 | 26 | 42 | 16 |
| 23 | 26 | 44 | 18 |
| 24 | 26 | 40 | 14 |
| 25 | 24 | 40 | 16 |
| 26 | 24 | 39 | 15 |
| 27 | 24 | 46 | 22 |
| 28 | 21 | 37 | 16 |
| 29 | 22 | 44 | 22 |
| 30 | 23 | 40 | 17 |
| | | Average: | 17.2 |
| | | SD: | 2.4 |

Cells were electroporated with Cy3-labeled siRNA and grown under normal conditions and imaged with epifluorescence. Each cell is interragated, and the maximum pixel intensity value is recorded in addition, a minimum value is recorded from just outside each cell for normalization. The average update is 17.2 ± 2.4 relative frequency units (rfu). The maximum update is 23 rfu, and the minimum is 15 rfu.

In addition, the GAPDH gene was sequenced to examine whether the population of cells experiencing moderate silencing arises from a heterozygotic polymorphism in the siRNA-binding domain. The sequence was found to be without mutation. The sequencing result of GAPDH siRNA binding sequencing showed that the expected sequence (5'-AAA GTT GTC ATG GAT GAC C-3'; SEQ ID NO:11) was found in the Jurkat cells, suggesting that the 2 populations of cells are not a result a polymorphism in the binding domain. Thus, the 2 populations of cells revealed here are not a trivial result of siRNA delivery, genetic variation, or cell viability.

The occurrence of 2 distinct cellular populations with different levels of gene silencing has been detected by Liu Y P, Dambaeva S V, Dovzhenko O V, Garthwaite M A, Golos T G. Stable plasmid-based siRNA silencing of gene expression in human embryonic stem cells. *Stem Cells Dev.* 2005; 14:487-492. Measurements of enhanced green fluorescent protein production in human embryonic stem cells (hESCs) have shown an all-or-nothing response to siRNA treatment, but the underlying mechanism was not characterized. Our system demonstrates the unique ability to perform quantitative transcript analysis, revealing that although 80% of the cells exhibited the expected complete inhibition, 20% exhibited 50% inhibition. This suggests the presence of a genetic or phenotypic bistability or switch that controls the degradation of the siRNA, blocks its target binding, or inhibits transcript degradation. Of these only the latter 2 mechanisms would provide a nontrivial explanation for the 50% inhibition level. A more exhaustive study is now called for to verify the biphasic expression trend observed here and to explore its mechanistic origin. Because the fabrication of highly parallel structures is one of the key advantages of our approach, scaling up to 96-analyzers would provide the throughput necessary for this type of study.

Our ability to perform 1-step RT-PCR amplification in our expression microdevice with only 30 cycles of PCR in a single reactor is a direct result of efficient integration. First, the use of glass rather than porous polymeric materials prevents product absorption. Second, the high thermal conductivity of glass enables rapid thermal cycling and increased reaction efficiency. Third, the use of pneumatic valves and pumps allows for the efficient transfer of nanoliter bolus material. Finally, the affinity capture, purification, and concentration process enables the quantitative analysis of all generated products, a dramatic improvement over the use of a traditional cross-injector or hydrodynamic pressure injector, which only permits a small portion (<1%) of the products to be analyzed. These advantageous attributes of our integrated device point the way to a wide variety of bioanalytical studies on the properties and behavior of single cells.

Here, we have performed single-cell measurements on the variation of mRNA knockdown as a result of siRNA treatment. This assay suggests a unique biphasic gene knockdown efficiency in individual cells that was masked by bulk measurements. Because the analysis step utilizes a size-based separation, the multiplex capabilities are determined by the number of products that can be generated and analyzed, suggesting that the expression of 5-10 targets could be studied in parallel. By coupling this microdevice with laser capture microdissection, the heterogeneous nature of tumors could be investigated at the single-cell level. It should also be possible to perform a quantitative single-cell analysis of the effects of siRNA treatment on expression in hESCs when Oct4 mRNA targeting is used to trigger differentiation into trophoblast-like cells. Moreover, based on our previous detection of <11 mRNA molecules per reactor, our microfluidic device may ultimately enable studies of expression from individual cells at the single-transcript level, once improved product capture, purification, and injection processes are fully enabled and integrated. Overall, our approach offers many exciting prospects for revealing the stochastic variation in gene expression that underlies the ensemble average.

Materials and Methods. Bioprocessor Fabrication.

The fabrication protocol is similar to that used in previous nucleic acid amplification microdevices, Toriello N M, Liu C N, Mathies R A. Multichannel reverse transcription-polymerase chain reaction microdevice for rapid gene expression and biomarker analysis. *Anal Chem.* 2006; 78:7997-8003 and hereby incorporated by reference. Briefly, to form the pneumatic manifold wafer, valve seats and actuation channels were photolithographically defined and etched to a depth of 38 µm on a 0.5-mm-thick borofloat 100-mm glass wafer. Valve actuation access holes were drilled, and the manifold was diced into reusable 9-mm×6-cm strips. Removable polydimethylsiloxane (PDMS) elastomer valves were formed by activating both sides of the 254-µm PDMS membrane with a UV ozone cleaner for 1.5 min to improve PDMS-glass bonding and then sandwiching the membrane between the manifold and the bonded channel wafers.

The reactor/channel wafer was fabricated on a 0.5-mm-thick borofloat glass wafer. Fluidic channels for pumping were photolithographically defined on the front side and etched to a depth of 38 µm. Reaction, hold, and capture chambers along with separation channels were photolithographically defined on the back side and etched to a depth of 20 µm. Electrophoresis reservoirs, resistance temperature detection (RTD) access holes, and valve via holes were diamond drilled. To form the RTD wafer, a 0.5-mm-thick borofloat glass wafer sputter deposited with 200 Å of Ti and 2,000 Å of Pt (Ti/Pt; UHV Sputtering) was photolithographically patterned and etched with 90° C. aqua regia to form the 30-µm-wide RTD elements and 300-µm-wide leads. The drilled reactor/channel wafer was aligned and thermally bonded to the RTD wafer by using a programmable vacuum furnace at 655° C. for 6 hours.

To form the removable modular heater, a 0.5-mm-thick borofloat glass wafer was sputter-deposited with 2,200 Å of Ti/Pt. Heater leads were formed by electroplating 6 µm of gold onto photolithographically defined areas. Ti/Pt serpentine resistive heater elements connecting the gold leads were formed by anisotropically etching photolithographically exposed Ti/Pt in an ion mill.

Jurkat Cell Preparation.

T lymphocyte Jurkat cells were cultured in 50-mL flasks (Nalge-Nunc International) for 48 h in 10 mL of medium (RPMI medium 1640; Invitrogen) containing 1% penicillin/streptomycin (1% P/S; Invitrogen) and 25 µM $Ac_4ManNAz$ resulting in the display of N-azidoacetylsialic acids on the cell surface glycans. For the first 24 h of growth, the cells were cultured with 10% FBS (JR Scientific). The Jurkat cells were washed and incubated in serum-depleted medium containing 25 µM $Ac_4ManNAz$ for an additional 24 h for synchronization. Fresh DNA-functionalized Jurkat cells were prepared 1 h before the analysis. Cells were washed twice with 5 mL of PBS (Ambion) containing 1% FBS and reacted with 125 µM phosphine-modified ssDNA (5'-phos-GTA ACG ATC CAG CTG TCA CT-3'; SEQ ID NO:12) in 1% FBS/PBS for 1 h at 37° C. The cells were then rinsed 3 times with 5 mL of 1% FBS/PBS solution before introduction into the microfluidic device.

siRNA Treatment.

For gene-silencing studies, 150,000 Jurkat cells were electroporated with 2.5 µg of double-stranded GAPDH siRNA (sense, 5'-GGU CAU CCA UGA CAA CUU UdTdT-3' (SEQ ID NO:13); Ambion). Cells were suspended in 75 µL of siPORT electroporation buffer (AM1629; Ambion) and a single pulse is performed in a 1-mm cuvette (Bio-Rad) for 250 µs at 250 V. Cells were then grown and prepared in the same manner as described in the Jurkat cell preparation section above. For negative control studies, cells were electroporated with 150 pmol of Cy3-labeled siRNA that does not bind to mRNA.

RT-PCR Mixture.

Multiplex RNA RT-PCR was performed on GAPDH and 18S rRNA transcripts directly from Jurkat cells. A 25-µL, RT reaction mixture comprises a Cell-to-cDNA II kit [4 units of Moloney murine leukemia virus (Mo-MLV) reverse transcriptase, 0.4 unit of RNase inhibitor, 0.1 µM dNTPs, 1×RT buffer (Ambion)], 0.08 unit of platinum Taq polymerase (Invitrogen), along with 800 nM forward and reverse primers for the GAPDH gene and 20 nM forward and reverse primer for the 18S rRNA target. The GAPDH forward (5'-AGG GCT GCT TTT AAC TCT GG-3'; SEQ ID NO:14) and reverse (5'-FAM-TTG ATT TTG GAG GGA TCT CG-3'; SEQ ID NO:15) primers generate a 200-bp amplicon. The 18S rRNA forward (5'-CGG CTA CCA CAT CCA AGG AAG-3'; SEQ ID NO:16) and reverse (5'-FAM-CGC TCC CAA GAT CCA ACT AC-3'; SEQ ID NO:17) primers generate a 247-bp amplicon. Controls without RT and without template were performed on the microdevice by removing the Mo-MLV RT and Jurkat cells from the reaction mixture, respectively.

Matrix Synthesis.

A DNA affinity capture gel is synthesized by copolymerizing LPA with 2 5'-acrydite-modified capture oligonucleotides. The affinity capture matrix is synthesized at 4° C. by sparging a 2-mL solution containing 6% wt/vol acrylamide, 1×TTE, and 40 nmol of the 2 acrydite-modified oligonucleotides (IDT) for 2 h with argon followed by the addition of 0.015% wt/vol ammonium persulfate (APS; Fisher Scientific) and tetramethylethylenediamine (TEMED; Fisher Scientific). The affinity capture matrix contains capture probes for GAPDH (5'-Acry-ATC CCA TCA CCA TCT TCC AG-3' (SEQ ID NO:18), $T_M$=54.2; 50 mM monovalent salt, 20 μM) and 18S rRNA (5'-Acry-GCA GCC GCG GTA ATT CCA GC-3' (SEQ ID NO:19), $T_M$=61.9; 50 mM monovalent salt, 20 μM). The GAPDH capture oligonucleotide is complementary to a 20-base sequence in the 200-bp amplicon, 23 bases from the 5' FAM-labeled terminus. The 18S rRNA capture oligonucleotide is complementary to a 20-base sequence in the 247-bp amplicon, 60 bases from the 5' FAM-labeled terminus.

Reactor Preparation.

The glass surface is derivatized with polydimethylacrylamide (PDMA) by using a modified Hjerten coating protocol to prevent nonspecific cell adhesion. First, the reactors glass surface is deprotonated by incubating with 1 M NaOH for 1 h. The NaOH solution is replaced with a 0.6% (vol/vol) (γ-methacryloxypropyl)trimethoxysilane solution (γ, Sigma) in 3.5 pH $H_2O$. The bifunctional γ-solution prepares the glass surface for acrylamide polymer nucleation. During γ-solution incubation, 250 μL of dimethylacrylamide is dissolved in 4.75 mL of $H_2O$ and sparged with Ar for 1 h. After Ar sparging, 100 μL of isopropyl alcohol (IPA), 20 μL of TEMED, and 25 μL of 10% (vol/vol) APS were sequentially added to the acrylamide solution to form linear PDMA. The γ-solution is removed from the channel, and PDMA solution incubates in the channel for 1 h. The channel is then rinsed and dried with acetonitrile.

Next, the photolithographically defined 25-μm×25-μm gold pad in the center of the reaction chamber is functionalized with ssDNA by incubating for 1 h with Tris(2-carboxyethyl)phosphine (TCEP, 200 μM; Invitrogen) deprotected thiol-DNA (5'-thiol-AGT GAC AGC TGG ATC GTT AC-3' (SEQ ID NO:20), 20 μM). The chamber is then rinsed and dried to remove unbound DNA.

Gel Loading Sequence.

The device is prepared for affinity capture and separation by treating the separation channels, hold chambers, and capture chambers with a dynamic coating diluted in methanol for 1 min (1:1; DEH-100; The Gel Company) to suppress electroosmotic flow. Multiplex affinity capture matrix (20 μM, 6%, yellow) is loaded from each cathode (C) reservoir up to the separation channel cross at room temperature. Separation matrix (red) is then loaded from the central anode (A) past the capture chamber to the sample load cross. With all of the valves opened, the rest of the system is hydrated by adding 3 μL of RNase-free water at the sample ports and applying a vacuum at the waste (W) reservoirs. The microdevice is then placed on a 44° C. temperature-controlled stage. An additional 2 μL of water is flushed through the system to remove thermally expanded gel from the sample load cross.

Bioprocessor Operation.

Figure 22:
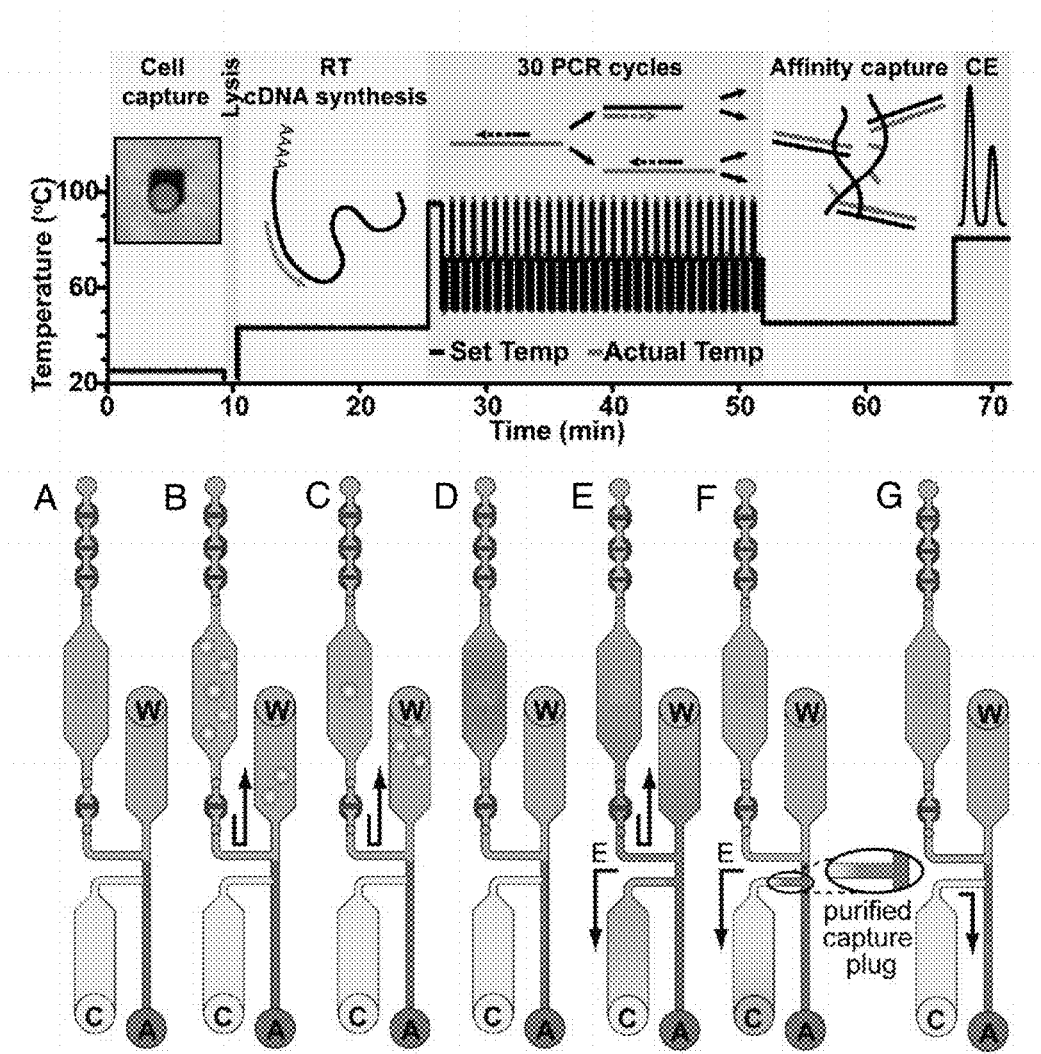

As depicted in FIG. 22, the microdevice operation begins by preparing the reaction chamber for cell capture. Cell modified to contain ssDNA on their surface were suspended in the reaction mixture and drawn into the reaction by vacuum. When a cell flows over the gold cell capture pad, DNA hybridization occurs between the ssDNA on the surface of the cell and the complementary ssDNA immobilized on the gold pad. To maximize capture efficiency, DNA-mediated cell capture was performed for 15 min. The uncaptured cells were washed out of the system and removed at the waste port, and the valves were closed for thermal cycling. During this study, all 4 reactors were used in parallel. This enabled simultaneous analysis from 4 individual cells. After capture, the morphology of each cell is recorded to ensure that it has remained viable. The total data collection time for the single-cell studies was 1 month.

Freeze-thaw lysis and 1-step RT-PCR thermal cycling were performed in a single 200-nL reactor. A piece of dry ice was placed over the reaction chambers of all 4 reactors for 30 s to freeze-thaw lyse the captured Jurkat cell. Freeze-thaw lysis was used in this 1-step RT-PCR to prevent early unwanted activation of the Hot Start Taq polymerase, to prevent denaturation of the reverse transcriptase enzyme, and to minimize RNA degradation by RNases. Next, a linear 15-min cDNA synthesis from the cells' RNA was performed at 42° C. by using primers complementary to the RNA transcripts of interest (GAPDH and 18S rRNA). After cDNA synthesis, the Mo-MLV RT was denatured, and the platinum Taq polymerase was activated at 95° C. for 60 s followed by 30 cycles of PCR at 95° C. for 5 s, 47° C. for 20 s, and 72° C. for 25 s. Because of the rapid heating and cooling rates (>15° C. $s^{-1}$), each cycle of PCR is completed in 50 s, and the total reaction time is 46 min.

After thermal cycling, affinity capture, purification and concentration of the products of interest were performed. The reactor contents were pumped into the hold chamber by using a 5-step pump cycle. A 350-ms actuation was used with each step, resulting in a 30-nL stroke volume. A 23-s delay was used between each pump cycle to allow sufficient time for the analyte to migrate into the capture region and to prevent analyte accumulation in the hold chamber. A constant 100-V/cm field between the waste (W) and cathode (C) reservoirs electrophoretically drives the analyte toward the capture chamber. Analytes complementary to the capture probe were hybridized at the entrance of the capture chamber, creating a sample plug. The electric field between the waste and cathode was maintained until residual PCR reactants (excess primer, salts, and buffer) were washed into the cathode reservoir thus resulting in a purified amplicon sample plug. Thirty pump cycles were used resulting in a total capture and wash time of 12.2 min. After the capture process was completed, the temperature of the entire device was raised to 80° C. to thermally release the captured DNA fragments thermally from the affinity capture gel, and the sample was separated with a field of 150 V/cm between the cathode and the anode. The electrophoretically separated FAM-labeled products from all 4 lanes were detected by using laser-induced fluorescence with the Berkeley rotary confocal scanner (Shi Y N, et al. Radial capillary array electrophoresis microplate and scanner for high-performance nucleic acid analysis. *Anal Chem.* 1999; 71:5354-5361). The entire capture and release process was performed on a temperature-controlled stage on the scanner to prevent thermal gradients.

Example 7. Patterning of Single Algal or Bacterial Cells for Bioreactor or Fuel Cell Using the principles of the invention as applied to oligonucleotide attachment on non-animal cells through an aldehyde or ketone on a carbohydrate, hydrogen production efficiency can be studied and optimized. The oligonucleotide capture and attachment to a device allow the creation of patterned cells and enzymes on a chip. In the system, conversion of hydrogen gas to electricity measures hydrogen production. Measuring direct hydrogen production via current generation is advantageous because of potentially higher sensitivity to hydrogen production compared to conventional measurements (see GC readings of culture headspace). The advantage of the invention to such studies and actuation include the attachment and control implicit with precise placement of the cells on the device, that the fuel cell can then be reusable, and also higher efficiency in utilization of solar and carbon energy For example, a self-sustaining fuel cell device can be constructed using patterned layers of different photosynthetic cells, where the cells absorb sunlight in non-overlapping parts of the solar spectrum, and also incorporating alternating layer(s) of nitrogen-fixing organisms which feed on and utilize the biomass created by the photosynthetic cells in adjacent layers. When exhausted, the fuel cell having the cells attached by oligonucleotide hybridization can be heated, the oligonucleotides dehybridize, and dead cells wash away. The surface is rinsed over with fresh modified cells which reattach to complementary oligonucleotides on the device surface. However, sol gel devices having solgel embedded cells are discarded and cannot be reused in the same manner, but this turnover may be appropriate to their targeted application.

Optimized bacterial and algae cell patterning is accomplished using suspended cells in 5 mM $NaIO_4$ in DPBS for 20 minutes, at 37 degrees centigrade. After rinse with DPBS, the cells are resuspended in 10 mM aniline in pH 6.0 MOPS buffer and 35 μM I-linker-DNA (from IDT, I linker is a hydrazide linker) for 2 hours. The cells are rinsed, incubated or centrifuged (1% FBS) to complementary patterned DNA for several minutes. In addition, to other advantages already stated, when using oligonucleotide captured cells and exposing them to sunlight as a source of energy for bioreactor, bioactivity, metabolic, and fuel cell electricity production, and other such similar uses, the invention provides the opportunity to arrange the cells in a monolayer or multiple layers, each cell having direct access to the solar fuel source. In turn, this allows the opportunity to employ lower intensity light.

Other experiments and uses of the system are to optimize a design for a proton exchange membrane hydrogen fuel cell on a chip. Additionally, porous polymer must be used to prevent poisoning of the platinum/palladium by nitrogenous bases and cell waste. To determine hydrogen output efficiencies in permutations of such a system, current generated per unit time is measured.

Hydrogen output efficiency of different photosynthetic and non-photosynthetic microorganism combinations can be studied on the path towards increasing system efficiency. Parameters such as the patterns of the organisms on the device, light exposure, and specific combinations of organisms in patterns can be varied to optimize efficiency. For example, a three organism hydrogen production system proposed by Melis lab (two photoautotrophs that absorb different regions of solar radiation and one heterotroph that takes the biomass created by the photosynthesis and converts it to small organic acids which the photosynths need for autotrophic growth) can be adopted. Proposed organisms include but are not limited to, Photosynthetic: *C. reinhardtii* (algae), *Synechocystis* PCC 6803 (cyanobacteria), *R. rubrum* (gram negative anaerobe); Heterotrophs: *C. pasteurianum* (nitrogen fixer), *Azotobacter* sp. (proposed to have the highest respiration rate of any organism). (see Melis et al, cited elsewhere herein).

In another embodiment, the fuel cell device comprising an open air cathode instead of solution-based reduction at the cathode, and an anode patterned with bacteria directly on the anode. This will be done by coating the anode with LPA (linear polyacrylamide) modified with streptavidin (available through invitrogen). The coating will also act to protect the Pt from poisoning by nitrogenous waste from the cells. 5'-biotin modified DNA will be patterned on the LPA coated electrodes using aluminum liftoff lithography patterning. So, the glass electrode base will be fabricated first then the DNA will be patterned on the electrodes, finally the cells will be patterned on the electrode and the PDMS top will be bonded on. There will constantly be a very slow flow of media into the cell because hydrogen production is greatest during log phase growth and when nutrients are plentiful. The device will be illuminated and the photosynthetic hydrogen production can be measured for example, by a voltage drop over a resistor with some sort of a bias placed on the cell.

In a fuel cell device, the hydrogen gas will nucleate on the Pt electrode and as with most fuel cell designs, the electrons will be removed, immediately converting the hydrogen produced by the cells into electricity.

Another interesting aspect of patterning is using the DNA to pattern the cells on top of each other for use in a fuel cell device. Referring now to FIG. 30, multiple cells can be patterned on top of each other on a DNA microarray. Each cell is labeled with a different fluorophor, except the cyanobacteria *Synechocystis*, which auto-fluoresces red. A schematic of the cells and what fluorophor they are labeled is shown in FIG. 30. The advantage is that the spatial orientation of the oxygen absorbing cell (*A. vinelandii*) sandwiched between the two photosynthetic cells will be potentially useful in keeping oxygen concentrations low in the local vicinity of the photosynthetic cells. Since photosynthesis generates oxygen (at least in the case of algae and cyanobacteria) as a byproduct and the enzymes which make hydrogen are inhibited by oxygen, having the photosynthetic cells tethered to a cell with an incredibly high metabolism means that local oxygen concentration should always be low and hydrogen production will be sustained. Currently, *Synechocystis* does not do well at long term $H_2$ production due to the oxygen inhibition of its hydrogenase enzymes. The presently anticipated experiments should show that cultivating the cells together can be done (such as *A. vinelandii* and *Synechocystis* co-cultures, *A. vinelandii* and *R. rubrum* co-cultures, or all three cultured together) and show that these cultures have amiable hydrogen evolution and lower concentrations of oxygen present than if the cells were cultured alone.

$O_2$ and $H_2$ gas concentration can be measured using gas chromatography. Upon building the device and it can be tested using one cell type (e.g., *R. rubrum*) to show it can work as a hydrogen fuel cell. The final experiment will be investigating how two and three dimensional patterning will effect the electrical output (synonymous with $H_2$ production) of the cell when using 2 or more cell type combinations.

The strands used to modify each cell do not complement any other strands on the other cells or glass to insure that the cells are patterned correctly. The same oligonucleotides used in the previous examples (M1/C1, M2/C2, M3/C3) and two other complementary sequences Z2 (5' CACACACACA-CACACACACA 3'; SEQ ID NO:21) and zc2 (5' TGTGT-GTGTGTGTGTGTGTG 3'; SEQ ID NO:22) can be used to pattern these cells onto the glass substrate. The cells are patterned one layer at a time. The cells are oxidized in 5 mM sodium periodate and then incubated in ~35 µM hydrazide-DNA at pH 6 in MOPS (N-morpholino propane sulfonic acid) buffer (note that MOPS is being used in this experiment outside its normal buffering range). After washing the cells, they are reversibly bound to a PDMS well on the glass substrate which has been previously modified with DNA. The well is filled with one cell solution, centrifuged at 3000 rpm for 5 min, rinsed in PBS and repeated with the next two or three cell types sequentially. The DNA should not dehybridize under these conditions allowing the cells to be patterned as shown in FIG. 30. The cell types chosen are not limited to those shown, but multiple layers of patterned cells can be added using the present methods. For example, referring now to FIG. 30, the glass can be modified with M2 oligonucleotide. The layer of *Synechocystis* cells are attached to the glass substrate through the C1 oligonucleotide. This *Synechocystis* layer is then modified with the C2 oligonucleotide. The *A. vinelandii* cells are modified with M2 oligonucleotide and are attached to the first *Synechocystis* layer through M2/C2 hybridization. Layer two of *A. vinelandii* cells are modified with M2 and C3, and the third layer of *R. rubrum* cells are modified with M3 and which then hybridize to the M2 oligonucleotide and link the third layer to the second layer of cells.

Patterning should be carried out under sterile conditions and then placing the pattern in media in which all of the cells can grow and in a vial with a small amount of head space. $H_2$ production could be monitored by taking samples from this headspace over time and monitoring activity. The system will require a medium in which all three or two or however many cell types are patterned can live and a light source, such as sunlight or a fluorescent or tungsten bulb is sufficient. In the device a slow flow of media is provided into and out of the chamber where the cells are patterned on the electrode. No gas will be needed to maintain the system. However, nitrogen gas will be used to sparge the system when starting the fuel cell in order to create an anaerobic environment.

Any medium can be used which contains the same nutrient concentrations necessary in each cell's individual medium but in the volume of one medium. For instance, *Synechocystis* uses a medium called BG11 and *A. vinelandii* lives in Burk's medium so a cocultivation medium containing all of the nutrient ingredients in 1 L of BG11 and 1 L Burk's medium but in a single volume (1 L) is made, thereby providing a higher concentration of nutrients per liter compared to the individual medias. *R. rubrum* uses a medium ORMERODs so when a culture for all three organisms will have all of the ingredients (minus the phosphate for buffering) for 1 L of each culture in 1 L of cocultivation medium making a three media in one high nutrient media. The phosphate buffer recipe from the Burk's medium can be used to optimize the phosphate concentration.

The device would work for powering things which are outside constantly. When the cells die the device is heated up, the DNA dehybridizes, the dead cells wash out, and fresh cells are washed in to replace the old ones. The device could also act as a battery or an addition to the powergrid. In theory, many of the devices could be wired in series to potentially power vehicles or could act synonymously with Si solar panels.

Example 8. AFM Patterning

The forces governing cell-cell adhesion are vitally important to many biological processes, including cell differentiation, tissue growth, tumorigenesis, and proper functioning of the vertebrate immune response. The strengths of these interactions are typically characterized through the attachment of single living cells to probes that are capable of force measurement, such as suction micropipettes. More recently, optical tweezers have been applied to capture single cells and to measure these forces with high accuracy, but this technique is limited to applying forces in the piconewton range. Atomic force microscopy (AFM) provides an attractive alternative to these methods, because it is capable of quantifying forces in the piconewton to nanonewton range, and this technique has indeed been used to measure the mechanical properties of live single cells and to study adhesion forces at the single-cell level. Several fundamental adhesion measurements have been achieved by coating AFM cantilevers with fibronectin or lectins that bind to carbohydrate moieties on the cell surface, but especially in the latter case the cell-binding molecules themselves have been reported to have a degree of cytotoxicity that can influence the cellular properties being evaluated. Thus, while these studies highlight the utility of AFM for the measurement of cell receptor-ligand interactions, an expanded set of cantilever attachment methods will be needed for the study of cell-cell interactions over widely varying time scales.

To address this need, we have compared three biomolecule-mediated methods for the attachment of live cells to AFM cantilevers, with an emphasis on the cell viability, adhesion strength, and probe reuse that each technique can achieve. These studies have indicated that cell attachment through the use of complementary DNA strands has the least influence on viability and does not appear to activate cell signaling pathways. This method also offers overall superior adhesion strength, but this parameter can be attenuated to allow cells to be transferred from one surface to another. We were able to demonstrate this concept by picking up free cells and placing them in exact positions on a substrate bearing DNA strands with longer complementary regions. This "dip-pen" live-cell patterning demonstrates the reusability of the DNA-mediated cell adhesion method and could prove useful for the construction of complex mixtures of cells with well-defined spatial relationships.

To allow the comparison of several attachment strategies, three different biomolecules (DNA, concanavalin A (ConA), and an antibody) were attached to silicon nitride AFM cantilevers for cell anchoring. For all attachment methods, the thin layer of silicon oxide on the working surface was covered with aldehyde groups as outlined in FIG. 16*a*. The surfaces produced using these steps were characterized by contact-angle measurements.

Figure 16:
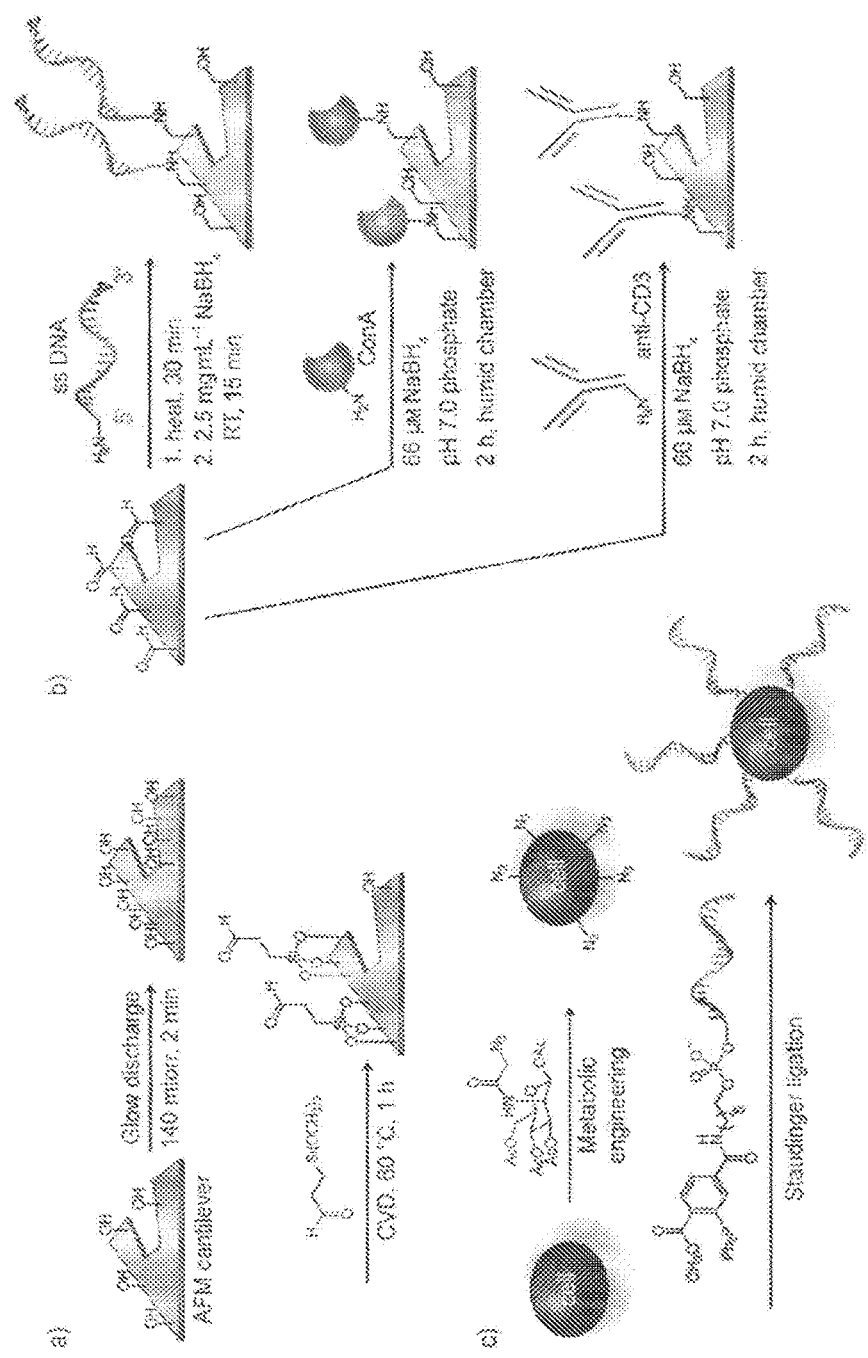
FIG. 16. Covalent attachment of biomolecules to cantilevers and cell surfaces. a) After surface oxidation using an oxygen plasma, aldehyde functional groups were introduced onto silicon nitride cantilevers using chemical vapor deposition (CVD). b) Solutions of anti-CD3 IgG or ConA containing sodium borohydride were introduced onto aldehyde-coated cantilever surfaces in a humid chamber (IgG=immunoglobulin G). DNA modification was achieved by immersing cantilevers in an amine-functionalized ssDNA solution at 100° C. for 30 min and subsequent exposure to a sodium borohydride solution. c) Metabolic engineering was used to introduce azide groups onto cell surfaces by treatment with peracetylated N-azidoacetylmannosamine ($Ac_4ManNAz$). Phosphine-functionalized ssDNAs were synthesized and covalently attached to the exterior of cells by Staudinger ligation.

Amine-functionalized DNA was attached to the aldehyde groups through reductive amination (FIG. 16*b*). First, the aldehyde-coated cantilever was immersed in an amine-functionalized single-strand DNA (ssDNA) solution and then heated to promote imine formation. After cooling to room temperature, an aqueous solution of sodium borohydride was used to reduce the imines to nonhydrolyzable amine linkages. This step also served to reduce any unreacted aldehyde functional groups to alcohols. By coupling 5'-amine-functionalized DNA strands bearing fluorescein isothiocyanate (FITC) at the 3' end, the presence of the strands could be verified by fluorescence imaging.

In previous efforts, proteins have been attached to AFM tips through nonspecific adsorption and through glutaraldehyde crosslinking to amine groups introduced on the tip surface. To afford more well-defined linkages (and thus realize more homogeneous cell attachment), we chose instead to use the simple reductive amination strategy that was used for the amino-DNA strands. Surface lysine residues on ConA and anti-human CD3 antibodies (anti-CD3) were reacted with the aldehyde functional groups on the cantilever surfaces (FIG. 16b), but a lower concentration of reducing agent (66 µM) was used to minimize the reduction of disulfide bonds that are required to maintain protein tertiary structure. The concentrations of the proteins (20 µM ConA and 6 µM anti-CD3) used in the reactions are easily achieved using commercially available samples. As described above for DNA, FTIC-labeled ConA and anti-CD3 samples were used in some experiments to verify biomolecule attachment using fluorescence microscopy. Similar levels of fluorescence were detected for each.

For the covalent attachment of DNA, lectins, and antibodies to cantilevers, the following methods were used. For DNA-mediated cell adhesion studies, a complementary oligonucleotide sequence pair (A/A') was designed. The sequence identities were as follows:

```
A:
                                 (SEQ ID NO: 23)
5'-TCA TAC GAC TCA CTC TAG GG-3'

A':
                                 (SEQ ID NO: 24)
5'-CCC TAG AGT GAG TCG TAT GA-3'
```

An aldehyde-coated cantilever (MLCT-NONM) was immersed into a 20 µM solution of 5'-amine functionalized ssDNA in 3× saline/sodium citrate buffer (45 mM sodium citrate, 450 mM NaCl, pH 7.0) for 15 min, heated in an oven at 100° C. for 30 min, and then washed with 0.2% SDS solution and distilled water (1 min each). The resulting cantilever was soaked in a fresh solution of 0.1 g of NaBH4 in 10 mL of ethanol and 30 mL of PBS solution for 15 min, and then it was washed with 0.2% SDS solution and water (1 min each). The cantilever was dried under N2 and stored in a low moisture environment until use. The ssDNA coated cantilever was characterized by coupling 3'-FITC-labeled 5'-amino ssDNA (A strand) to the aldehyde-coated cantilever surface, followed by imaging with a fluorescence microscope.

Concanavalin A and anti-CD3 IgG monoclonal antibodies were also coupled to an aldehyde-coated cantilever (MLCT-AUNM) surface by a reductive animation procedure. An aldehyde-coated cantilever was exposed to a 20 µM (Con A) or 1 mg/mL (Anti-CD3) solution of the protein in pH 7.0 PBS buffer solution containing 66 µM NaBH4 in a humid chamber for 2 h. The cantilever was then washed with excess PBS and water, and stored in pure PBS solution at 4° C. until use.

To prepare live cells bearing ssDNA on their surfaces, we first introduced azide functional groups into glycoproteins embedded in the plasma membrane, as previously described [Zabzdyr J L, Lillard S J. Measurement of single-cell gene expression using capillary electrophoresis. *Anal Chem*. 2001; 73:5771-5775]. Peracetylated N-α-azidoacetylmannosamine (Ac$_4$ManNAz) was added to cells, which then metabolized and displayed the azide on their surfaces (FIG. 16c). Triarylphosphine-modified ssDNA was prepared through the reaction of 5'-amine-modified ssDNA with a phosphine pentafluorophenyl (PFP) ester. This reagent was then used to label the cell-surface azide groups through Staudinger ligation, yielding stable amide linkages. Flow cytometry experiments have previously verified the ability of phosphine-DNA conjugates to undergo ligation to azide-modified cell surfaces. Although many cell types would be expected to be compatible with this system (and have been explored previously using the DNA-based adhesion method), non-adherent Jurkat cells were chosen for these studies, because they do not secrete their own extracellular matrix. Thus, all cell adhesion events arise solely from the biomolecules on their surfaces In other studies, to prepare live cells bearing ssDNA on their surfaces, the general protocol for the attachment of DNA strands to cells can be carried out. Immediately prior to modification, a sample of 5×10$^6$ Jurkat cells are washed with PBS buffer three times to remove any proteins from the culture medium. After the final rinse, additional PBS is added to bring the volume to 5 mL (1×10$^6$ cell/mL). The cell suspension is then reacted with 1 mL of NHS-DNA (11.7 µM) solution synthesized and purified from 30 µL of 5'-thiol ssDNA (C2 sequence). The mixture is allowed to react at room temperature for 30 minutes, and then washed three times with PBS containing 1% FBS. The cells are then resuspended in 0.5 mL of PBS containing 1% FBS.

Figure 17:
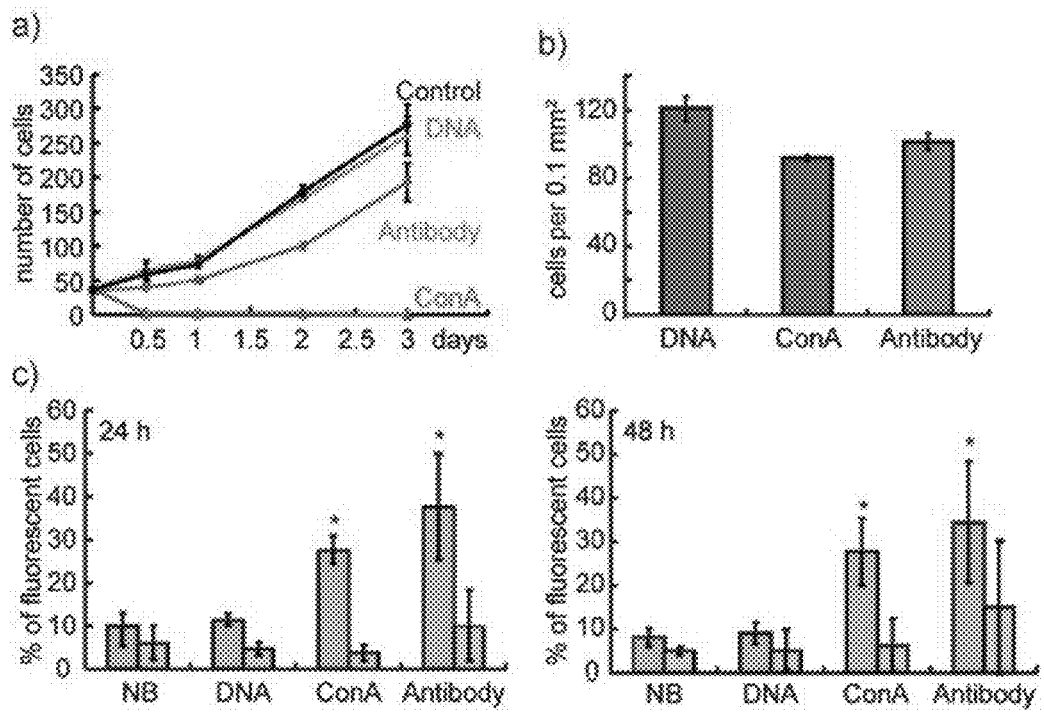
FIG. 17. Comparison of biomolecule-based adhesion methods. a) Bulk cell growth rates were first determined in the presence of the adhesion molecules. A suspension of Jurkat cells was combined with ConA or anti-CD3 IgG, and a solution of DNA-coated cells was combined with the complementary DNA strands. At various time points the total number of cells was counted. The control sample was grown in the absence of any adhesion molecules. b) To evaluate cell capture efficiency, solutions of 20 μM FITC-labeled ssDNA, 20 μM FITC-labeled ConA, and 6 μM FITC-labeled anti-CD3 IgG were applied to aldehyde-coated glass slides, and the biomolecules were attached by reductive amination. Solutions containing $1\times10^7$ Jurkat cell $mL^{-1}$ were then introduced onto the resulting slides. The samples were incubated for 10 min at room temperature and then washed with two portions of phosphate-buffered saline (PBS) before evaluation. c) To evaluate cell viability, cells were immobilized on DNA, ConA, and anti-CD3 IgG coated aldehyde slides. After immobilization for 24 and 48 h, the cells were incubated with a solution of annexin V-FITC (black bars) and PI (gray bars). The cells were evaluated within 1 h by fluorescence microscopy. * ConA and antibody immobilized cells that were partially stained by annexin were counted as cells undergoing apoptosis. NB represents control samples that were not bound to the surfaces. Error bars represent one standard deviation.

The effects of the adhesion molecules on the viability of the cells were assessed using two different methods. First, suspensions of unmodified Jurkat cells were supplemented with ConA or anti-CD3 antibodies, and the solutions of DNA-coated cells were supplemented with the complementary sequence. FIG. 17a shows the growth curves of the resulting cells over a three-day period. The propagation of the DNA-modified cells was the same as that of unmodified cells, but the anti-CD3-treated cells showed delayed growth. ConA-coated cells aggregated and were no longer alive after 12 h. Cell morphology changes induced by soluble biomolecules. Jurkat cells were grown in normal media (Control), DNA-modified Jurkat cells were grown in the presence of 2 µM DNA, and unmodified Jurkat cells were grown in the presence of 2 µM ConA or 0.1 mg/mL Anti-CD3. The resulting cells were examined under a light microscope after a period of 12 h. The appearance of the cells was largely unchanged in the presence of DNA, but cells grown in the presence of ConA and Anti-CD3 exhibited aggregation and other morphological changes.

As a second comparison method, the three cell-adhesion molecules were coated onto commercially available aldehyde-coated glass slides using the same reductive amination procedures outlined above. By visual inspection, all three surfaces were able to achieve efficient cell binding (FIG. 17b), but only the DNA-conjugated cells appeared morphologically unchanged after 48 h. The ConA- and anti-CD3-immobilized cells exhibited significant changes during this time period, likely owing to crosslinking of their surface receptors. The viability of the surface-immobilized cells was determined after 24 and 48 h using annexin V and propidium iodide (PI) staining. For the DNA-immobilized cells, the low percentage of apoptotic and necrotic cells was similar to that of unmodified cells (FIG. 17c). However, the ConA and anti-CD3 immobilized cells showed significantly higher numbers of apoptotic cells compared to the control samples. Thus, the DNA molecules appear only to hybridize with their complementary partners and should have much less potential to disturb the overall physiology of the cells in force measurement experiments.

Live cells were readily captured by AFM tips bearing all three of the biomolecules. This capture was accomplished simply by touching the cell membrane with the cantilevers, with contact times as short as five seconds resulting in the transfer of the cells to the AFM tips. No cells were captured by tips lacking the appropriate biomolecules.

Figure 18:
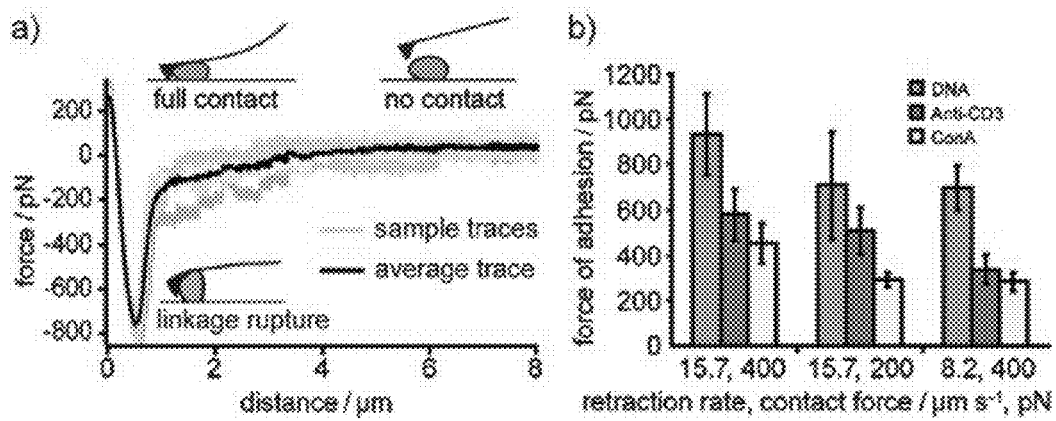
FIG. 18. AFM measurement of de-adhesion force. A) Six sample traces for a single cell are shown in shades of gray, with the average trace shown in black. At zero distance, the cell is in full contact with the cantilever, which is applying a positive force. As distance increases, the cantilever is pulled away from the glass slide surface, causgin the cell-cantilever linkage to rupture and result in the zero-force, no-contact region. The force of d-adhesion was calculated as the difference between the curve minimum and the horizontal no=contact region. B) Adhesion forces were measured under different retraction rates (15.7 and 8.2 μm/s) and contact forces (400 and 200 pN) for the DNA, ConA, and antibody systems. Data were obtained by measuring size de-adhesion events on more than four different cells. Error bards represent one standard deviation.

Our assay to determine the strength of cantilever attachment was designed such that cell-cantilever adhesions were fewer in number, and therefore weaker overall, than DNA-based adhesions between a cell and the complementarily functionalized glass slide. Owing to this arrangement the cell-cantilever interaction would be expected to rupture first, yielding the strength of the interaction that a relatively low concentration of biomolecules can achieve. Rupture of the cell-cantilever interaction before the cell-surface interaction was verified by visual observation during experiments. The force of de-adhesion was measured for each attachment method using two different retraction rates and two different contact forces (FIG. 18a). The measured force of de-adhesion increased with contact force and retraction rate across all attachment methods, as predicted by the Bell model. The ConA attachment method yielded zero-force attachment events in 12% of the de-adhesion measurements. Such events were not observed in the DNA and antibody cases A significant spread of forces was observed for all three attachment methods; however, under all experimental parameters, the DNA method displayed the strongest average adhesion, followed by antibody attachment, then ConA (FIG. 18b). As a control experiment, we also demonstrated that the capture efficiency of ConA and anti-CD3 is not affected by the presence of DNA strands introduced on the cell surface. It should be noted that the overall de-adhesion forces determined for each attachment strategy depend on both the number of linkages and the retraction rates and therefore do not reflect the absolute strengths of the individual biomolecular interactions. For comparison, the force required to separate a typical 20 bp DNA duplex has been previously determined to be 38-50 pN, suggesting that in our experiments roughly 20-25 individual linkages are made between the cell and the cantilever if the interaction strengths are assumed to be simply additive, though multiple parallel bonds can exhibit more complicated scaling behavior. Similar reasoning would suggest that about ten ConA-mannose interactions (at 47 pN each) and 12 antibody-antigen interactions (at 49 pN each) are involved. Experiments to determine the number of linkages involved in each adhesion event are in progress to determine these effects more accurately. Nevertheless, our current results show that the DNA hybridization method leads to the most robust attachment under typical preparation conditions, even though the strength of each individual linkage is likely to be less than that of the other biomolecules.

The strength of the cell-cantilever interaction can be tuned by varying the number of interacting strands and the length of the complementary regions, and the reversibility of DNA hybridization also allows the tips to be used many times. Both of these advantages allowed us to use AFM tips to arrange cells one at a time into patterns. In a recent report, it was shown that individual DNA strands could be moved from one location to another on a printed substrate, allowing small-molecule dyes to be printed in a similar fashion.

Figure 19:
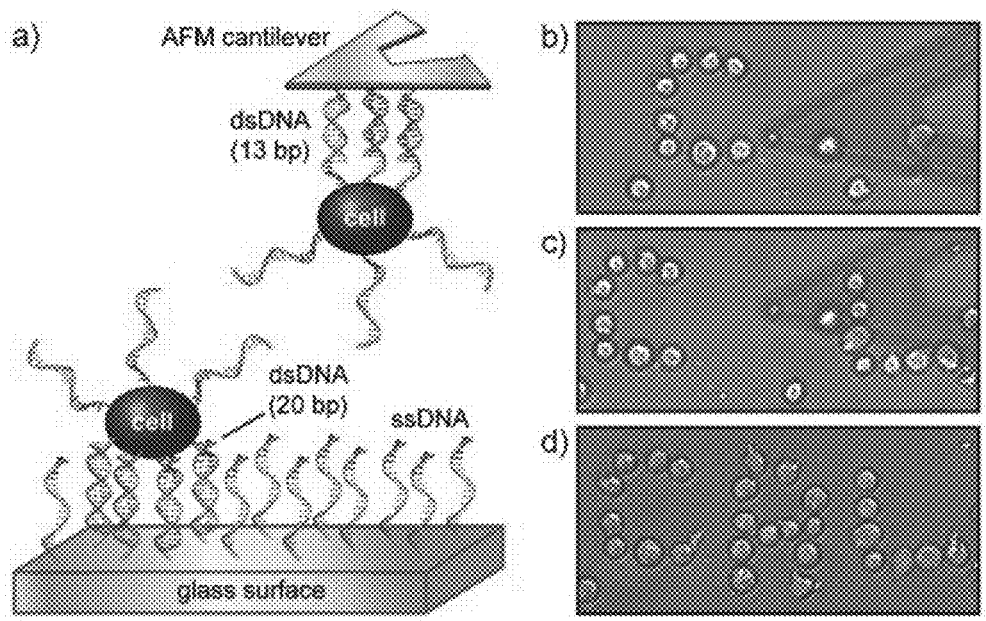
FIG. 19. Dip-pen patterning of live cells. a) By attaching a shorter DNA strand (13 bases) to a cantilever and a longer strand (20 bases) to the glass slide, a single living cell can be transported by the AFM instrument and directly printed at a desired location on the glass slide. b-d) This process shown stepwise for the formation of a single pattern of cells.

To do this, a 5 µM solution of a shorter DNA strand (13 bases) was applied to the cantilever, and an 80 µM solution of a longer strand (20 bases) was coupled to the glass slide. DNA-coated Jurkat cells were incubated in $CO_2$-independent media and applied to the uncoated side of glass slide under an AFM instrument. The cantilever was then lowered into contact with the cell for ten seconds with a contact force of 400 pN. The cantilever was then retracted, and cell attachment to the cantilever was confirmed visually. The attached cells were then moved to the DNA-coated side with maximum rate of 1 mm $s^{-1}$. The cantilever was lowered into contact with the slide, and the cell was allowed to interact with the substrate for ten seconds with a 400 pN contact force. The cantilever was then retracted, whereupon the cell remained attached to the glass slide. By applying this printing method, cells can be given an (x,y) coordinate to position them precisely on a 2D substrate (FIG. 19). The cells were found to remain viable after patterning.

In summary, we have described the development of a versatile DNA-based adhesion method for the study of cell-cell interactions by AFM. The key advantages of this platform include the reusability of the tip, the tunability of the interaction strength, and the use of well-defined chemical linkages. Of the three biomolecule-based attachment strategies that were used, the DNA method proved superior in terms of cell viability after attachment. The use of AFM to form accurate and programmable patterns of individual cells provides a useful tool to understand the influence of neighboring interactions on cell differentiation and regulation. In a previous report, we have shown that complex patterns can be prepared through the self-assembly of DNA-coated cells on surfaces printed with complementary oligonucleotides. The AFM dip-pen method described herein provides a useful complement to this technique that can achieve the higher resolution needed to create and interrogate clusters consisting of multiple cell types. We are currently using this method to elucidate fundamental adhesion mechanisms involved in cancer metastasis, immune synapse formation, and cell-cell communication.

Example 9. Viral Capsids

Modification of Viral Capsids for Multivalent Targeted Delivery Vehicles.

Multivalent and targeted delivery vehicles offer great promise for drug administration and diagnostic imaging. A number of core scaffolds, including polymers, dendrimers, inorganic nanoparticles, and liposomes, have been used with considerable success in these applications. In terms of biomolecule-based vectors, engineered heat shock cages and viral capsids have also been developed to house drug molecules on their interior. For each of these carrier types, a critically important consideration is the installation of receptor-binding groups that enable the selective association of the carriers with targeted tissue types. The most common molecular strategies for this purpose have involved folic acid, cobalamin, carbohydrates, peptides and antibodies, and nucleic acid aptamers. The rich chemical diversity of these molecules, added to the desire to attach multiple copies of each to scaffolds of varying composition, calls for chemical reactions that are exquisitely functional-group tolerant and proceed under physiological conditions.

An increasing number of chemoselective coupling reactions have been advanced for the labeling of full-sized biomolecules. All of the reported methods have their particular strengths and ideal usages, and with the addition of each technique, new possibilities have arisen for the generation of complex structures comprising multiple biomolecular components. To add to this list, we have reported a highly efficient oxidative coupling reaction that occurs between anilines and phenylene diamines in the presence of aqueous sodium periodate. This reaction has shown exceptional chemoselectivity to date, and proceeds rapidly at micromolar concentrations and at neutral pH. In this report, we apply this method to attach 20-60 copies of DNA aptamers to the surface of genome-free viral capsids. The resulting multivalent assemblies bind to tyrosine kinase receptors on the surface of Jurkat cells and are readily endocytosed. Finally, we show that this chemistry can be combined with other bioconjugation methods that could install functional drug molecules within the carriers. The ability of the oxidative coupling strategy to prepare these heterobiomolecular structures bodes well for its use in the preparation of many different types of delivery vehicles.

Bacteriophage MS2 provides a readily available scaffold for the construction of targeted delivery agents. The protein coat of this virus consists of 180 sequence-identical monomers that are arranged in a hollow spherical structure. The coat protein monomer can be expressed and self-assembled readily in *E. coli*, yielding robust, non-toxic and biodegradable structures that are genome-free. See Carrico, Z. M.; Romanini, D. W.; Mehl, R. A.; Francis, M. B. *Chem. Commun.* 2008, 1205-1207 and hereby incorporated by reference. As MS2 capsids possess thirty-two pores that allow access to the inside of the capsid, selective modification can be achieved on both the interior and the exterior surfaces using orthogonal bioconjugation reactions. (Hooker, J. M.; Kovacs, E. W.; Francis, M. B. *Journal of the American Chemical Society.* 2004, 126, 3718-3719; Kovacs, E. W.; Hooker, J. M.; Romanini, D. W.; Holder, P. G.; Berry, K. E.; Francis, M. B. *Bioconjugate Chemistry.* 2007, 18, 1140-1147). In previous reports, we have shown that tyrosine-based chemistry can be used to install F-18 PET tracers (Hooker, J. M.; O'Neil, J. P.; Romanini, D. W.; Taylor, S. E.; Francis, M. *Molecular Imaging and Biology.* 2008, 10, 182-191) and Gd-based MRI contrast enhancement agents (Hooker, J. M.; Datta, A.; Botta, M.; Raymond, K. N.; Francis, M. B. *Nano Letters.* 2007, 7, 2207-2210; Datta, A.; Hooker, J. M.; Botta, M.; Francis, M. B.; Aime, S.; Raymond, K. N. *Journal of the American Chemical Society.* 2008, 130, 2546-2552) to allow their use in imaging applications.

To endow the capsids with specific targeting capabilities, we have developed an efficient synthetic method to attach nucleic acid aptamers to their surfaces. Using the SELEX (Systematic Evolution of Ligands by Exponential Enrichment) process, aptamer sequences can be evolved to bind virtually any target, (Tuerk, C.; Gold, L. *Science.* 1990, 249, 505-510; Ellington, A. D.; Szostak, J. W. *Nature.* 1990, 346, 818-822) and once the composition has been identified, they can be obtained readily using automated solid phase synthesis techniques. Their synthesis is also amenable to the introduction of modified backbones that can improve stability or impart novel functionality. In addition, aptamers can often match or even surpass the specificity and affinity of antibodies, with the added convenience of smaller size. These qualities make them attractive tools for the development of targeted therapeutics and imaging platforms with widely varied targeting capabilities.

In order to install oligonucleotide aptamers on the surface of the MS2 capsids, we chose a previously reported $NaIO_4$-mediated oxidative coupling strategy. This method entails the chemoselective coupling of an N,N-diethyl-N'-acylphenylene diamine moiety to an aniline in the presence of $NaIO_4$. In previous studies, sodium periodate has been used to oxidize the 1,2-diol at the 3'-end of RNA to introduce aldehyde functionalities, but was not observed to degrade the RNA strand. Although this observation suggests that RNA-based aptamers could be used with our method, we chose to proceed with DNA due to its enhanced stability towards hydrolysis during the isolation and handling steps. The aniline coupling partners can be introduced on the exterior surface of MS2 capsids either through direct chemical modification or through the introduction of an unnatural amino acid, p-aminophenylalanine (paF), into position 19 of the MS2 coat protein using the amber stop codon suppression system. (Carrico, Z. M.; Romanini, D. W.; Mehl, R. A.; Francis, M. B. *Chem. Commun.* 2008, 1205-1207). Using the latter route, we have reported previously that the oxidative coupling strategy can introduce over 100 copies of peptide chains bearing phenylene diamine groups. For this report, we again used the suppression method to produce capsids bearing the T19paF mutation (MS2-paF19), thus providing 180 aniline groups for coupling to the exterior surface. In this case, however, we also introduced an N87C mutation to provide 180 sulfhydryl groups on the interior surface for cargo installation. The resulting MS2-paF19-N87C double mutant was obtained with a yield of 10 mg/L of culture.

To develop the reaction conditions, a 20-base DNA sequence, strand A, was first chosen. Starting from an amine-terminated version of this sequence, the N,N-diethyl-N-acylphenylene diamine moiety was easily introduced through acylation with an NHS-ester containing precursor. Next, reaction conditions were screened by varying the concentrations of reacting DNA, sodium periodate, and reaction time (FIG. 25). Optimal DNA coupling was achieved using 10-20 equivalents (200-400 µM) of the DNA conjugate relative to MS2-paF19 coat protein (20 µM, based on monomer) and 250 equivalents of periodate (5 mM) at room temperature for 1 h. An additional increase in the coupling efficiency was observed when the reaction was run at higher concentrations of sodium chloride, which is likely due to the ability of the higher ionic strength to shield the buildup of negative charge density on the capsid surface as more DNA is attached. For strand A, SDS-PAGE and Coomassie staining, followed by optical densitometry, indicated that 32% of the capsid monomers had been modified with a single strand of DNA, corresponding to 55 strands on each intact capsid. Longer sequences showed slightly lower conversion, most likely due to increased steric effects as well as electrostatic repulsion. Following the reaction, the modified capsids could be separated from excess DNA using either size exclusion chromatography or centrifugal concentrators with 100 kDa molecular weight cutoffs. As a technical note, care must be taken to remove all glycerol, ethylene glycol or other vicinal diols from the samples to prevent them from reacting with the periodate.

As shown in FIG. 25*c,d*, the resulting capsids remained intact by transmission electron microscopy (TEM) and dynamic light scattering (DLS). DLS showed an increase of 10.5±0.7 nm in the hydrodynamic diameter upon conjugation of strand A to the capsids. When the complementary strand was introduced, the diameter increased by an additional 3.9±1.0 nm, suggesting that the DNA was still capable of Watson-Crick-Franklin base pairing when conjugated to the exterior of the capsid. The ability to base pair also provides good evidence that the DNA strands are stable throughout the oxidative coupling conditions. Using denatured capsid monomers, base-pairing of the conjugated DNA was further confirmed by SDS-PAGE using a gel-shift assay (FIG. 25*b*).

For functionalization of the interior surface of MS2, standard cysteine bioconjugation was chosen. MS2 contains two native cysteines that have proven to be inaccessible under normal maleimide bioconjugation conditions. Therefore, a double mutant (MS2-paF19-N87C) was expressed to introduce a cysteine on the interior surface. The reactivity of the cysteine mutant was shown, where MS2 becomes fluorescently labeled in the presence of Alexa Fluor 488 maleimide (AF488). Furthermore, MALDI-TOF MS shows near-quantitative conversion to the singly-modified product.

MS2-paF19 capsids lacking the cysteine mutation showed no dye incorporation under identical conditions.

Figure 24:
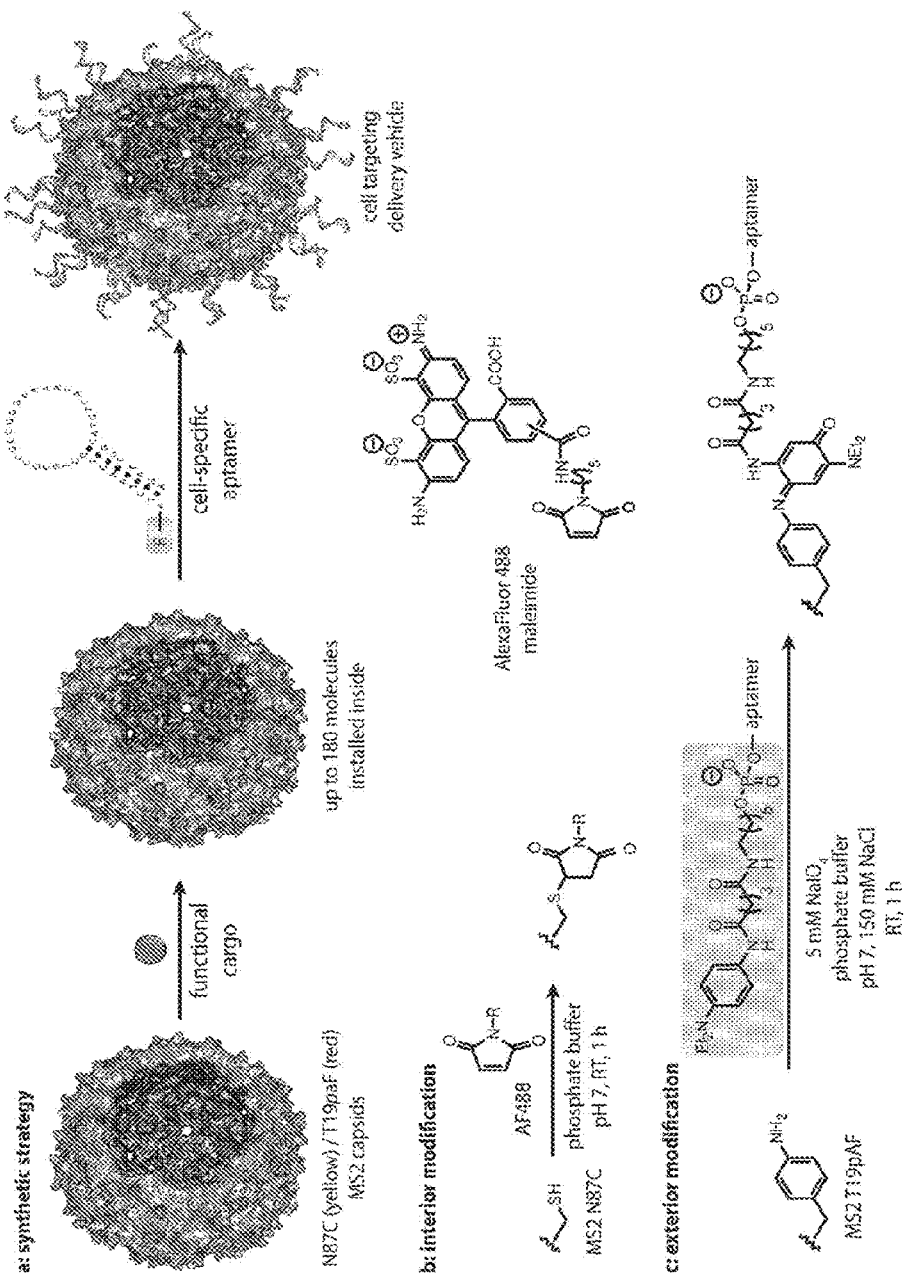

To finish synthesizing the delivery vehicle shown in FIG. 24, a 41-nucleotide DNA aptamer that targets a specific cell surface marker on Jurkat cells (strand B) was chosen as the exterior targeting group. Strand B, previously reported as sgc8c, was isolated using a cell-SELEX process, and its binding partner was determined to be protein tyrosine kinase 7 (PTK7). PTK7 is a transmembrane protein that is present on the surface of Jurkat T leukemia cells, as well as many other leukemia cell lines, and has been proposed as a potential biomarker for T cell acute lymphoblastic leukemia. Using the oxidative coupling strategy, 20-40 copies of diethyl phenylenediamine-labeled strand B were attached to each capsid, as determined by SDS-PAGE and densitometry analysis (FIG. 25a, lane 8). To detect the capsids in cell-binding assays, the interior was modified with AF488 chromophores as described above prior to DNA attachment.

We tested the targeting specificity of these capsids by incubating them with Jurkat cells at 37° C. for 30-60 min in culture media. Subsequent analysis using flow cytometry revealed that samples of cells exposed to MS2 capsids bearing strand B (11 nM in capsids) showed a significant increase in mean fluorescence intensity compared to background cellular autofluorescence, FIG. 26a. For negative controls, we synthesized AF488-modified capsids with no exterior modification (AF488-MS2), as well as ones modified with a 41-nt strand of a randomized sequence (C). Both control capsids did not give rise to an increase in mean fluorescence intensity, confirming the role of the specific aptamer sequence in cell-binding.

Figure 3:
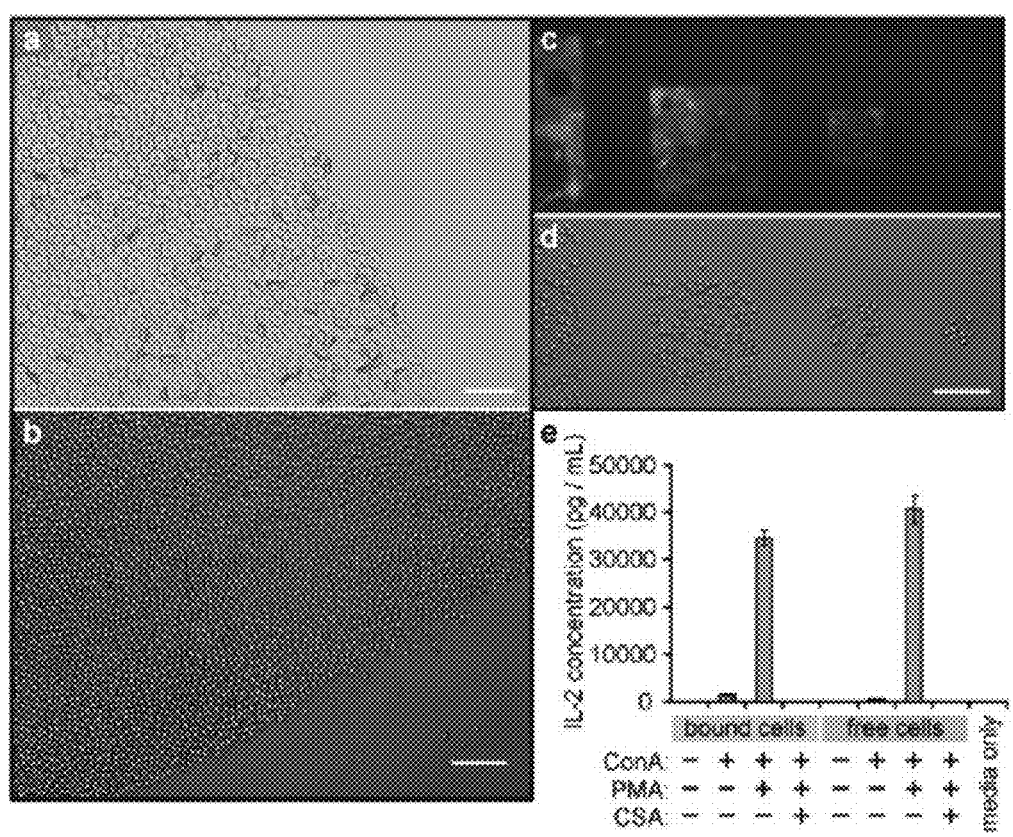
FIG. 3. Direct DNA modification and capture of primary cells. (a) Human red blood cells were bound in the same manner as Jurkat cells on a DNA spot, and appeared to be morphologically identical immediately after binding. Trypan blue staining indicated that the membranes remained intact. (b) DNA-coated mouse CD4+ helper T cells were bound by spots coated with complementary DNA. After 3 minutes of exposure, a clear boundary can be seen between the printed and unprinted regions of the slide. (c) Microscale DNA patterns made by photolithography and microfabrication. Fluoresein-conjugated ssDNA strands were patterned on the substrate to allow visualization. (d) Mouse primary T cells were captured on the same DNA patterns. (e) IL-2 production of DNA-immobilized T cells and free T cells, as determined by ELISA. ConA=concanavalin A. PMA=phorbol meristyl acetate. CSA=cyclosporin A.
Figure 4:
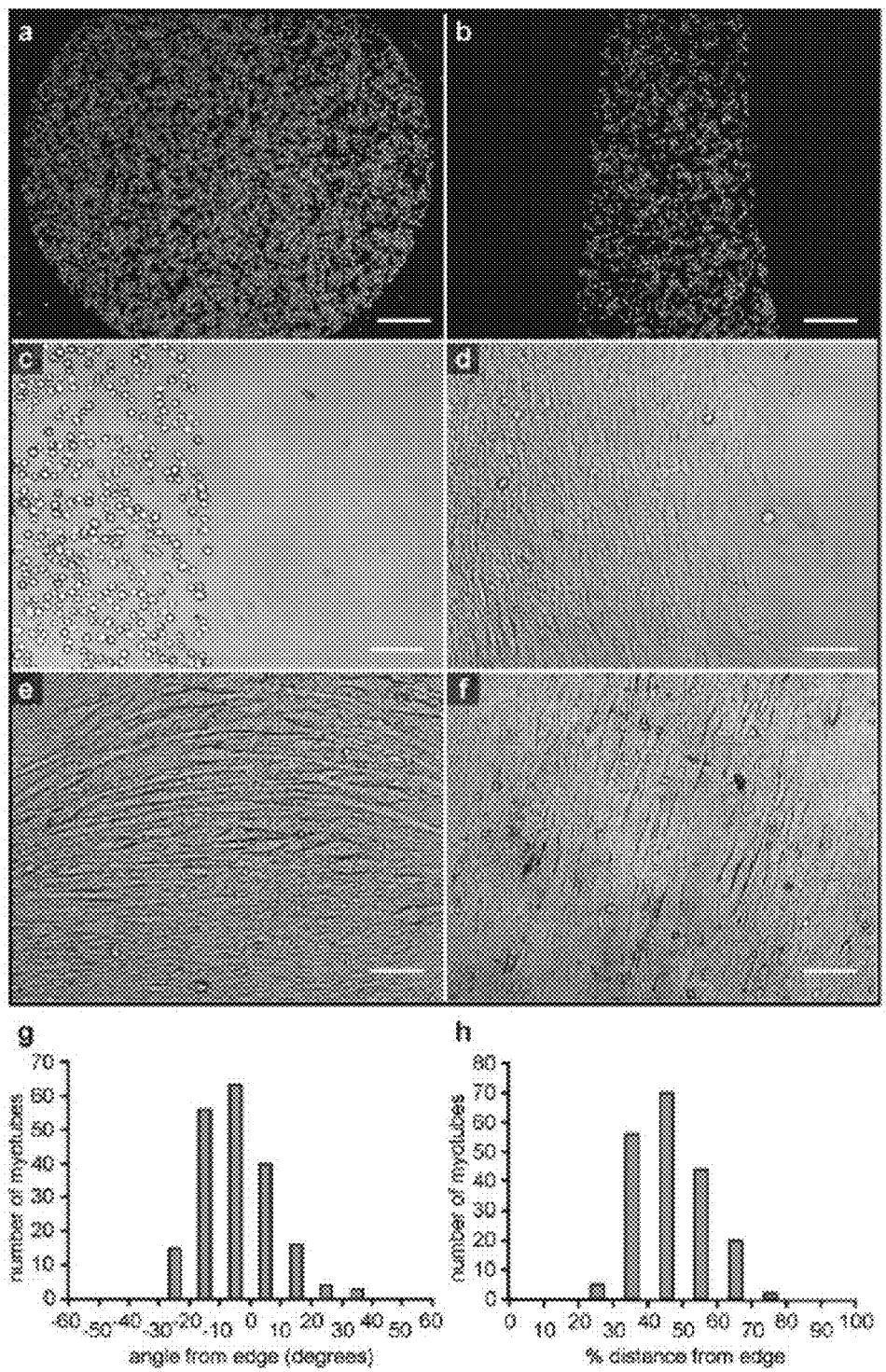
FIG. 4. Capture and differentiation of primary myoblast cells. (a,b) DNA patterns on glass slides dictate the areas in which cells are bound. (c) Myoblast cells show no signs of differentiation immediately after capture (shown), or after 1 day when kept in growth media. (d) Myotubes form upon addition of differentiation media. The photo was taken five days after the switch was made. (e) After 6 days of incubation in differentiation media, circularly patterned myoblasts form arced myotubes that are aligned with the edge. (f) After 6 days, myocytes in rectangular arrangements form myotubes that are aligned with the long axis of the patterns. For the linear patterns, the majority of the myocytes (g) align to within 20° of the pattern boundary angle and (h) are found half way between the edges.
Figure 5:
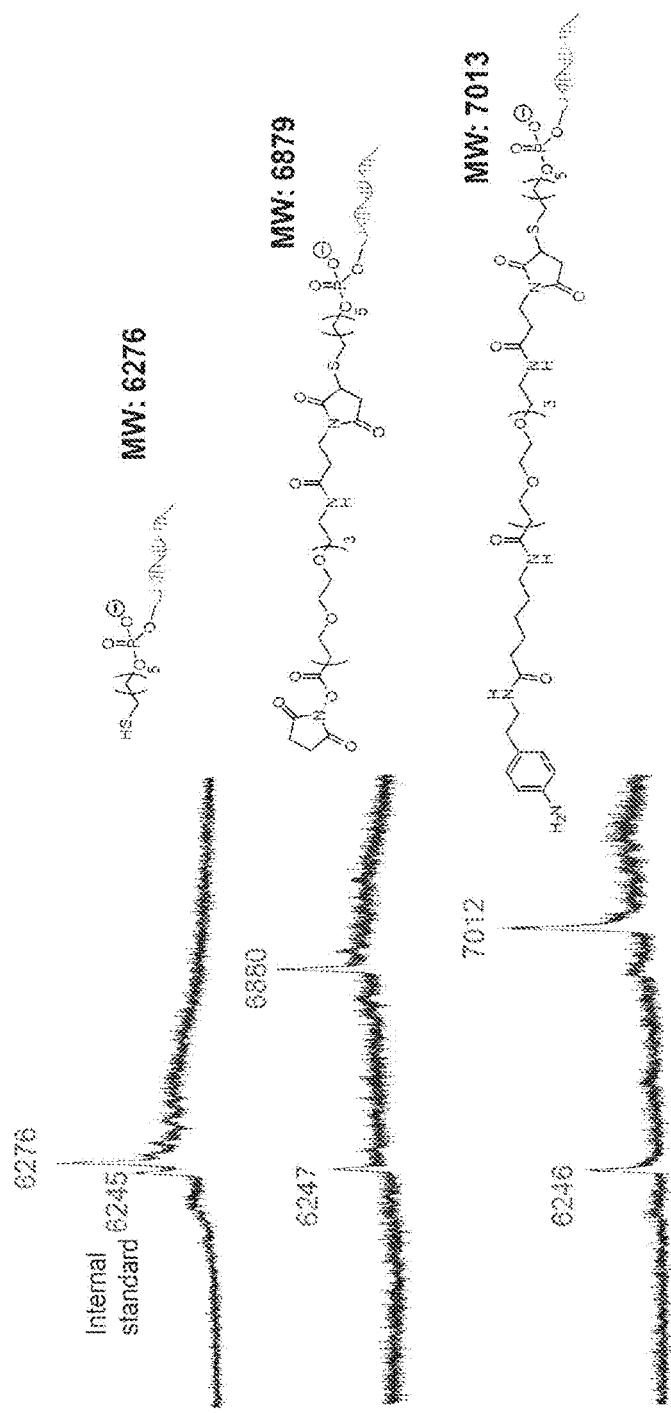
FIG. 5. Matrix-assisted laser desorption ionization time-of-flight (MALDI-TOF) mass spectrometry of DNA modification reactions. A model amine compound was found to react with the NHS ester, verifying the formation of amides on the cell surfaces.
Figure 6:
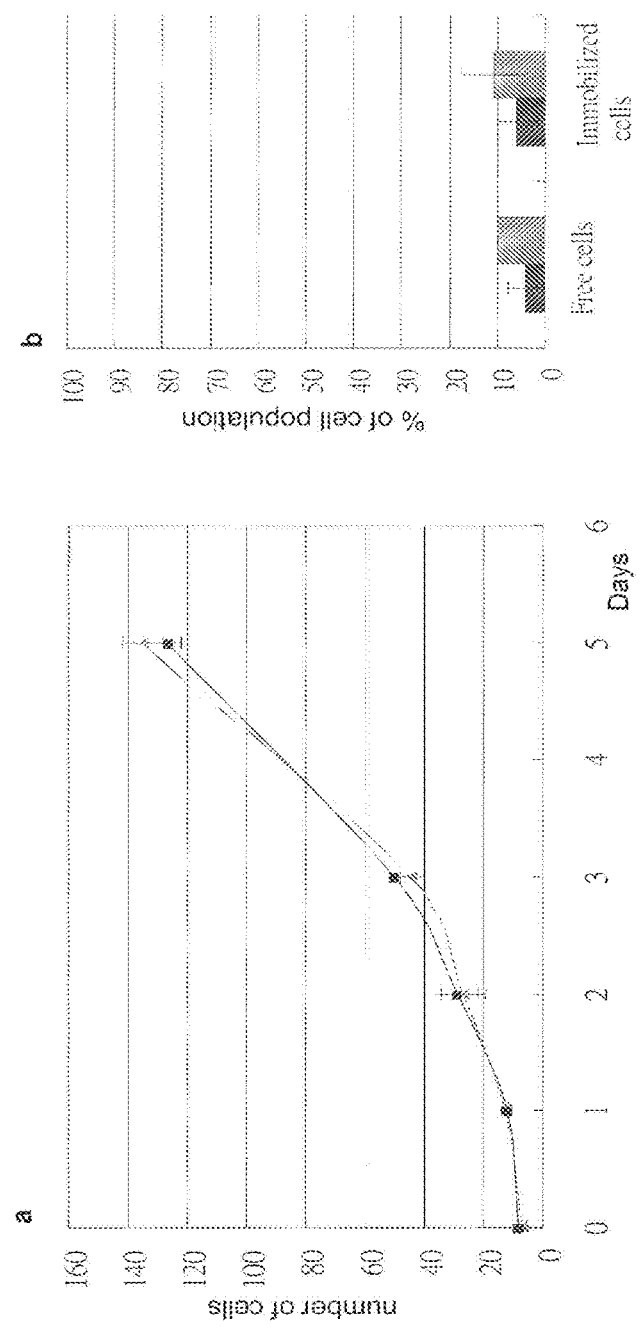
FIG. 6. Viability of Jurkat cells modified with NHS-DNA. A) A solution of DNA-coated cells (20 bases each) was combined with the complementary strands. At various time points the total number of cells was counted visually (Blue curve). The control sample (orange curve) consisted of unmodified Jurkat cells grown in the absence of added DNA. B) To evaluate viability after attachment, DNA-modified cells were immobilized on glass slides bearing the strand complement. After immobilization for 24 h and 48 h, the cells was incubated with a solution of annexin V-FITC (green bars) and PI (red bars). The cells were evaluated within 1 h using fluorescence microscopy. Free cells were control samples that lacked surface DNA and were not bound to the slides.
Figure 7:
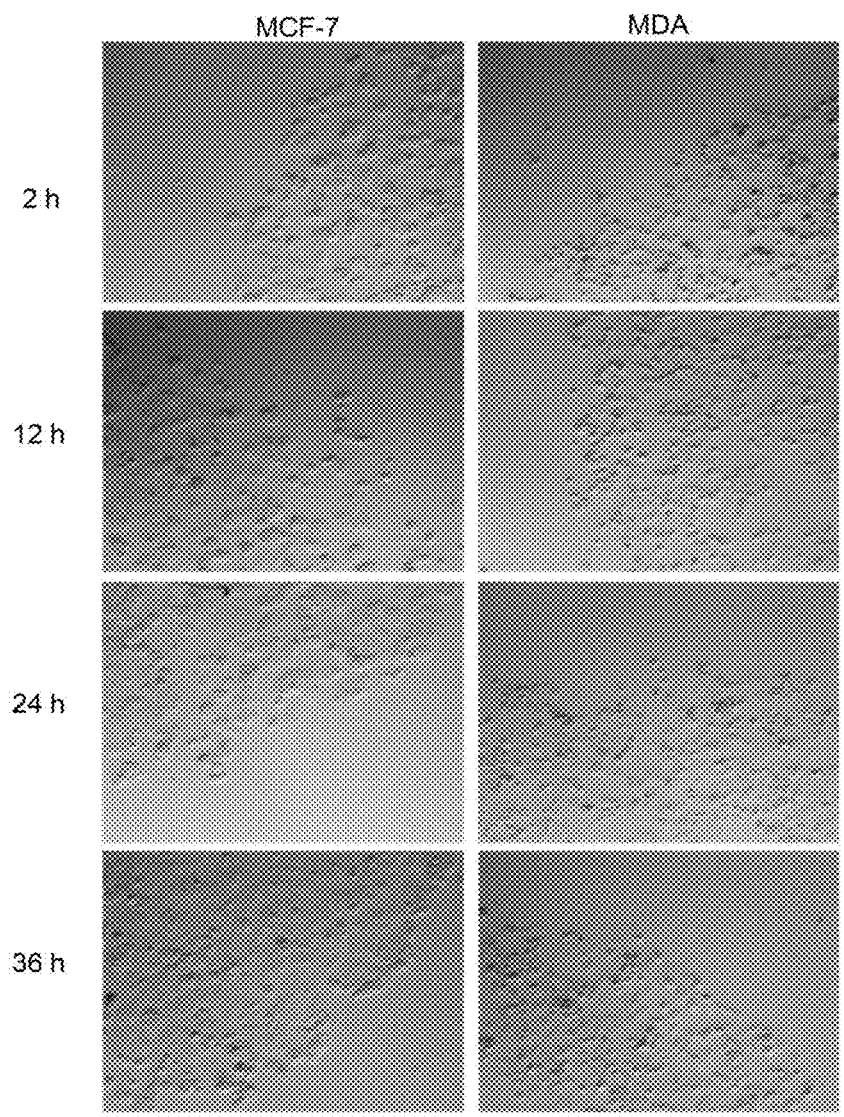
FIG. 7. Immobilized MCF-7 and MDA cells were imaged after 2, 12, 24, 36 hours.
Figure 8:
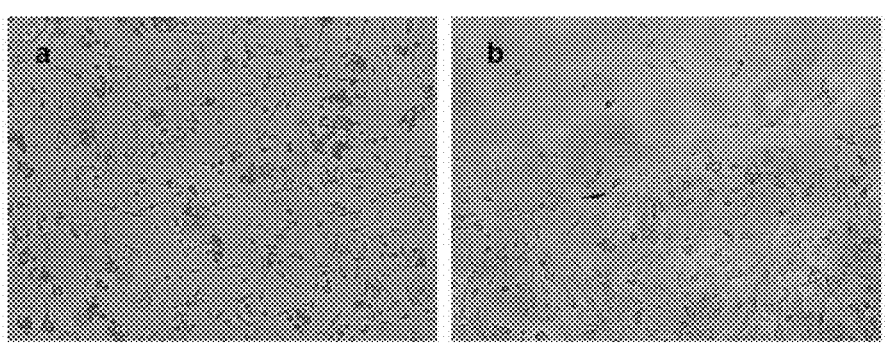
FIG. 8. Myoblasts were incubated in growth media for 3 days. A) Myoblasts were seeded on collagen coated dishes. B) Myoblasts were reacted with NHS-DNA and bound to the surface in a sequence-specific manner.
Figure 9:
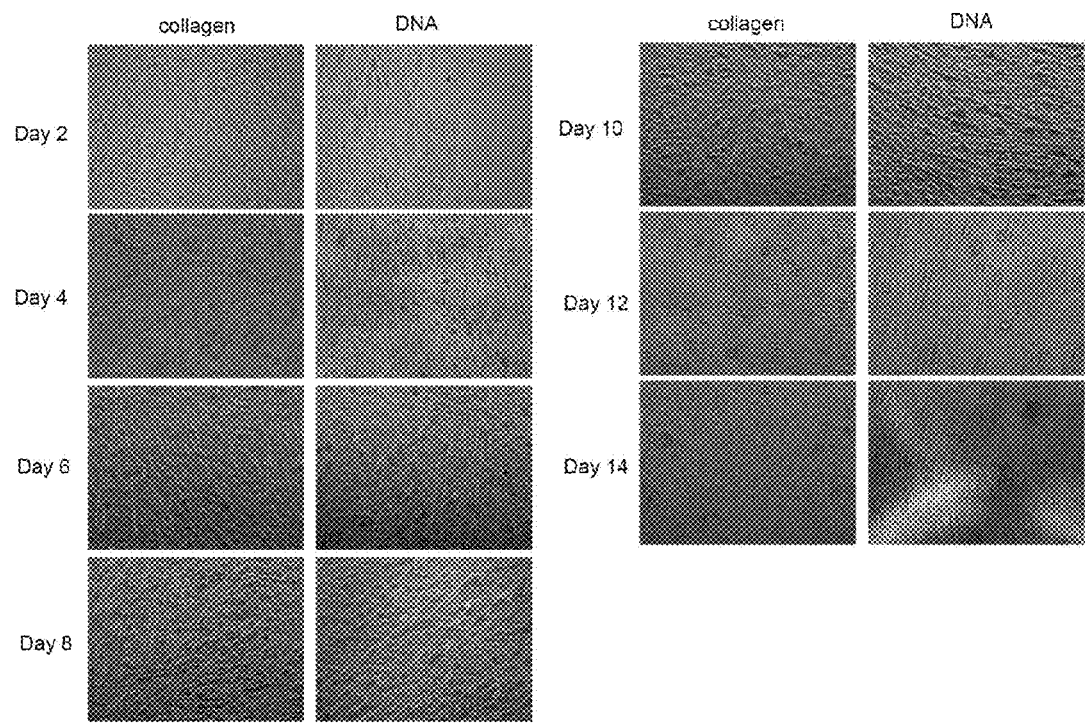
FIG. 9. Myoblasts incubated in fusion media after 2, 4, 6, 8, 10, 12, 14 days and either seeded on collagen coated dishes or reacted with NHS-DNA and bound to the surface in a sequence-specific manner.
Figure 10:
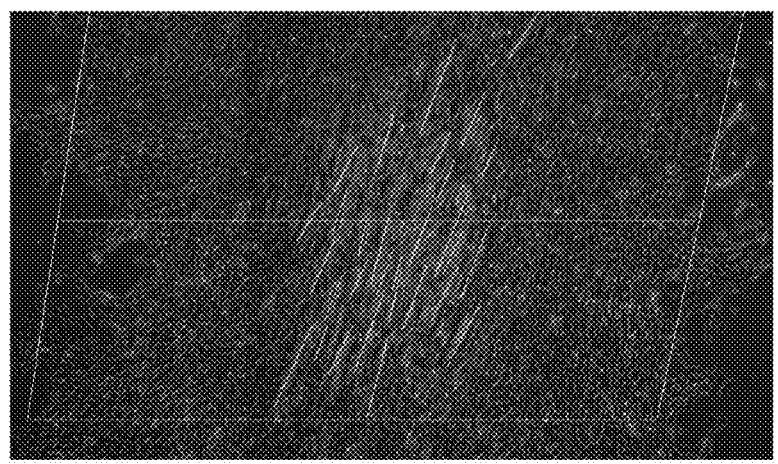
FIG. 10. Analysis of myotube alignment on a defined pattern. The distance (red line) and angles were measured between the myotubes and the nearest edge. All distance measurements were made from the midpoint of the tubes. The full distance between the pattern edges is indicated by the green line.

Having validated the targeting of B-capsids in flow cytometry experiments, we investigated the cellular internalization of the modified capsids with confocal microscopy. After incubation for 30-60 min at 37° C. with Jurkat cells, the presence of capsids labeled with strand B could be detected as brightly fluorescent dots within the cells, FIG. 3b. Co-staining experiments with fluorescent endocytic markers indicated that the B-labeled capsids co-localized with low-density lipoprotein (LDL) particles, but not transferrin. While both transferrin and LDL are known endocytic markers, they traffic through different pathways once inside the cell. Transferrin has been shown to indicate endosomes that are directed back to the surface through the recycling pathway, while vesicles associated with LDL eventually traffic to lysosomes. In combination with the targeting specificity of the α-PTK7 aptamer, the lysosomal fate of B-capsids is encouraging for the targeted drug delivery of acid-labile prodrugs that would be preferentially released upon lysosomal acidification.

For any delivery vehicle composition, the attachment of unprotected biomolecular targeting agents will likely be of key importance to achieve tissue specificity. This report demonstrates the utility of a chemoselective oxidative coupling reaction for this purpose. In principle, the MS2-based vehicle described herein can now be targeted to any receptor for which a binding aptamer has been determined. For the purposes of diagnostic imaging it may not be necessary for the capsids to be internalized; however the observed uptake is envisioned to be highly beneficial for drug delivery applications. In current experiments, we are adding anticancer drugs to these carriers, as well as radionuclides and contrast agents that can be used to determine the location of cellular markers in vivo.

General Procedures and Materials.

Unless otherwise noted, all chemicals and solvents were of analytical grade and used as received from commercial sources. Analytical thin layer chromatography (TLC) was performed on EM Reagent 0.25 mm silica gel 60-F254 plates with visualization by ultraviolet (UV) irradiation at 254 nm or potassium permanganate stain. All organic solvents were removed under reduced pressure using a rotary evaporator. Dichloromethane (CH2Cl2) was distilled under a nitrogen atmosphere from calcium hydride. Water (dd-H2O) used in biological procedures or as the reaction solvent was deionized using a NANOpure purification system (Barnstead, USA). 4-(4-diethylamino-phenylcarbamoyl)-butyric acid succinimidyl ester was prepared using the previously reported method.1 All oligonucleotides were obtained from Integrated DNA Technologies (Coralville, Iowa). Samples were purified by reverse-phase HPLC or NAP-5 gel filtration columns (GE Healthcare). Samples were lyophilized using a LAB CONCO Freezone 4.5 (Lab Conco). Lyophilized oligonucleotides were re-suspended in the appropriate buffer and the concentration was determined by measuring the absorbance at 260 nm. All cell culture reagents were obtained from Gibco/Invitrogen Corp (Carlsbad, Calif.) unless otherwise noted. Cell culture was conducted using standard techniques. Jurkat cells were grown in T-25 culture flasks (Corning, USA) in RPMI Medium 1640 supplemented with 10% (v/v) fetal bovine serum (FBS, HyClone) and 1% penicillin/streptomycin (P/S, Sigma).

Instrumentation and Sample Analysis NMR.

1H and 13C spectra were measured with a Bruker AVQ-400 (400 MHz) spectrometer. Chemical shifts are reported as δ in units of parts per million (ppm) relative to chloroform-d (δ 7.26, s). Multiplicities are reported as follows: s (singlet), d (doublet), t (triplet), q (quartet), dd (doublet of doublets), p (pentet), m (multiplet), br (broadened), or app (apparent). Coupling constants are reported as a J value in Hertz (Hz). The number of protons (n) for a given resonance is indicated nH, and is based on spectral integration values.

Mass Spectrometry.

Matrix assisted laser desorption-ionization time-of-flight mass spectrometry (MALDI-TOF MS) was performed on a Voyager-DETM system (PerSeptive Biosystems, USA). Prior to MALDI-TOF MS analysis, samples were desalted using C18 ZipTip® pipet tips (Millipore, USA). Oligonucleotide samples were co-crystallized using a 3-hydroxypicolinic acid:ammonium citrate solution (45 mg/mL:5 mg/mL in 4.5:5.5 MeCN:ddH2O). For electrospray ionization mass spectrometry (ESI-MS) oligonucleotide conjugates were analyzed using an LTQ Orbitrap XL mass spectrometer equipped with an Ion Max electrospray ionization (ESI) source (Thermo Fisher Scientific, Waltham, Mass.). Sample solutions were infused into the ESI probe at a flow rate of 5 µL/min using a syringe pump. The voltages applied to the ion optics were adjusted automatically for optimum desolvation and transmission of the ions of interest using Tune Plus software (version 2.4, Thermo). Mass spectra were recorded in the negative ion mode over the range m/z=500 to 2000 for a period of two minutes. Mass spectra were processed using Xcalibur software (version 4.1, Thermo) and the measured charge state distributions were deconvoluted using ProMass software (version 2.5 SR-1, Novatia, Monmouth Junction, N.J.). Prior to ESI-MS analysis, oligonucleotides were prepared as previously described.2 All MS data for oligonucleotides and protein samples were found to be within 0.1% of the expected values.

High Performance Liquid Chromatography (HPLC).

HPLC was performed on an Agilent 1100 Series HPLC System (Agilent Technologies, USA). Sample analysis for all HPLC experiments was achieved with an inline diode array detector (DAD). Both analytical and preparative reverse-phase HPLC of oligonucleotides was accomplished using a C18 stationary phase and a MeCN/100 mM triethylammonium acetate (TEAA, pH=7.0) gradient.

Gel Analyses.

For protein analysis, sodium dodecyl sulfate-polyacrylamide gel electrophoresis (SDS-PAGE) was carried out on a Mini-Protean apparatus from Bio-Rad (Hercules, Calif.), following the protocol of Laemmli.3 All protein electrophoresis samples were heated for 10 minutes at 100° C. in the presence of 1,4-dithiothreitol (DTT) to ensure reduction of any disulfide bonds. Gels were run for 5 minutes at 30V and 70-90 minutes at 120V to allow good separation of bands. Commercially available markers (Bio-Rad) were applied to at least one lane of each gel for assignment of apparent molecular masses. Visualization of protein bands was accomplished by staining with Coomassie Brilliant Blue R-250 (Bio-Rad). For fluorescent protein conjugates, visualization was accomplished on a UV backlight. Gel imaging was performed on an EpiChem3 Darkroom system (UVP, USA).

Dynamic Light Scattering.

DLS measurements were obtained using a Malvern Instruments Zetasizer Nano ZS, usage courtesy of Jean Fréchet. Data plots and standard deviations are calculated from an average of three measurements, each of which consists of 10 runs of 45 seconds each. Measurement data are presented as an intensity plot, which weights larger dimensions by a factor of 106 more than smaller dimensions. Samples taken in 10 mM pH 7.0 phosphate buffer.

Transmission Electron Microscopy (TEM).

TEM images were obtained at the UCBerkeley Electron Microscope Lab using a FEI Tecnai 12 transmission electron microscope with 100 kV accelerating voltage. TEM grids were prepared by charging carbon-coated, formvar-supported copper mesh grids with argon plasma (40 mA at 0.1 mbar for 30 s) in a Cressington 108 Auto Sputter Coater. Protein samples were prepared for TEM analysis by pipetting 5 µL samples onto these grids and allowing them to equilibrate for 3 minutes. The samples were then wicked with filter paper and rinsed with ddH2O. The grids were then exposed to 5 µL of a 1% (w/v) aqueous solution of uranyl acetate for 90 s as a negative stain. After excess stain was removed, the grid was allowed to dry in air.

Experimental General Procedure for the Addition of Phenylene Diamine to Oligonucleotides.

DNA oligonucleotides were purchased containing a primary amine on the 5'-end. A typical reaction is as follows: DNA at a concentration 300 µM is reacted with 4-(4-diethylamino-phenylcarbamoyl)-butyric acid succinimidyl ester (60-120 eq) in 1:1 solution of DMF and 50 mM pH 8.0 phosphate buffer. The reaction mixture is briefly vortexed and then allowed to react at rt for 2 h. Either RPHPLC or commercially available gel filtration columns can be used to purify the small molecule from DNA, following the commercially provided protocol. Following purification, DNA is lyophilized and then re-suspended in the desired buffer. Concentration is determined by measuring the absorbance at 260 nm. The sequence identities of A, B, and C are as follows:

A:
(SEQ ID NO: 7)
5'-TCATACGACTCACTCTAGGGA-3'

B:
(SEQ ID NO: 8)
5'-ATCTAACTGCTGCGCCGCCGGGAAAATACTGTACGGTTAGA-3'

C:
(SEQ ID NO: 9)
5'-CCCTAGAGTGAGTCGTATGACCCTAGAGTGAGTCGTATGAA-3'

General Procedure for DNA Conjugation to MS2.

An eppendorf tube is charged with either MS2-paF19 or MS2-paF19-N87C (20 µM), phenylene diamine-containing oligonucleotide (200-400 µM), and NaIO4 (5 mM). The reaction is carried out in 50 mM pH 7.0 phosphate buffer containing 150 mM NaCl. The reaction is briefly vortexed and allowed to react at rt for 1 h. After an hour, for a 50 µL reaction, the reaction is quenched by the addition of 5 µL of 500 mM tris(2-carboxyethyl)phosphine hydrochloride (TCEP). For purification, the sample is first bufferexchanged by gel filtration (NAP-5) into the desired buffer. The excess DNA is then removed by successive centrifugal filtration using 100 k molecular weight cutoff filters (Millipore).

Cloning and Expression of MS2 Mutants.

The pBAD-MS2-paF19 plasmid production and growth has been previously reported.1 We would like to thank the Peter Schultz lab (Scripps Research Institute, LaJolla, Calif.) for the tRNA- and tRNA-synthetase-encoding plasmids necessary for p-aminophenylalanine (paF) incorporation. Position 87 was mutated into a cysteine using the following forward and reverse primers: Forward: 5'-AGCCGCATG-GCGTTCGTACTTATGTATGGAACTAACCATTC-3' (SEQ ID NO:25); Reverse: 5'-GAATGGTTAGTTCCATA-CATAAGTACGAACGCCATGCGGCT-3' (SEQ ID NO:26). Growth and purification of MS2-paF19-N87C was identical to that of MS2-paF19, although a lower yield was obtained for MS2-paF19-N87C (~1-10 mg/L as compared to ~20 mg/L for MS2-paF19).

Dual-Surface Modification of MS2-paF19-N87C.

MS2-paF19-N87C is first modified on the interior cysteine. For the cysteine alkylation reaction, Alexa Fluor 488 maleimide (Invitrogen) (15 µL of a 19 mM solution in DMSO) is added to MS2-paF19-N87C (285 µL of a 100 µM solution in 10 mM pH 7.2 phosphate buffer). The reaction is briefly vortexed and allowed to react at rt for 1 h. Excess small molecule is removed by gel filtration (NAP-5) and the remaining protein was concentrated using centrifugal filtration. It is important to note that centrifugal filters were prerinsed before use as we found this to prevent problems with the oxidative coupling step. The exterior modification was performed as described above.

Flow Cytometry of Fluorescent Capsids.

Flow cytometry analysis was acquired on a FACSCalibur flow cytometer (BD Biosciences, USA) using a standard 488 Ar laser. Data were collected for at least 10,000 live cells for all experiments. Jurkat cells (1×106 cells in 250 µL) were treated with fluorescent capsids (2 µM) in culture media and incubated either on ice or at 37° C. for 30-60 min. After incubation, the cells were washed twice with 1 mL of fresh media, and then analyzed on the flow cytometer.

Confocal Microscopy.

Confocal fluorescence imaging was carried out on a Zeiss LSM510 META/NLO Axioimager using a 63× Achroplan IR oil-immersion objective lens. Double labeling of Jurkat cells was performed by incubating cells with modified MS2 (20 µM) and DiILDL (15 µg/mL, Invitrogen) or Alexa Fluor 594-Transferrin (25 µg/mL, Invitrogen) for 30-60 min at 37° C. Modified MS2 (fluorescently-labeled with Alexa Fluor 488) was excited at 488 nm and emission was collected between 495-530 nm. Both DiI-LDL and AF594-Transferrin were excited with a 543 nm line and emission was collected between 590-625 nm and 590-655 nm, respectively.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

| SEQUENCES | |
|---|---|
| GTA ACG ATC CAG CTG TCA CT | SEQ ID NO: 1 |
| AGT GAC AGC TGG ATC GTT AC | SEQ ID NO: 2 |
| TCA TAC GAC TCA CTC TAG GG | SEQ ID NO: 3 |
| CCC TAG AGT GAG TCG TAT GA | SEQ ID NO: 4 |
| ACT GAC TGA CTG ACT GAC TG | SEQ ID NO: 5 |
| CAG TCA GTC AGT CAG TCA GT | SEQ ID NO: 6 |
| TCATACGACTCACTCTAGGGA | SEQ ID NO: 7 |
| ATCTAACTGCTGCGCCGCCGGGAAAATACTGTACGGTTAGA | SEQ ID NO: 8 |
| CCCTAGAGTGAGTCGTATGACCCTAGAGTGAGTCGTATGAA | SEQ ID NO: 9 |

What is claimed is:

1. A method of preparing a conjugate of a live cell and a nucleic acid moiety, wherein (i) the cell has a surface comprising a native functional group comprising an amino acid selected from the group consisting of lysine, cysteine, tyrosine, threonine, serine, aspartic acid, glutamic acid and tryptophan, and wherein the native functional group is not an azide-modified sugar, and (ii) the cell has no cell wall, the method comprising:

contacting the cell with an activated nucleic acid moiety under conditions such that the activated nucleic acid moiety reacts with the native functional group to covalently link the nucleic acid directly to the native functional group.

2. The method of claim 1, wherein the cell is a primary cell.

3. The method of claim 1, wherein the cell is a mammalian cell.

4. The method of claim 1, wherein the cell is a stem cell.

5. The method of claim 1, wherein the native functional group comprises lysine.

6. The method of claim 1, wherein the nucleic acid moiety comprises a member selected from the group consisting of an oligonucleotide, DNA, RNA, PNA and an aptamer.

7. The method of claim 1, wherein the nucleic acid moiety comprises single-stranded DNA.

8. The method of claim 1, wherein the nucleic acid moiety comprises from about 10 to about 200 nucleic acids.

9. The method of claim 1, wherein the nucleic acid moiety comprises an aptamer.

10. The method of claim 1, wherein the nucleic acid moiety comprises a linker.

11. The method of claim 1, wherein the conjugate comprises a mammalian cell comprising lysine on the cell surface; and a single-stranded deoxy-nucleic acid covalently linked to the lysine via an amide.

12. A method of preparing a conjugate of a live cell and a nucleic acid moiety, wherein (i) the cell has a surface comprising a native functional group selected from the group consisting of lysine and tryptophan, and (ii) the cell has no cell wall, the method comprising contacting the cell with an activated nucleic acid moiety under conditions such that the activated nucleic acid moiety reacts with a primary amine of the native functional group to form a covalent bond.

13. The method of claim 12, wherein the cell is a primary cell.

14. The method of claim 12, wherein the cell is a mammalian cell.

15. The method of claim 12, wherein the cell is a stem cell.

16. The method of claim 12, wherein the cell has not undergone metabolic engineering to introduce an azide modified sugar.

17. The method of claim 12, wherein the native functional group comprises lysine.

18. The method of claim 12, wherein the nucleic acid moiety comprises a member selected from the group consisting of an oligonucleotide, DNA, RNA, PNA and an aptamer.

19. The method of claim 12, wherein the nucleic acid moiety comprises single-stranded DNA.

20. The method of claim 12, wherein the nucleic acid moiety comprises from about 10 to about 200 nucleic acids.

21. The method of claim 12, wherein the nucleic acid moiety comprises an aptamer.

22. The method of claim 12, wherein the nucleic acid moiety comprises a linker.

23. The method of claim 12, wherein the conjugate comprises a mammalian cell comprising lysine on the cell surface; and a single-stranded deoxy-nucleic acid covalently linked to the lysine via an amide.

24. A method of preparing a conjugate of a live cell and a nucleic acid moiety, wherein the cell has a surface comprising a native functional group comprising an amino acid selected from the group consisting of lysine, cysteine, tyrosine, threonine, serine, aspartic acid, glutamic acid, and tryptophan, and wherein the cell has no cell wall, the method comprising: contacting the cell with an activated nucleic acid moiety under conditions such that the nucleic acid moiety reacts with the amino acid to form a covalent bond.

25. The method of claim 24, wherein the cell is a primary cell.

26. The method of claim 24, wherein the cell is a mammalian cell.

27. The method of claim 24, wherein the cell is a stem cell.

28. The method of claim 24, wherein the cell has not undergone metabolic engineering to introduce an azide modified sugar.

29. The method of claim 24, wherein the native function group comprises lysine.

30. The method of claim 24, wherein the nucleic acid moiety comprises a member selected from the group consisting of an oligonucleotide, DNA, RNA, PNA and an aptamer.

31. The method of claim 24, wherein the nucleic acid moiety comprises single-stranded DNA.

32. The method of claim 24, wherein the nucleic acid moiety comprises from about 10 to about 200 nucleic acids.

33. The method of claim 24, wherein the nucleic acid moiety comprises an aptamer.

34. The method of claim 24, wherein the nucleic acid moiety comprises a linker.

* * * * *